United States Patent
Jang

(10) Patent No.: US 11,492,384 B2
(45) Date of Patent: Nov. 8, 2022

(54) FUSION PROTEIN COMPRISING IL-2 PROTEIN AND CD80 PROTEIN, AND USE THEREOF

(71) Applicant: GI INNOVATION, INC., Seoul (KR)

(72) Inventor: Myung Ho Jang, Seoul (KR)

(73) Assignee: GI INNOVATION, INC., Seoul (KR)

( * ) Notice: Subject to any disclaimer, the term of this patent is extended or adjusted under 35 U.S.C. 154(b) by 161 days.

(21) Appl. No.: 16/959,312

(22) PCT Filed: Sep. 16, 2019

(86) PCT No.: PCT/KR2019/011928
§ 371 (c)(1),
(2) Date: Jun. 30, 2020

(87) PCT Pub. No.: WO2020/060122
PCT Pub. Date: Mar. 26, 2020

(65) Prior Publication Data
US 2020/0369740 A1 Nov. 26, 2020

Related U.S. Application Data

(60) Provisional application No. 62/832,013, filed on Apr. 10, 2019.

(30) Foreign Application Priority Data

Sep. 17, 2018 (KR) .................. 10-2018-0110698
Jan. 7, 2019 (KR) .................. 10-2019-0001867
May 8, 2019 (KR) .................. 10-2019-0053436

(51) Int. Cl.
*C07K 14/55* (2006.01)
*A61P 31/12* (2006.01)
*A61P 35/00* (2006.01)
*C07K 14/705* (2006.01)
*A61K 38/00* (2006.01)

(52) U.S. Cl.
CPC .............. *C07K 14/55* (2013.01); *A61P 31/12* (2018.01); *A61P 35/00* (2018.01); *C07K 14/70532* (2013.01); *A61K 38/00* (2013.01); *C07K 2319/31* (2013.01)

(58) Field of Classification Search
CPC .................................................. C07K 14/55
See application file for complete search history.

(56) References Cited

U.S. PATENT DOCUMENTS

| | | |
|---|---|---|
| 9,567,399 B1 | 2/2017 | Campbell et al. |
| 2013/0149305 A1 | 6/2013 | Ostrand-Rosenberg |
| 2016/0175397 A1 | 6/2016 | Umana et al. |
| 2017/0145071 A1 | 5/2017 | Brennan et al. |

FOREIGN PATENT DOCUMENTS

| | | |
|---|---|---|
| JP | 2002-515251 A | 5/2002 |
| JP | 2014-500868 A | 1/2014 |
| JP | 2014-506793 A | 3/2014 |
| KR | 10-2018-0069903 A | 6/2018 |
| WO | 99/60135 A1 | 11/1999 |
| WO | 2005/017148 A1 | 2/2005 |
| WO | 2012/062228 A2 | 5/2012 |
| WO | 2017/220989 A1 | 12/2017 |
| WO | 2018184964 A1 | 10/2018 |

OTHER PUBLICATIONS

Chan et al., "IL-2/B7.1 (CD80) Fusagene Transduction of AML Blasts by a Self-Inactivating Lentiviral Vector Stimulates T Cell Responses in Vitro: a Strategy to Generate Whole Cell Vaccines for AML", Molecular Therapy, vol. 11, No. 1, Jan. 2005, pp. 120-131.
Paul M. Sondel et al., "Current and Potential Uses of Immunocytokines as Cancer Immunotherapy", Antibodies, Jul. 4, 2012, pp. 149-171, vol. 1.
Susannah D. Barbee et al., "Abstract BOOS: FPT155, a novel therapeutic CD80-Fc fusion protein with potent antitumor activity in preclinical models", Molecular Cancer Therapeutics, Oct. 26-30, 2017, 2 pages.
International Search Report for PCT/KR2019/0011928, dated Dec. 30, 2019.
International Searching Authority, International Preliminary Report on Patentability dated Mar. 9, 2021 in Application No. PCT/KR2019/011928 with English translation.
International Searching Authority, Written Opinion dated Dec. 30, 2019 in Application No. PCT/KR2019/011928 with English translation.
International Searching Authority, International Search Report dated Dec. 30, 2019 in Application No. PCT/KR2019/011928 with English translation.
Tania Carmenate et al., "Human IL-2 Mutein with Higher Antitumor Efficacy Than Wild Type IL-2", The Journal of Immunology, 2013, vol. 190, No. 12, pp. 6230-6238 (9 pages total).
Kong et al., "Expression of fusion IL2-B7.1(IgV+C) and effects on T lymphocytes", Biochem. Cell Biol., 2007, vol. 85, pp. 685-695 (11 pages total).
Chan et al., "1131. Generation of Whole Cell Vaccines for Acute Myeloid Leukaemia by Lentivirus Mediated IL-2/CD80 Transduction", Molecular Therapy, 2005, vol. 11, Supplement 1, p. S436 (1 page total).
Xiaoying Chen et al., "Fusion protein linkers: Property, design, and functionality", Advanced Drug Delivery Reviews, 2013, vol. 65, pp. 1357-1369 (13 pages total).

*Primary Examiner* — Prema M Mertz
(74) *Attorney, Agent, or Firm* — Sughrue Mion, PLLC

(57) ABSTRACT

Provided is a fusion protein comprising IL-2 protein and CD80 protein. A fusion protein comprising CD80 fragment, immunoglobulin Fc, and an IL-2 variant can activate immune cells, such as natural killer cells, and at the same time, can control immune cell regulatory activity of regulatory T cells. Therefore, a pharmaceutical composition comprising the fusion protein as an active ingredient is very industrially useful in that such pharmaceutical composition can increase immune activity in the body, and thus can be effectively used against infectious diseases as well as cancer.

21 Claims, 63 Drawing Sheets

Specification includes a Sequence Listing.

[Fig. 1]
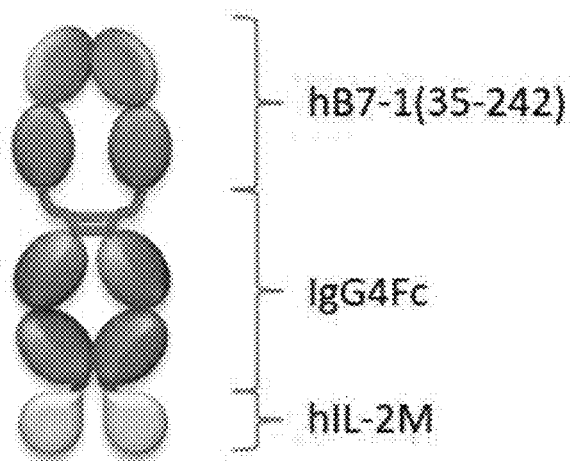
[Fig. 2]
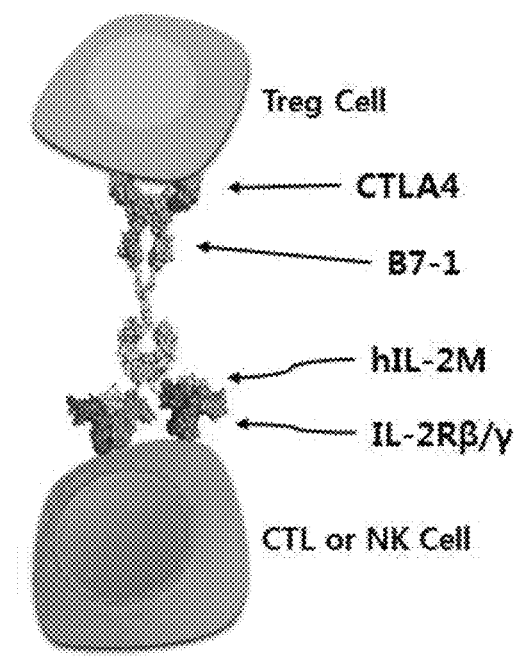

[Fig. 3]
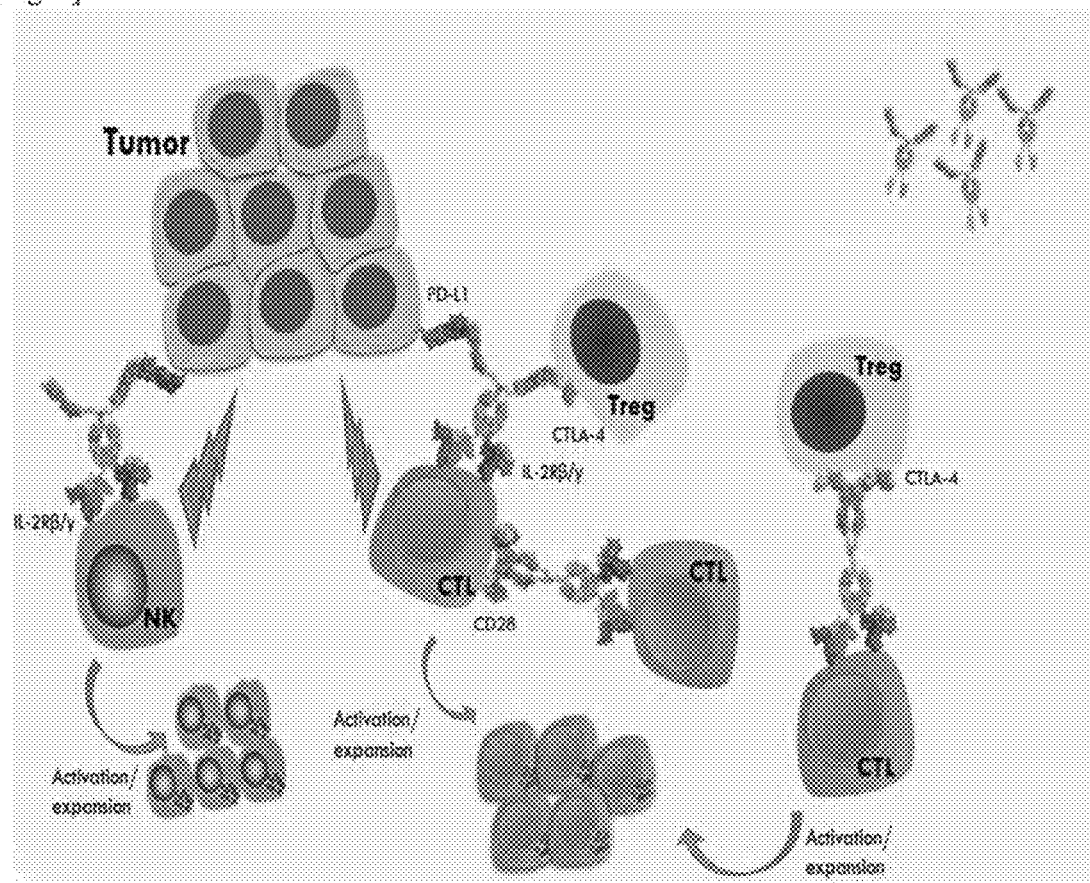
[Fig. 4]

[Fig. 5]
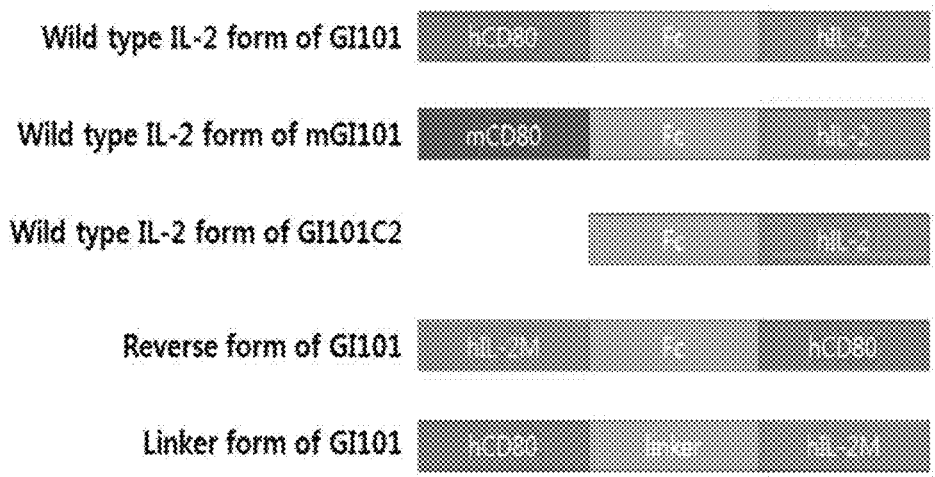
[Fig. 6]
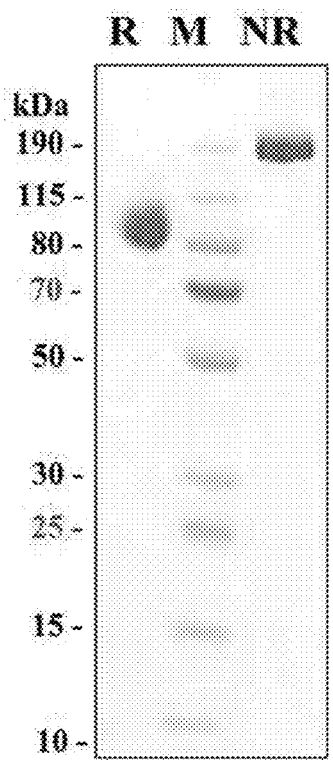

[Fig. 7]
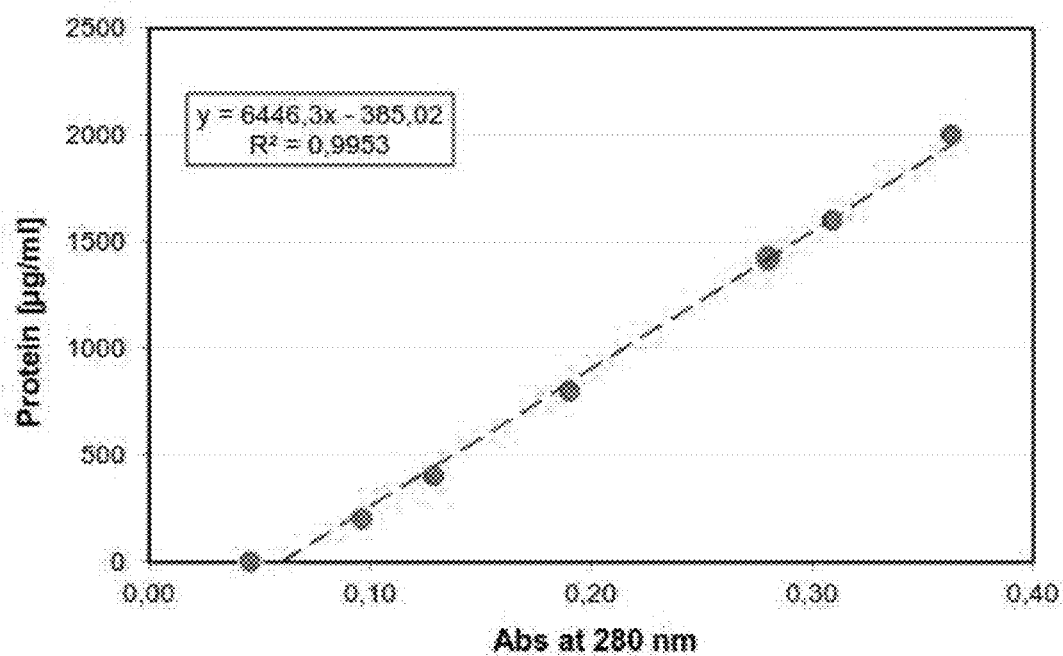

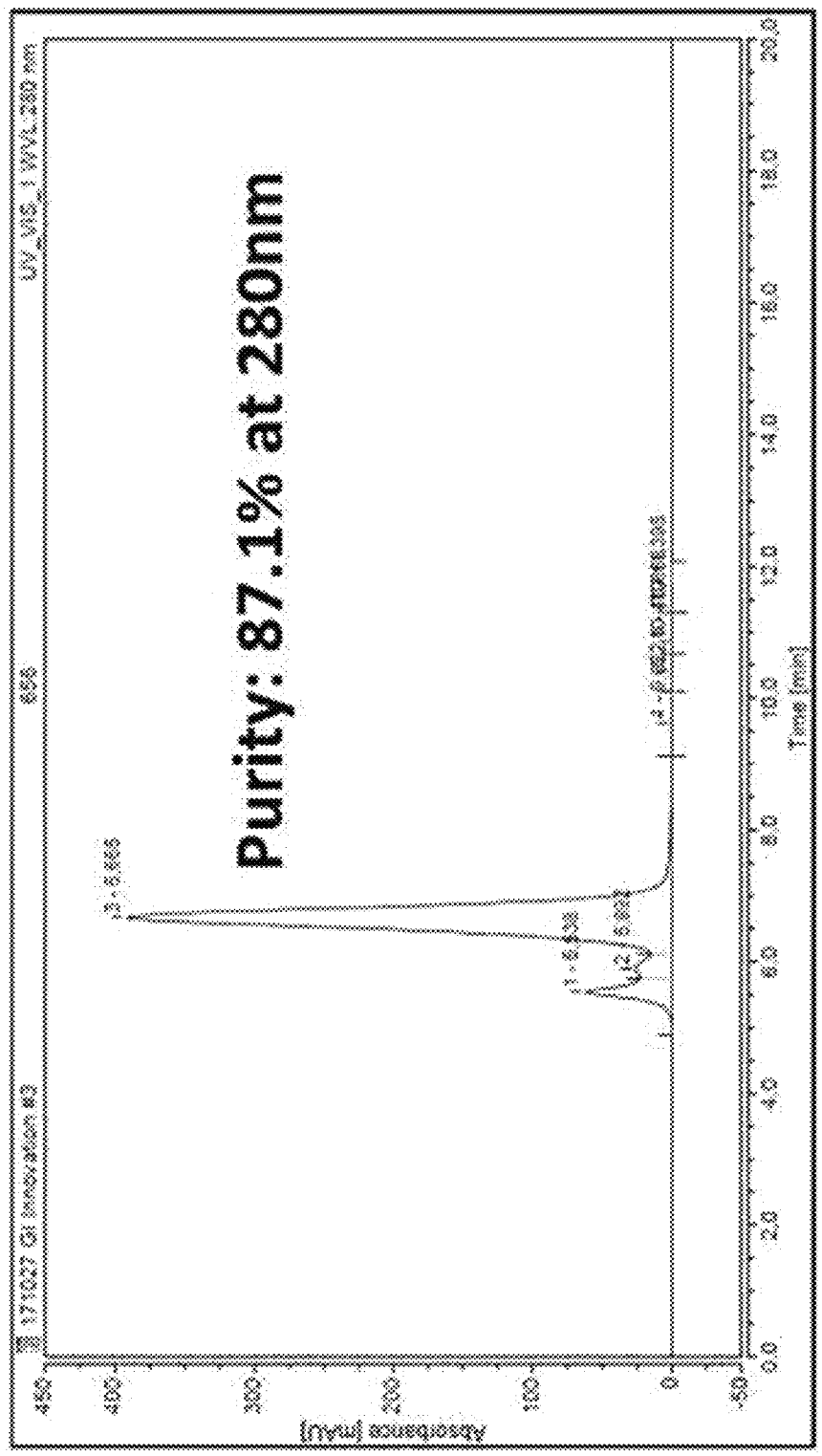
[Fig. 8]

[Fig. 9]
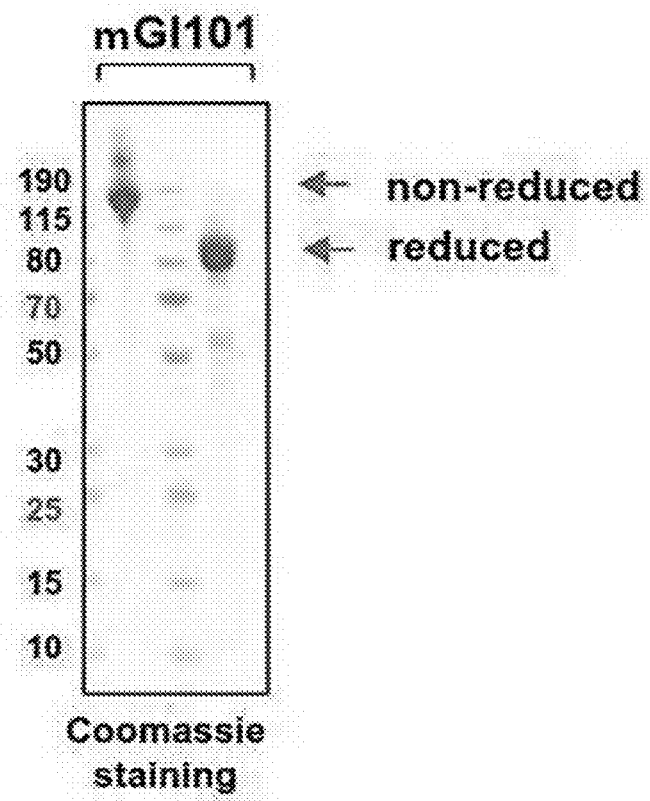
[Fig. 10]
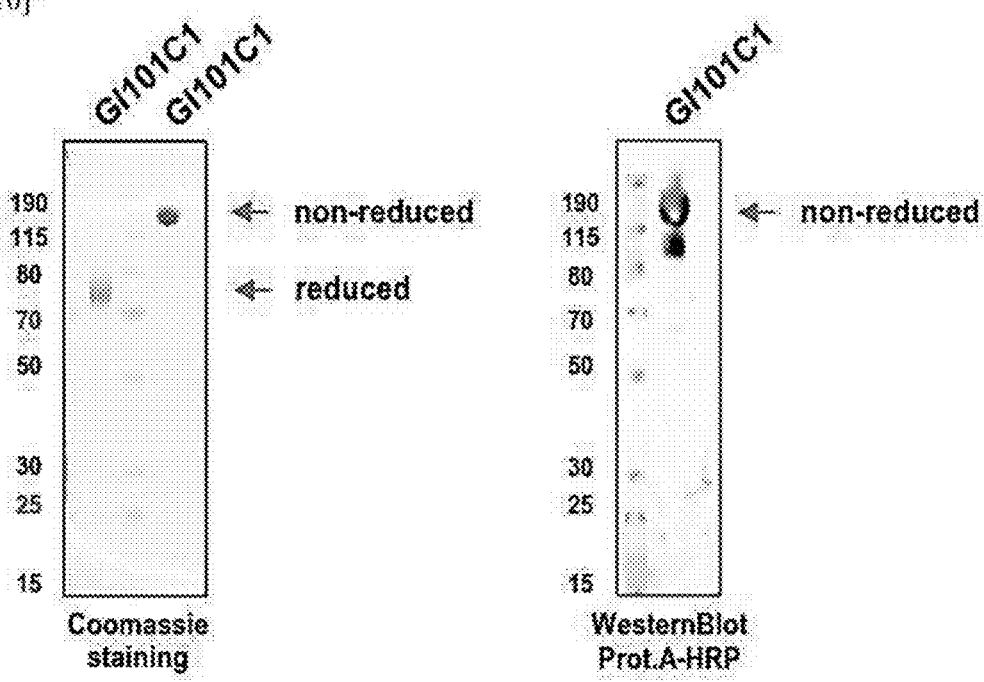

[Fig. 11]
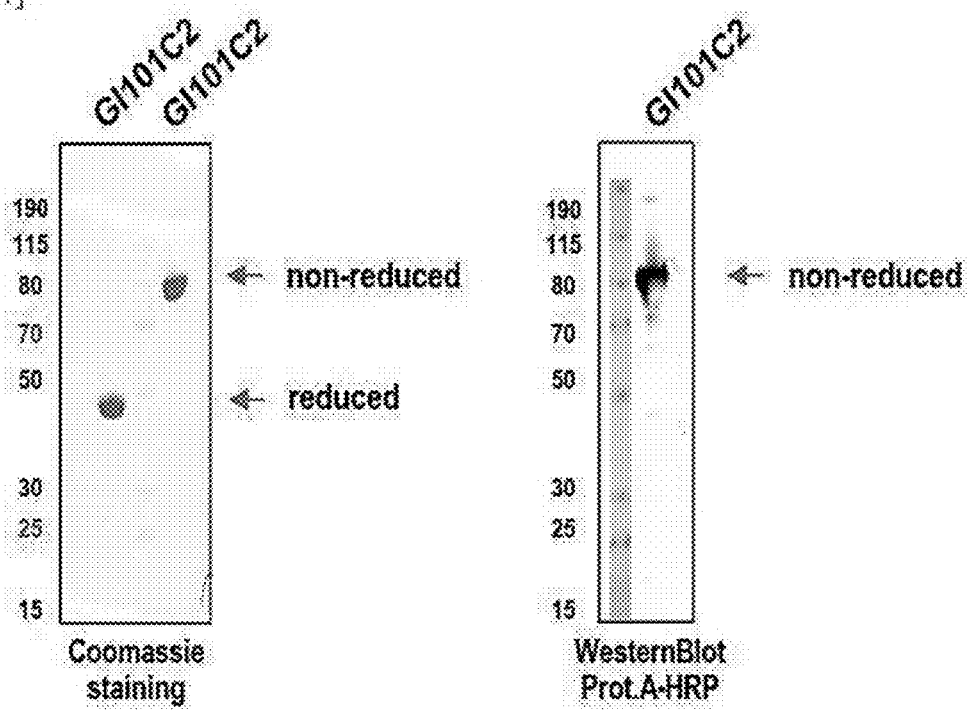
[Fig. 12]
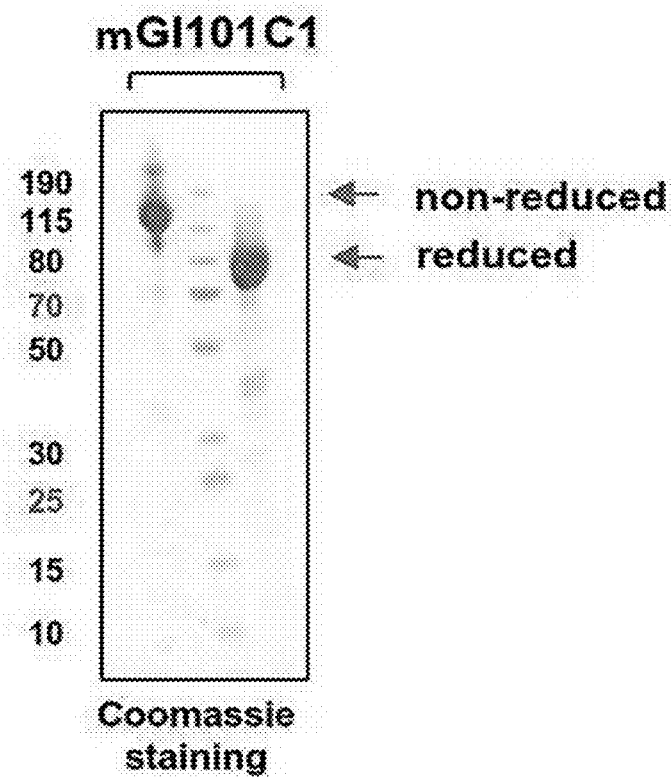

[Fig. 13]
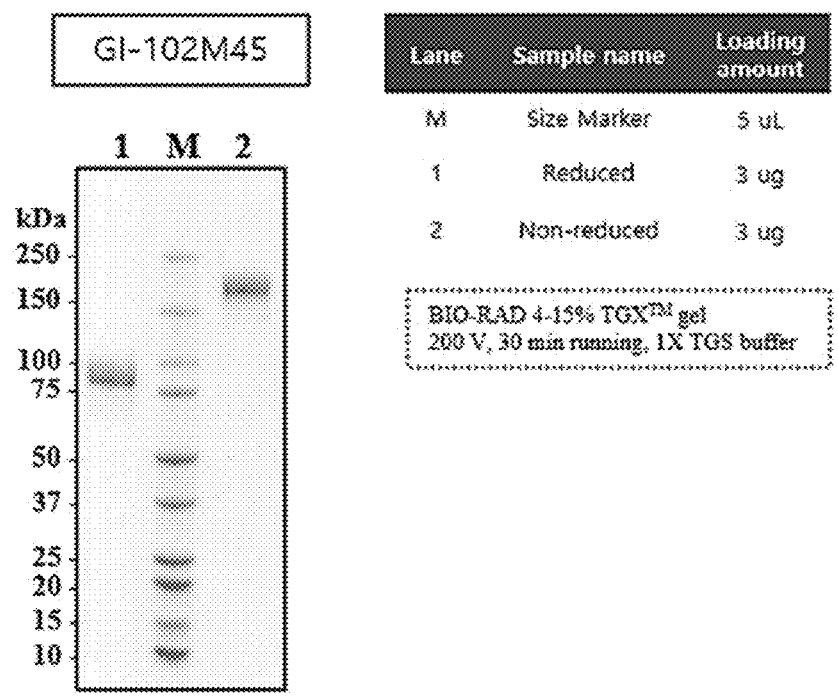
[Fig. 14]
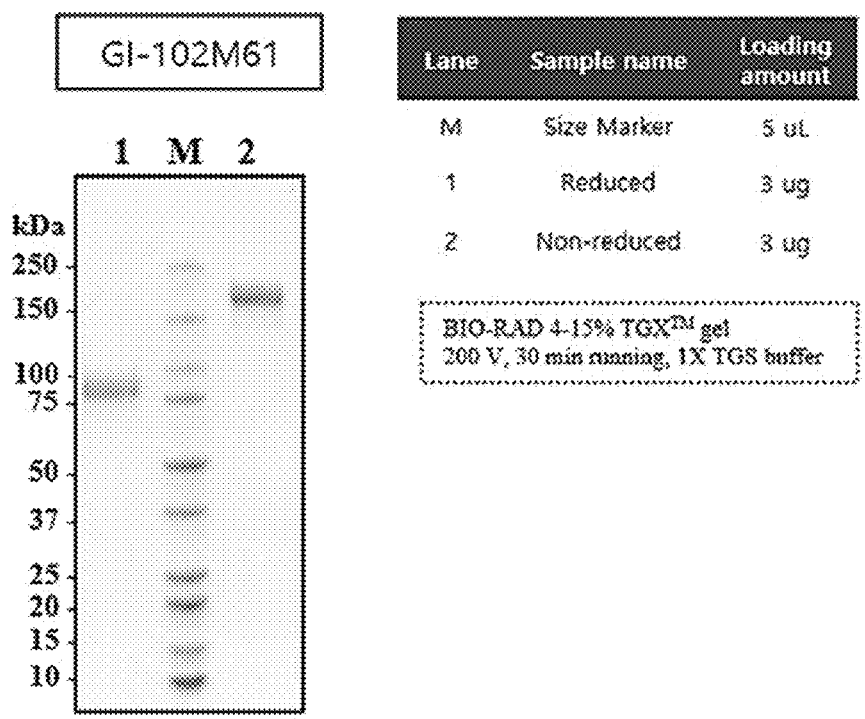

[Fig. 15]
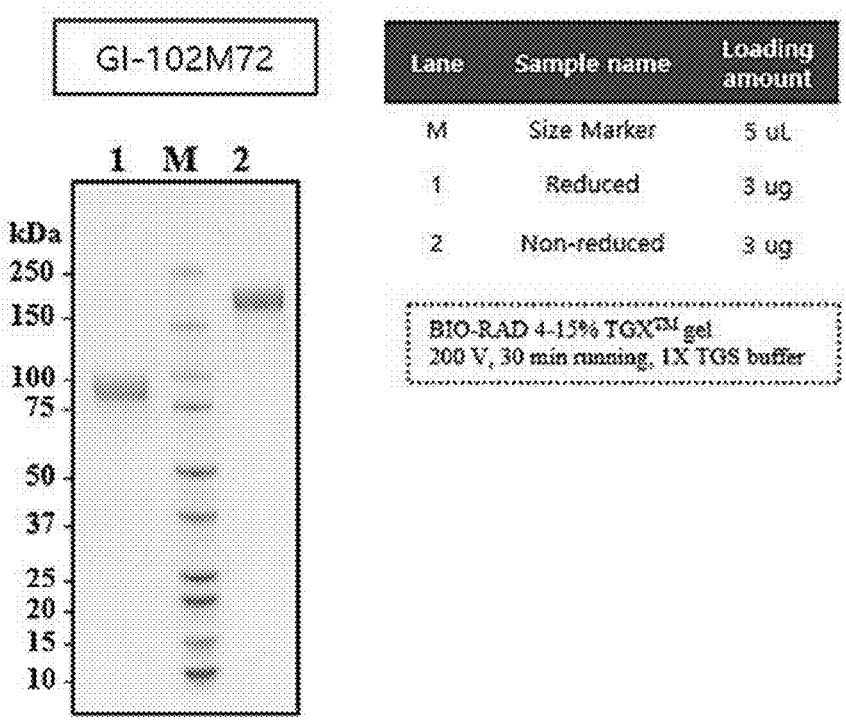
[Fig. 16]
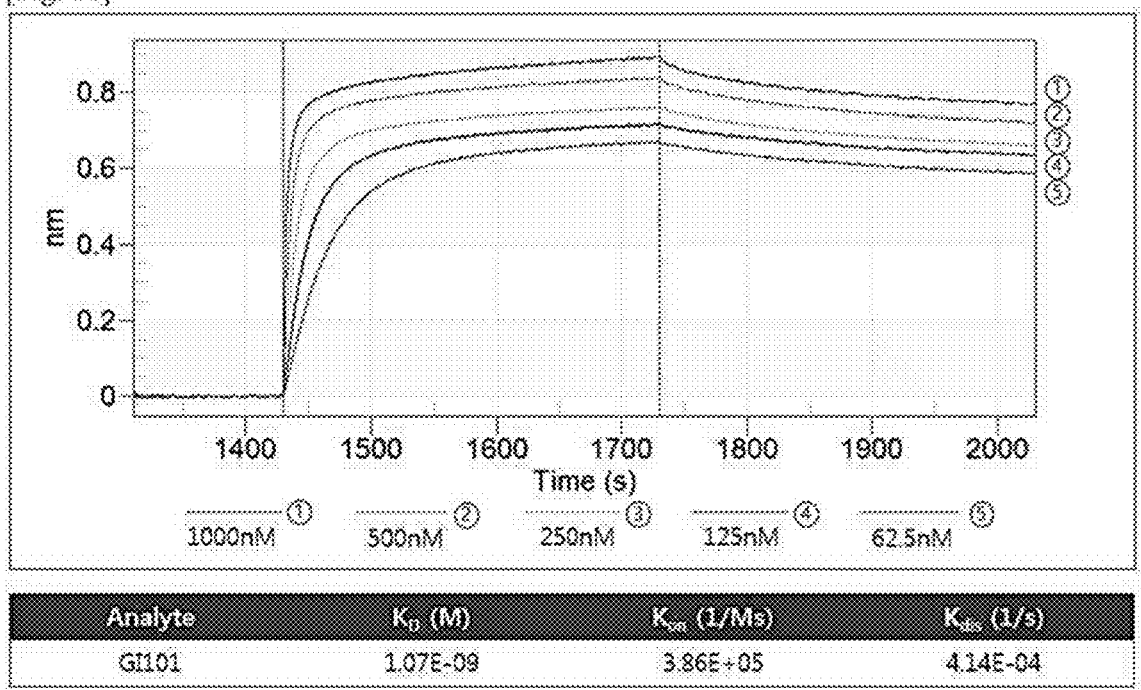

[Fig. 17]
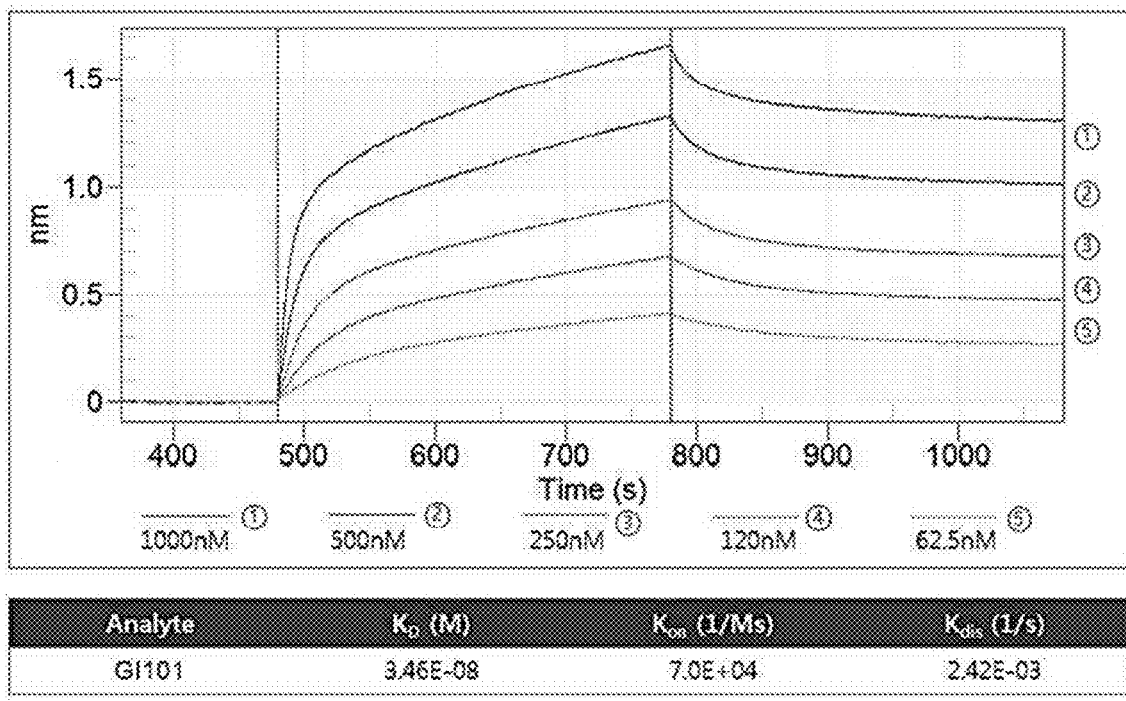
[Fig. 18]
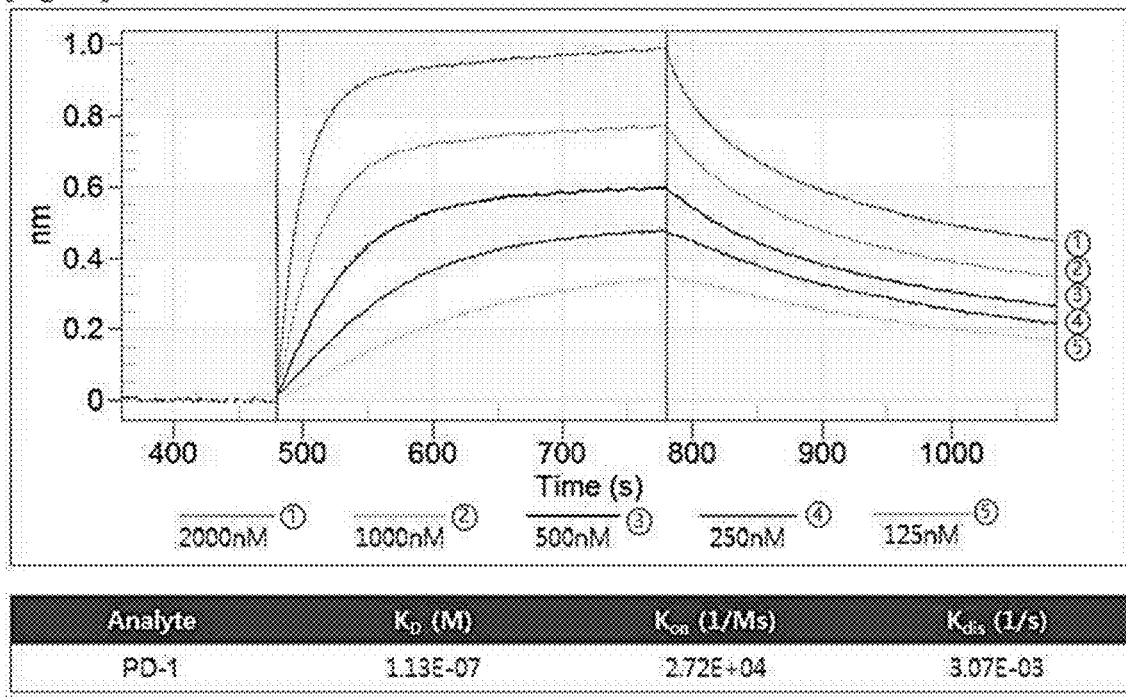

[Fig. 19]
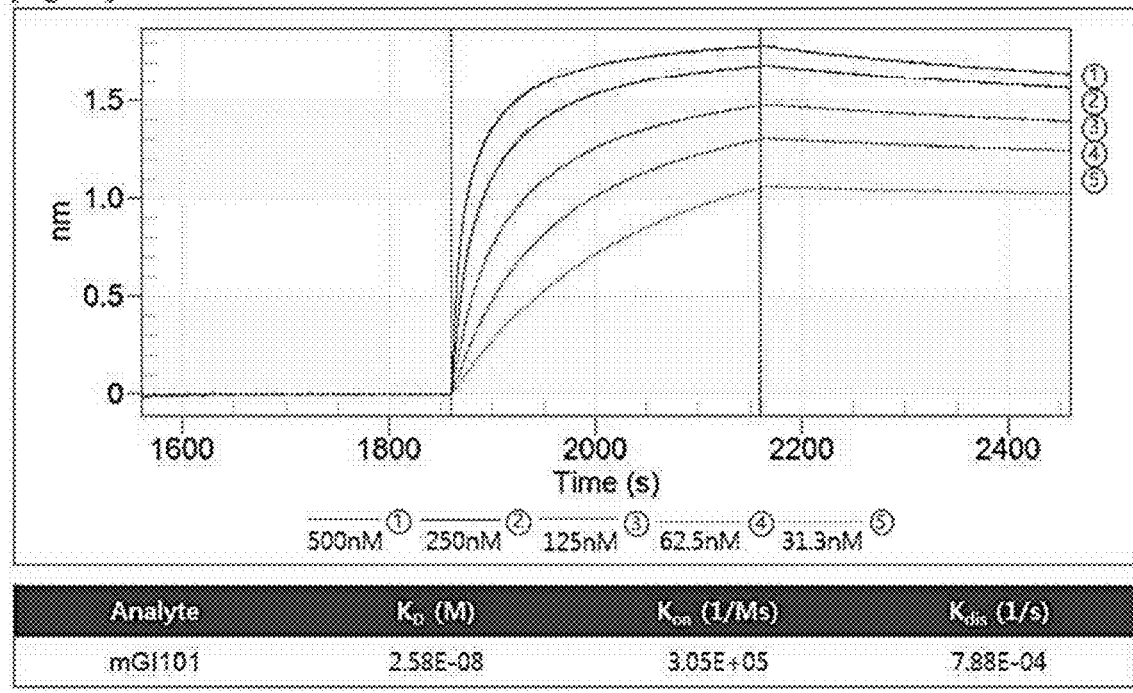
[Fig. 20]
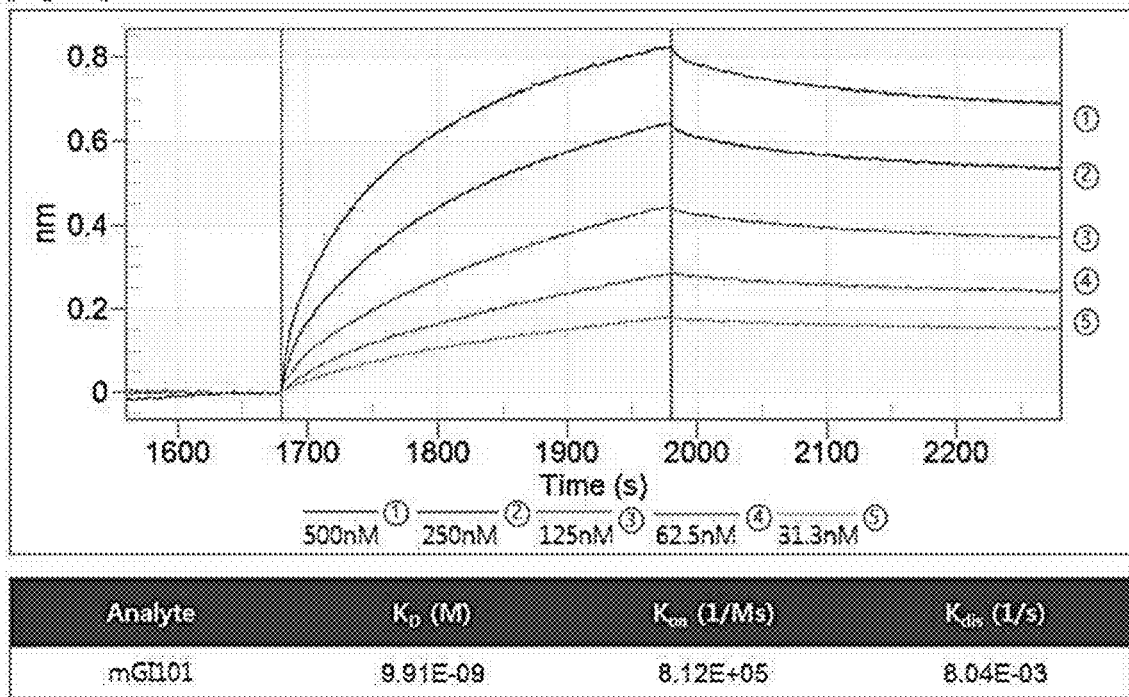

[Fig. 21]
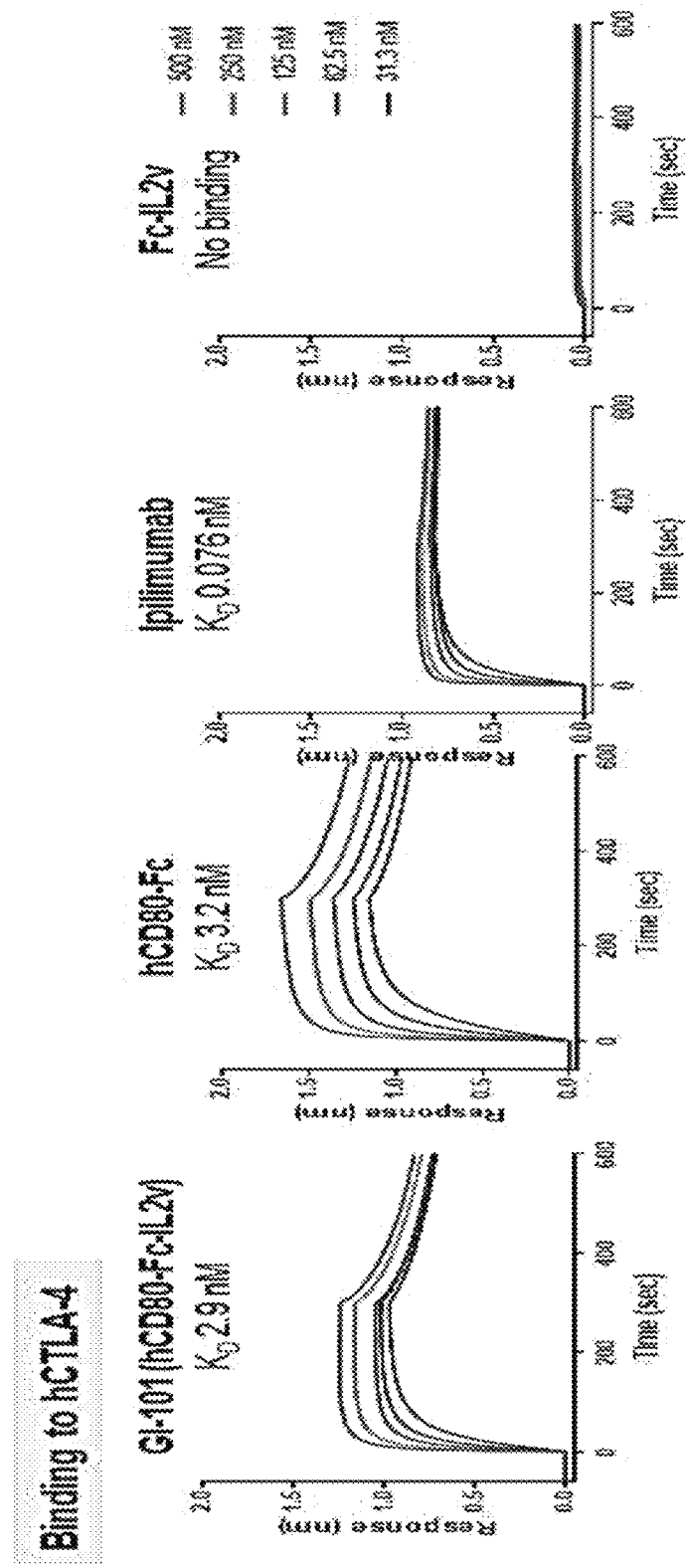

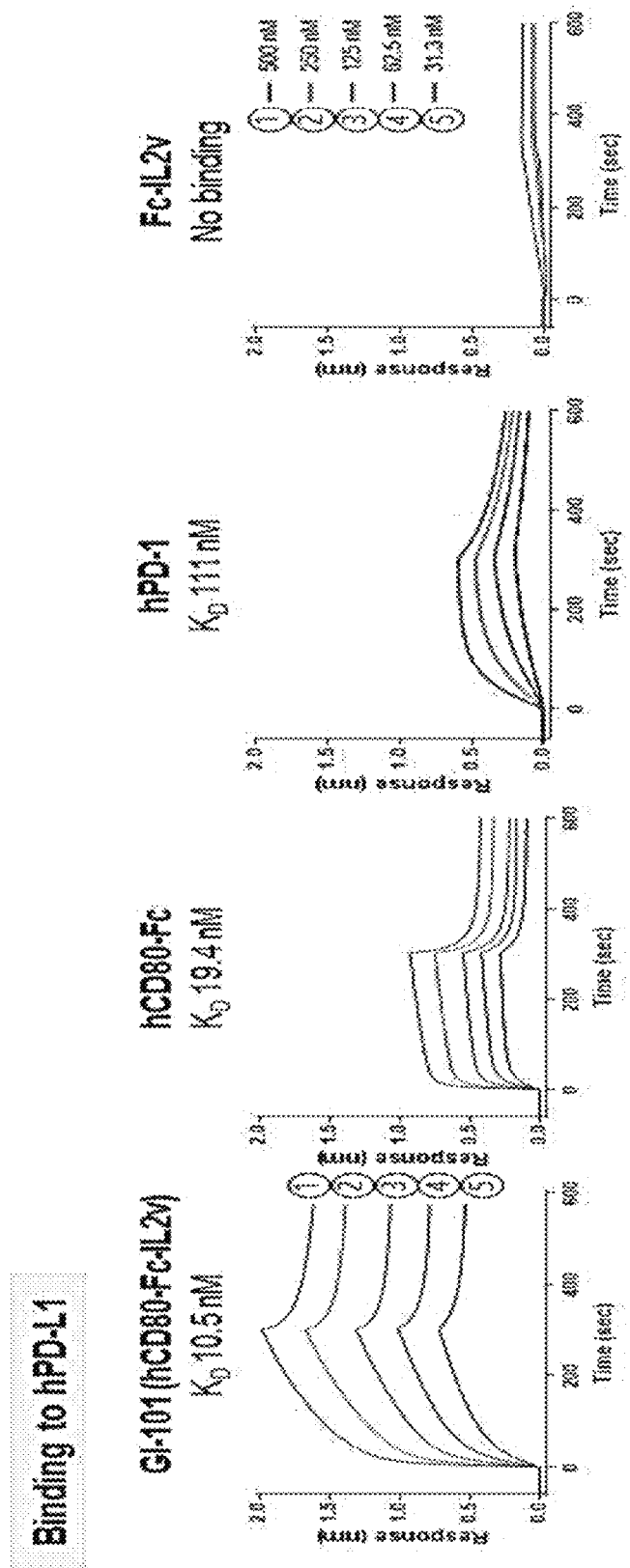
[Fig. 22]

[Fig. 23]
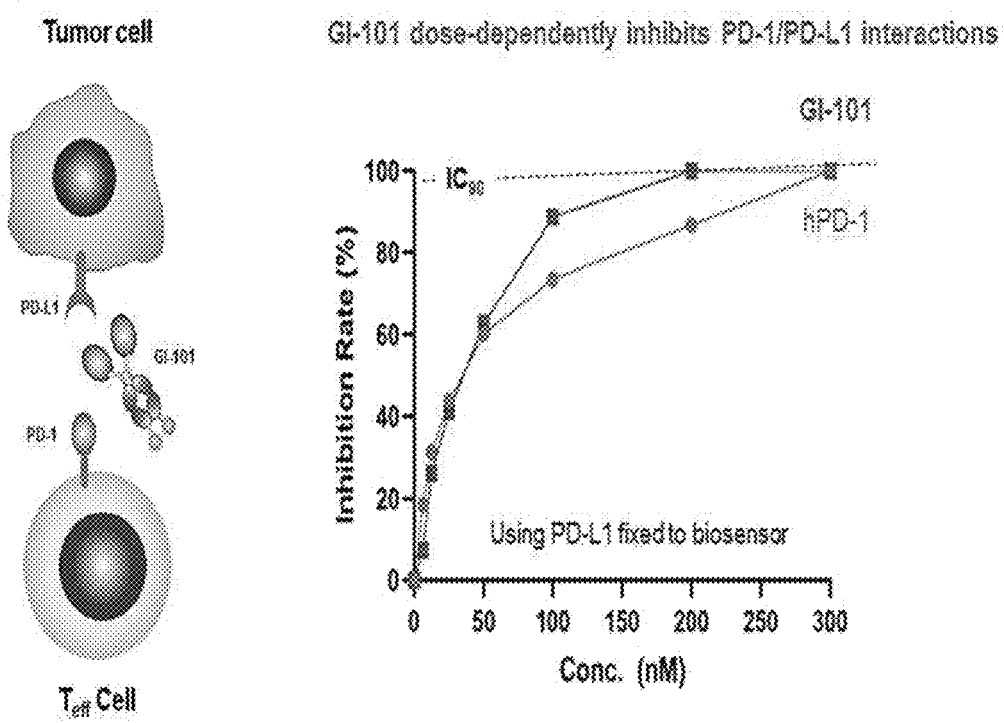

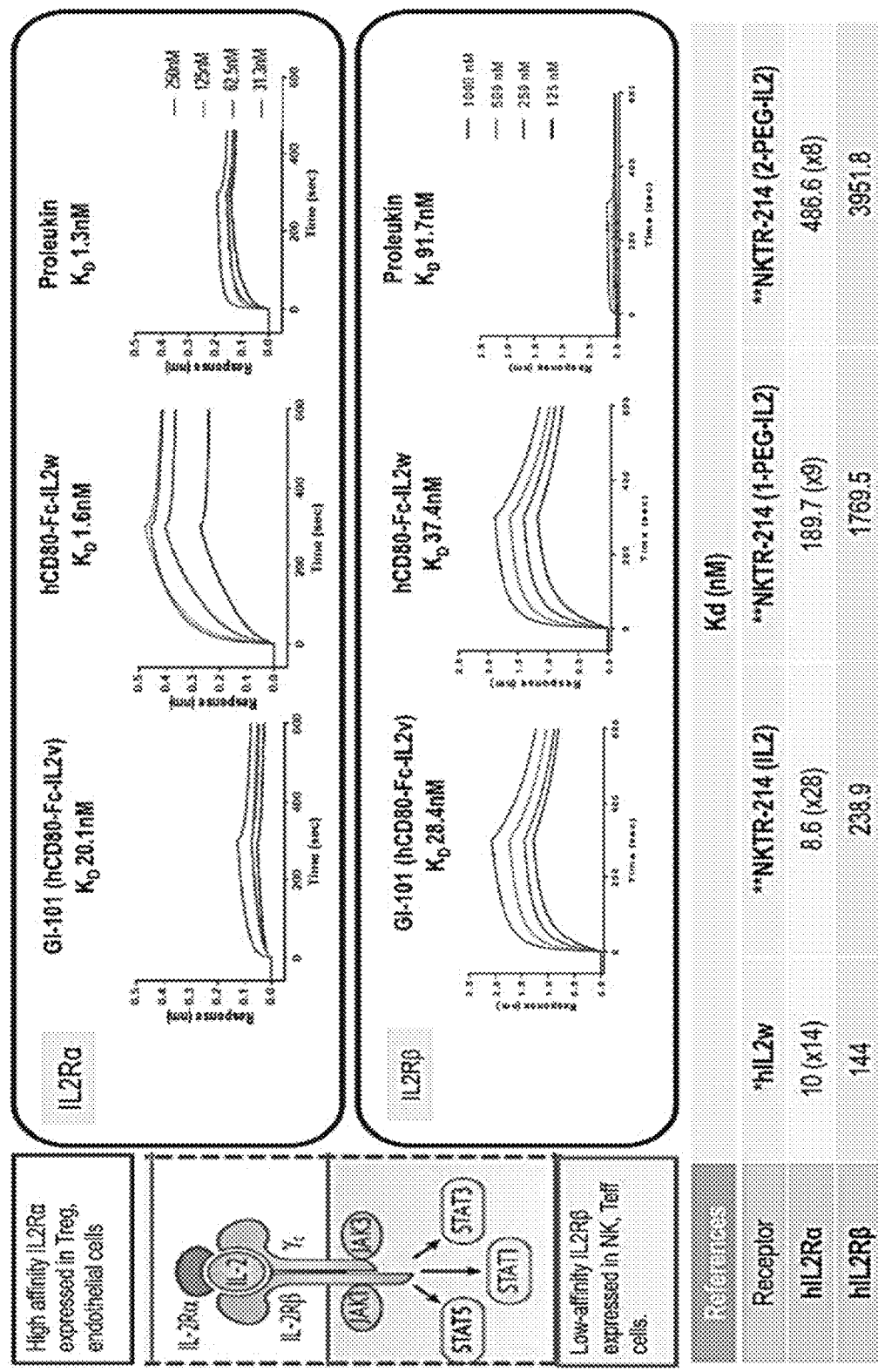
[Fig. 24]

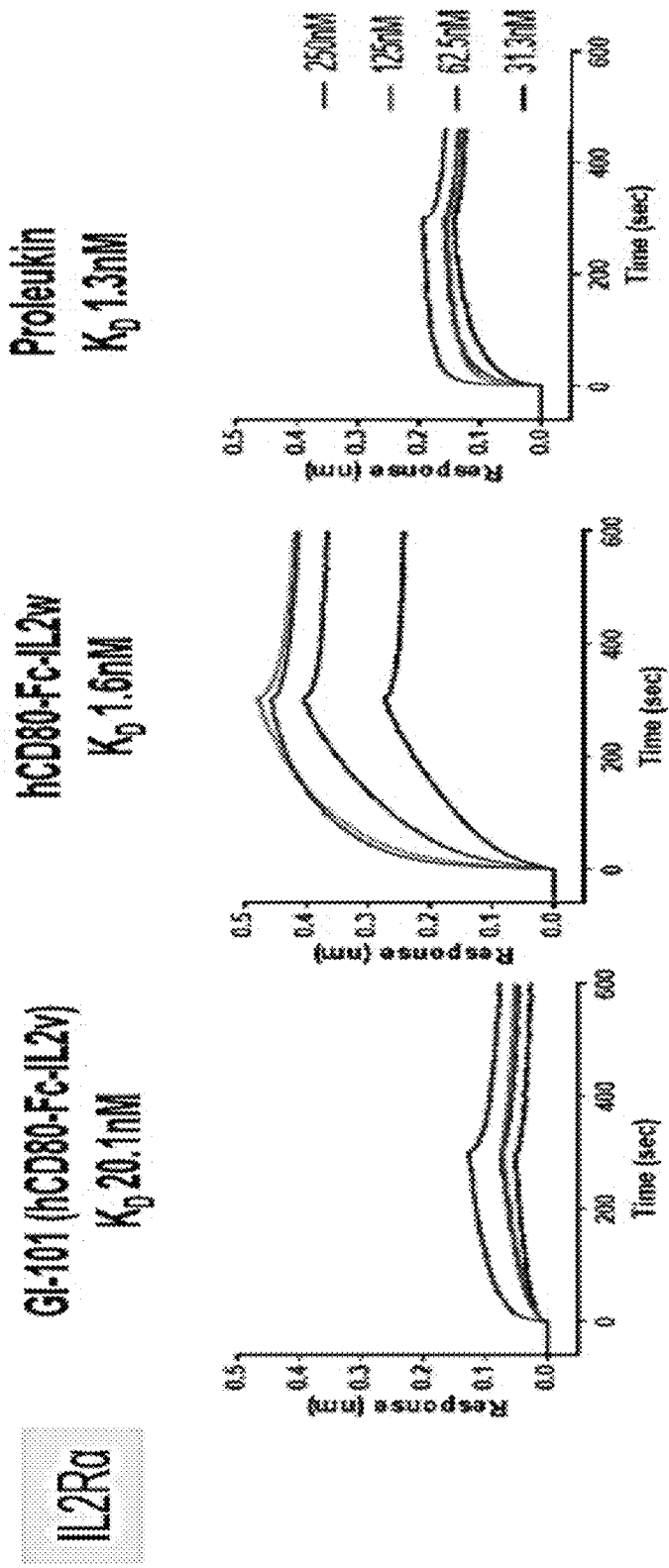
[Fig. 25]

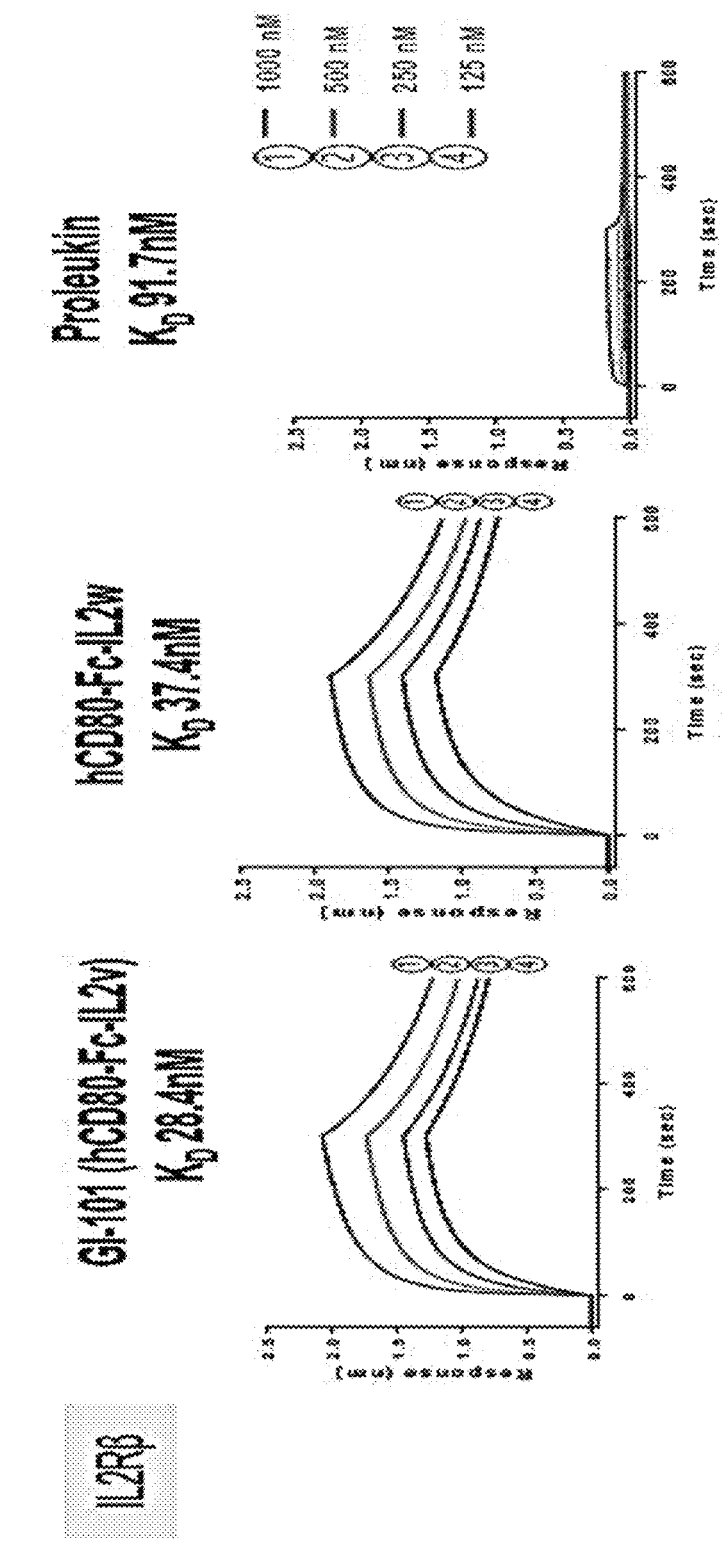
[Fig. 26]

[Fig. 27]
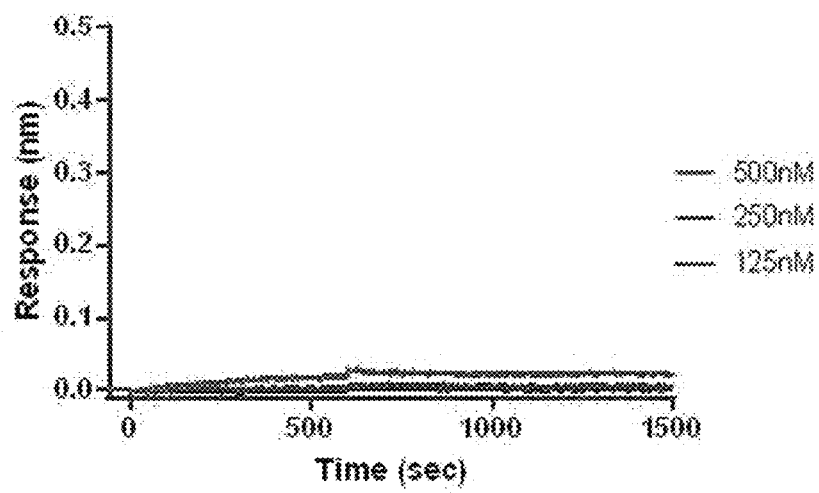
[Fig. 28]
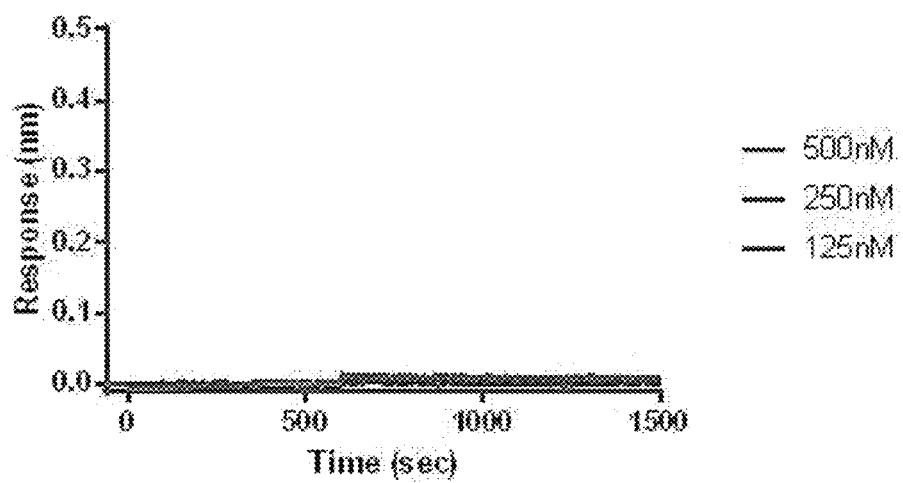

[Fig. 29]
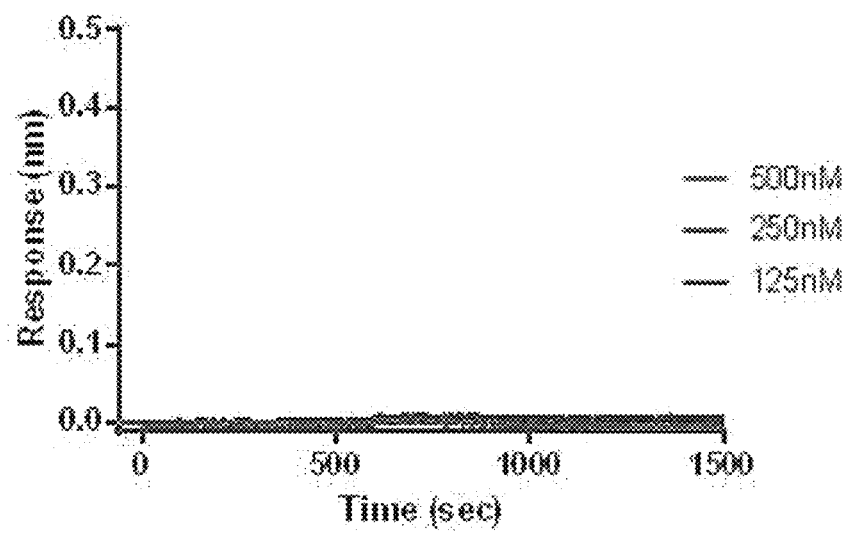
[Fig. 30]
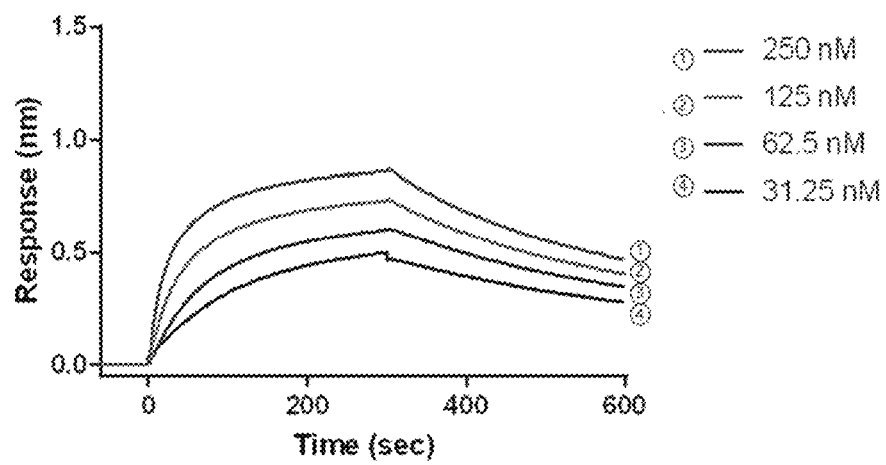
| Kon | Koff | Kd |
|---|---|---|
| 1.30X105 | 2.01X10-3 | 1.55X10-8 |

[Fig. 31]
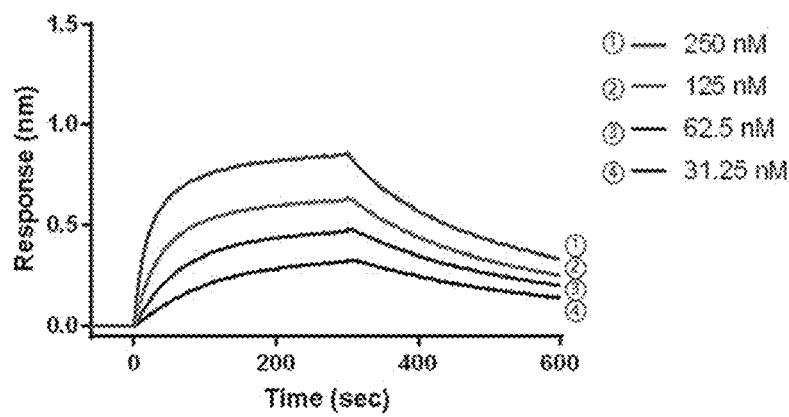
| Kon | Koff | Kd |
|---|---|---|
| 1.32X105 | 3.11X10-3 | 2.36X10-8 |
[Fig. 32]
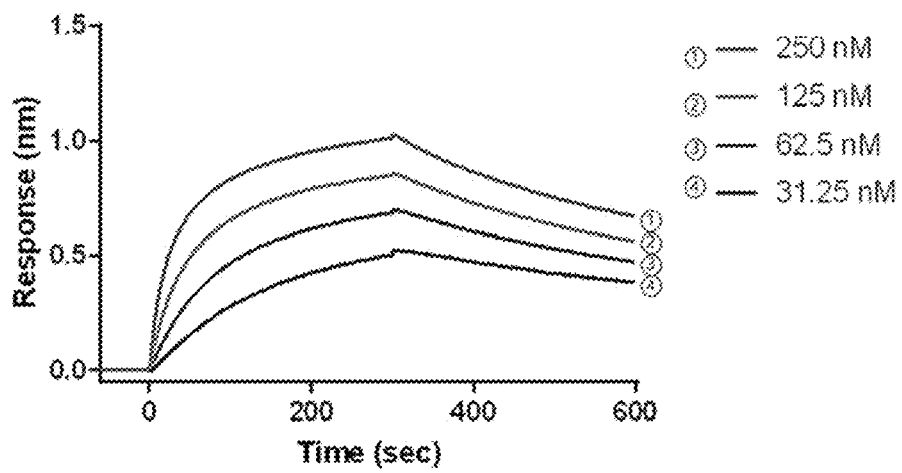
| Kon | Koff | Kd |
|---|---|---|
| 1.10X105 | 1.27X10-3 | 1.15X10-8 |

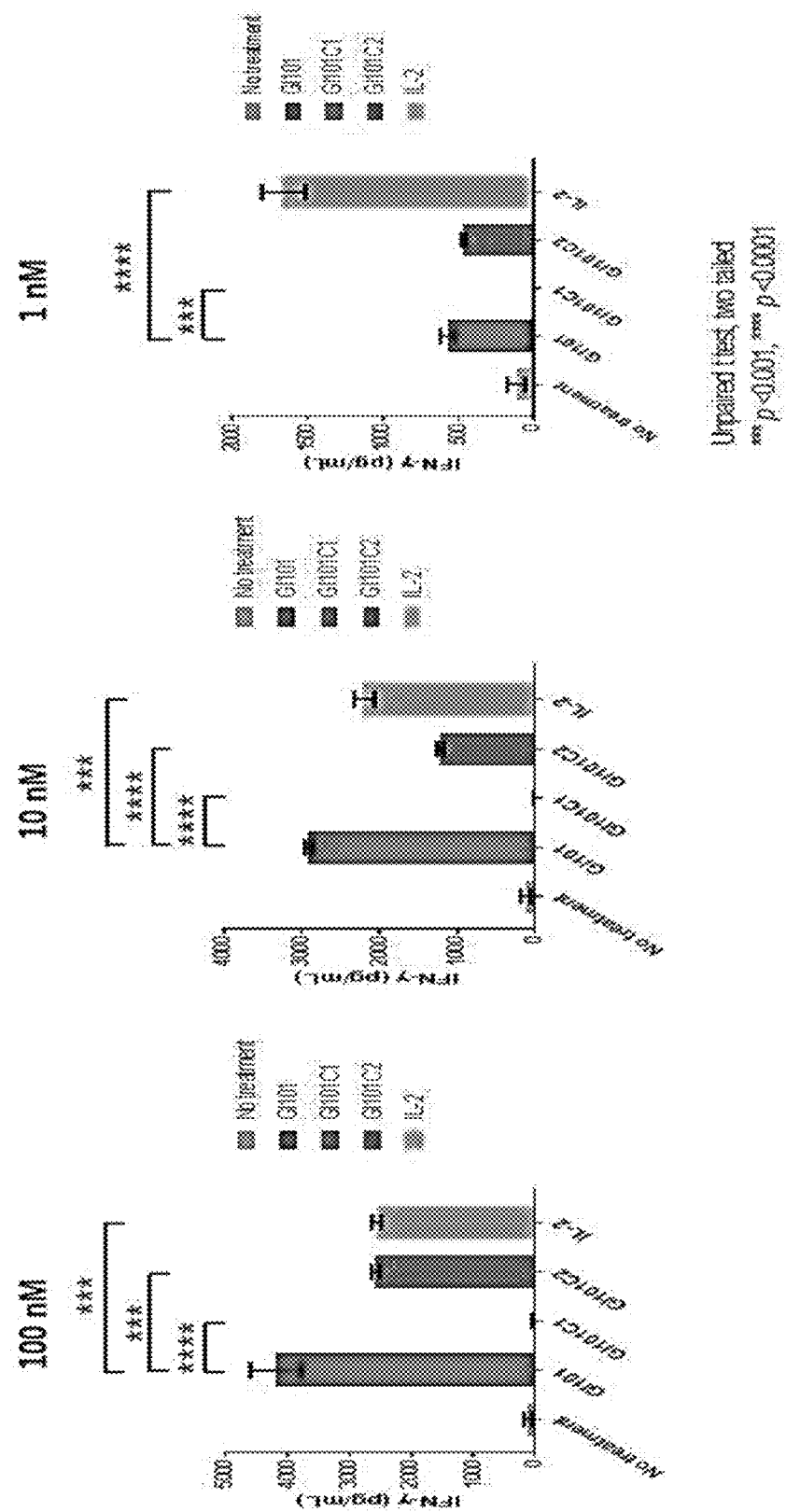
[Fig. 33]

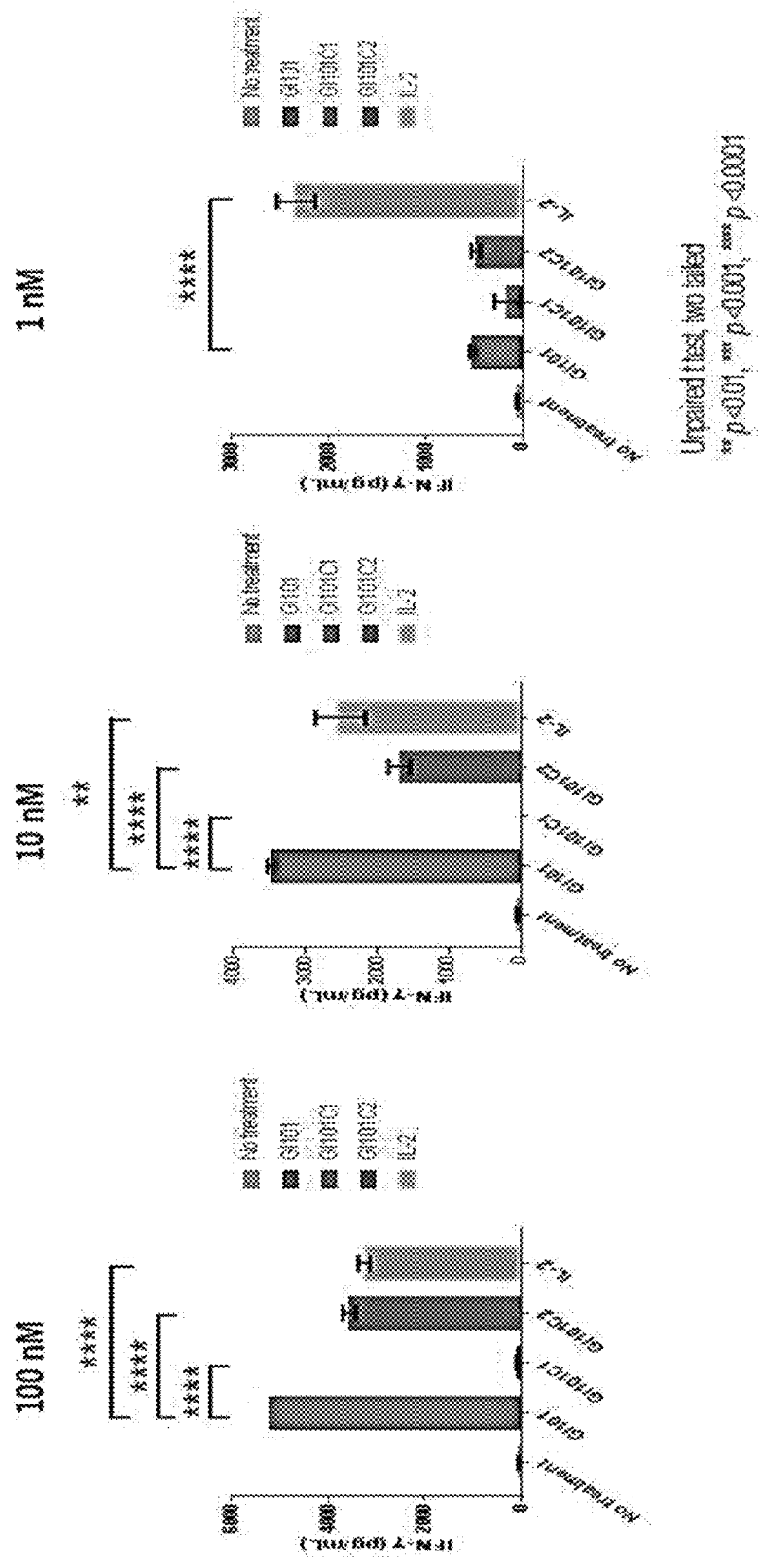
[Fig. 34]

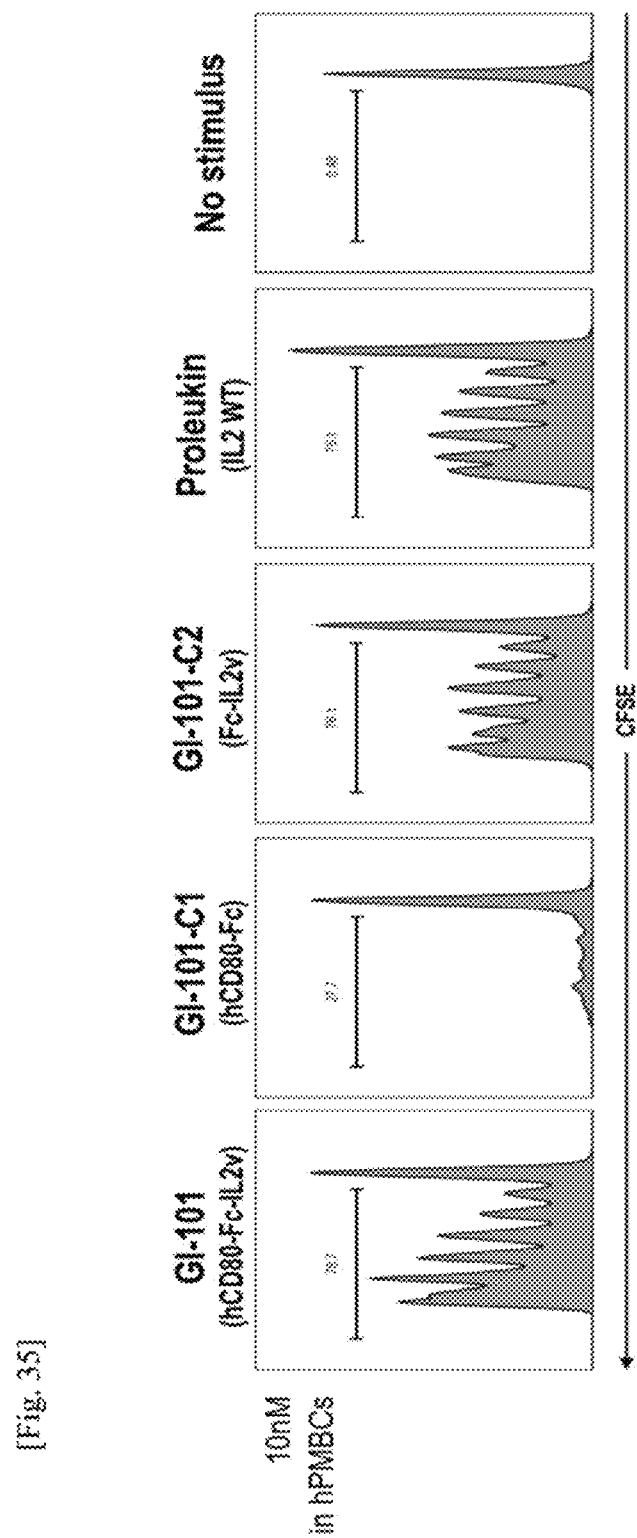
[Fig. 35]

[Fig. 36]
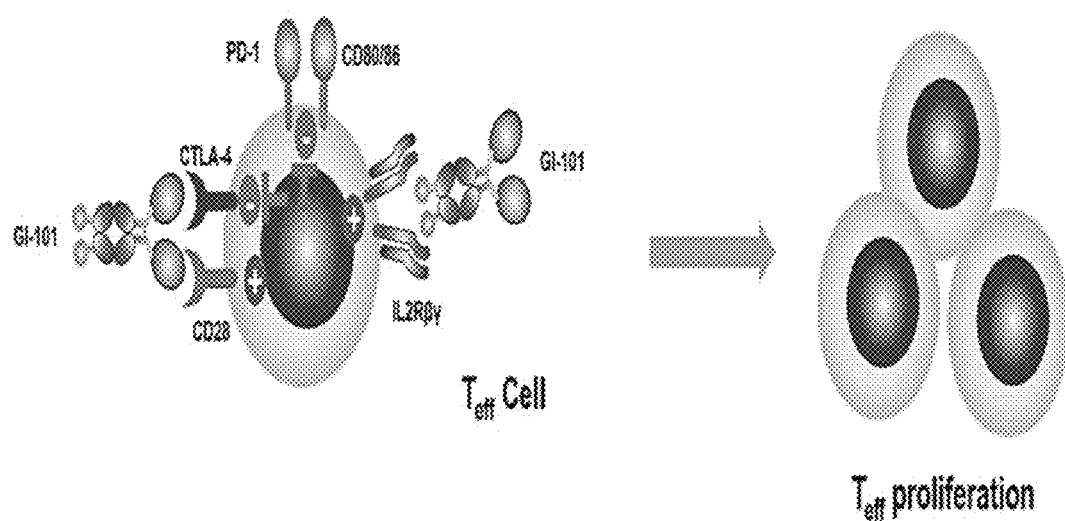

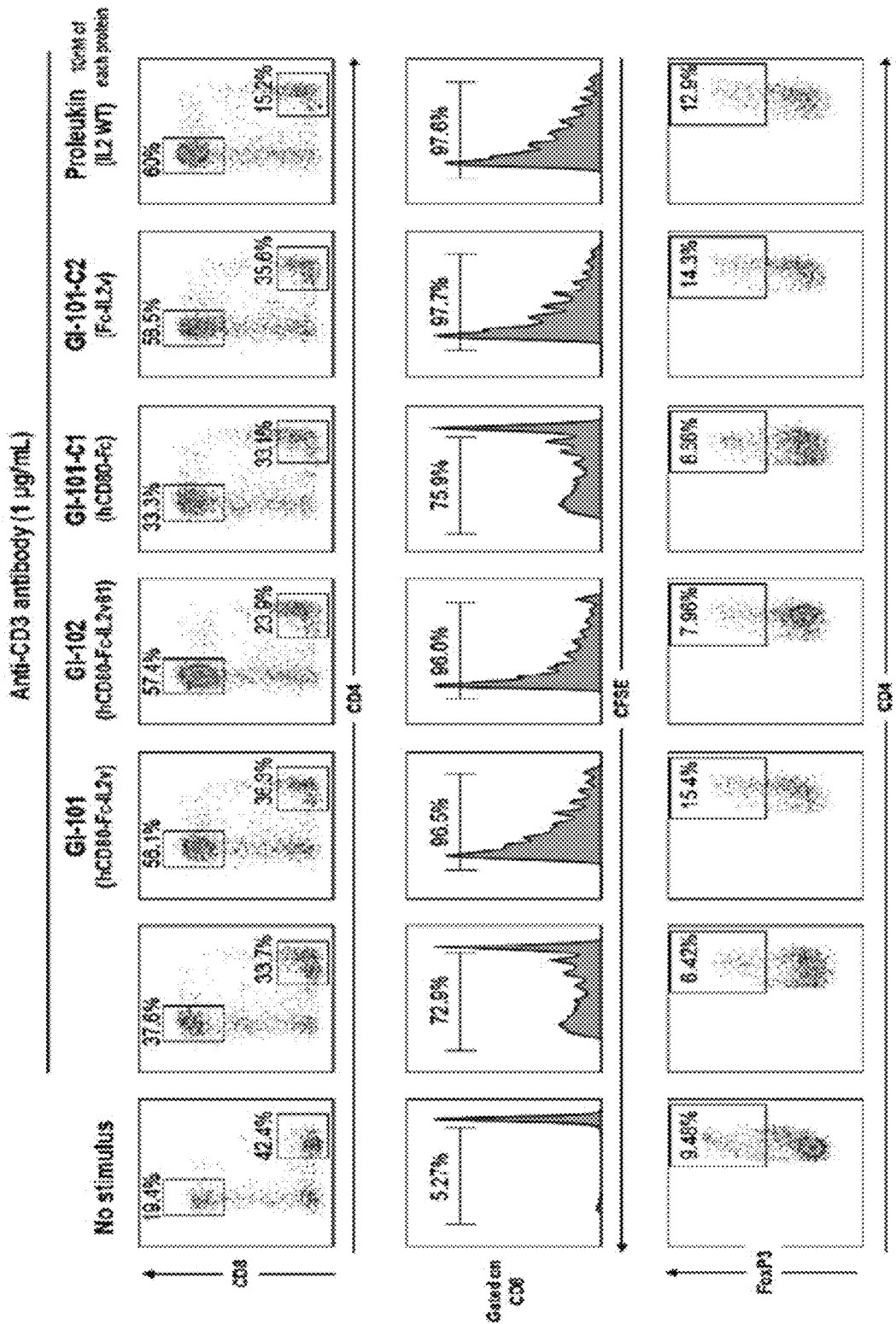
[Fig. 37]

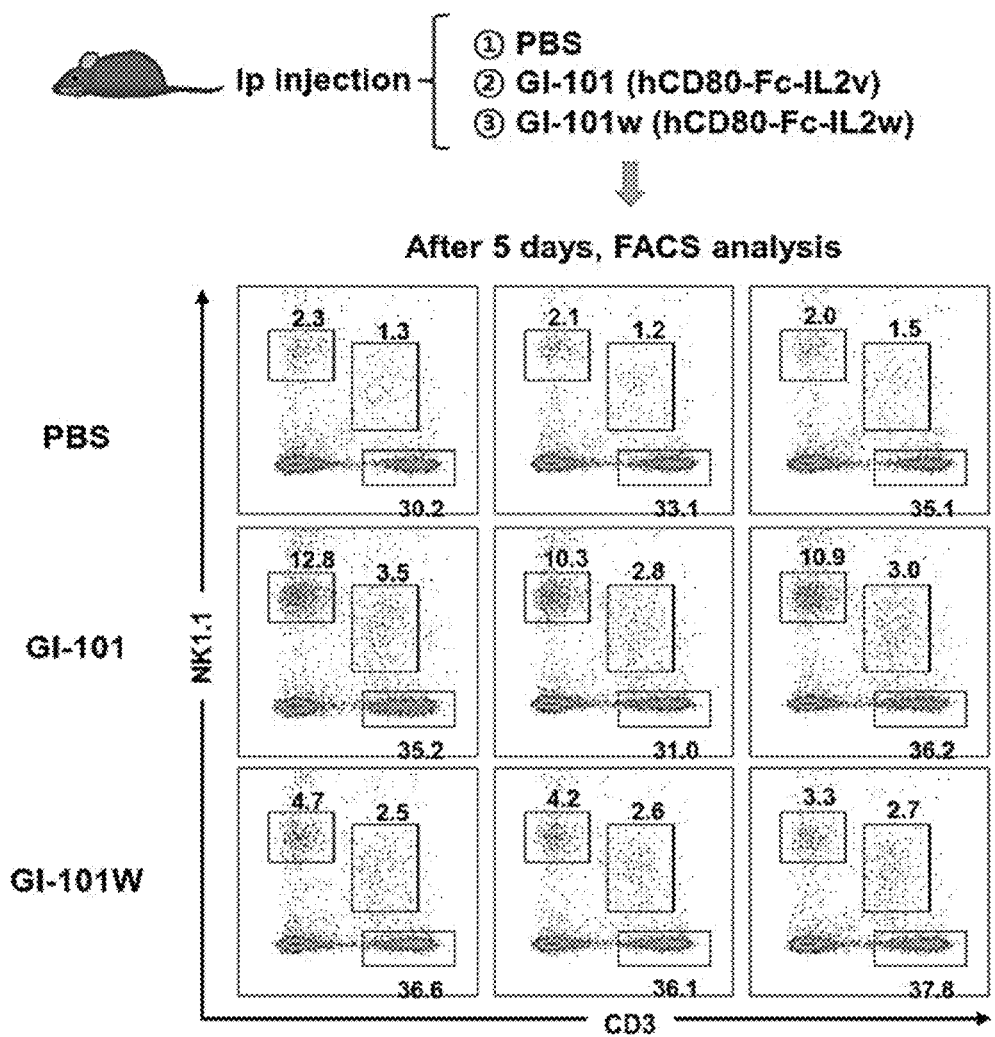
[Fig. 38]

[Fig. 39]
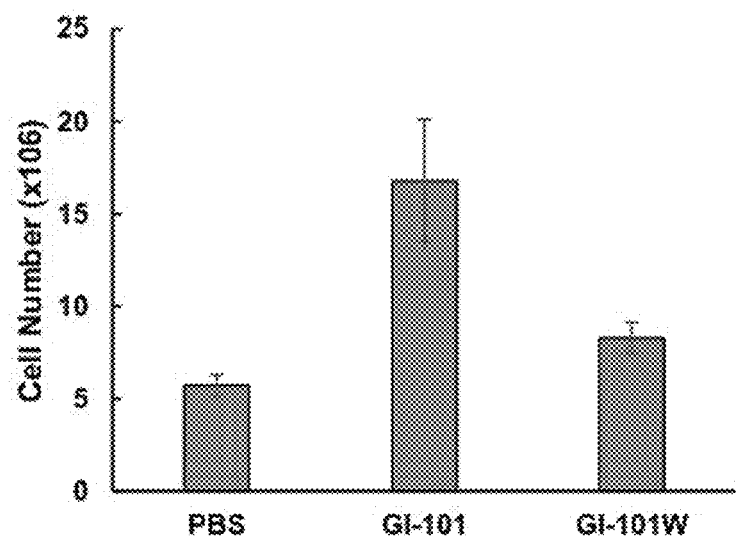
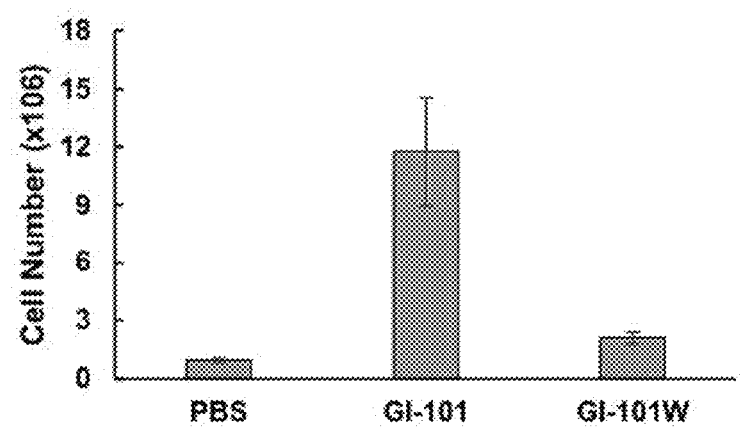

[Fig. 40]
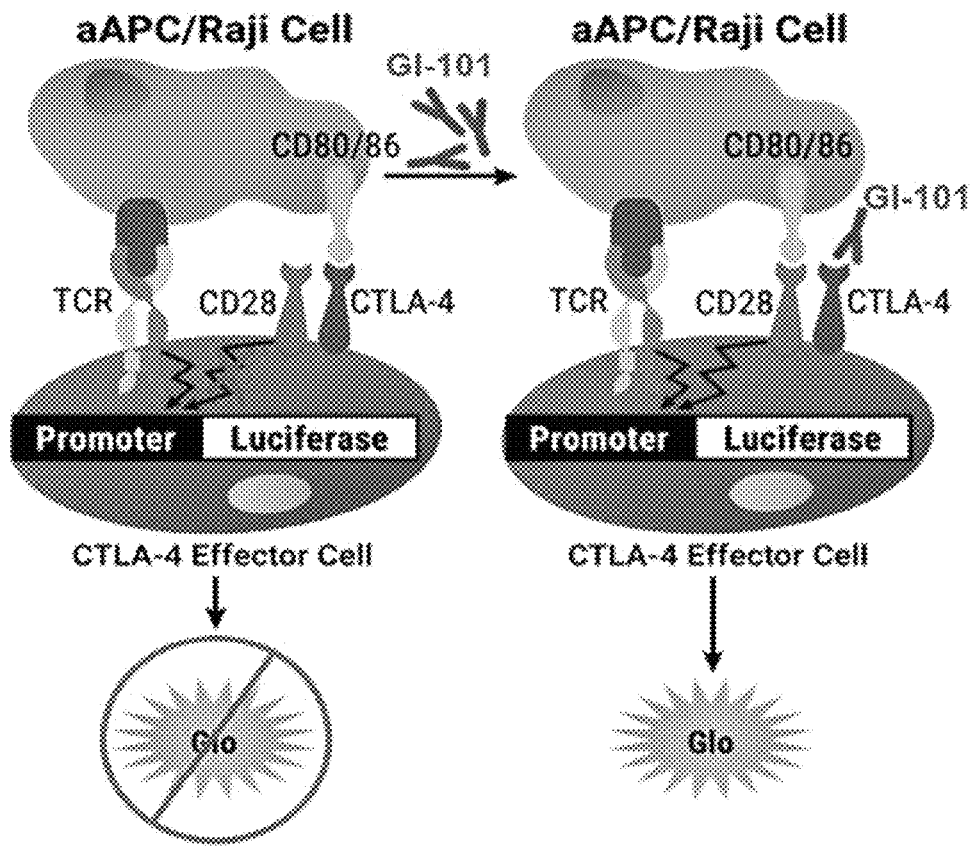
[Fig. 41]
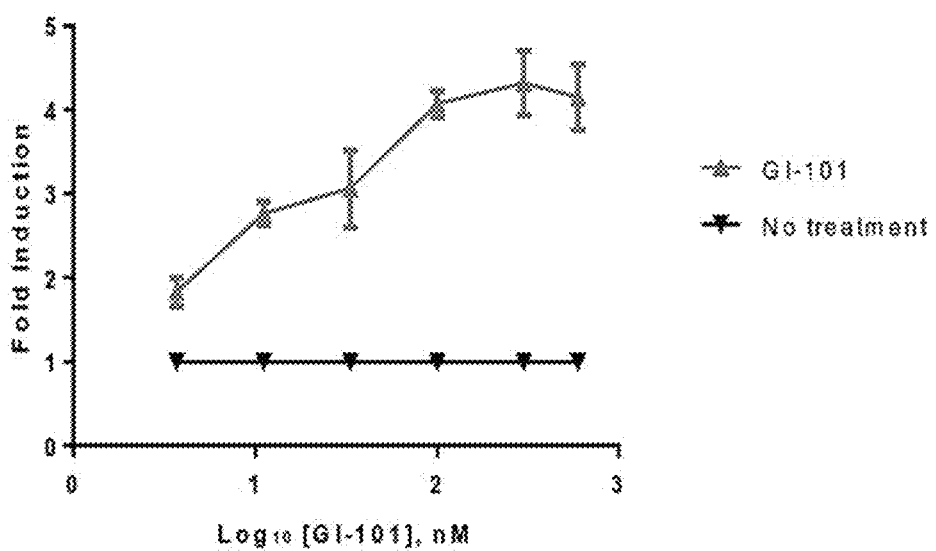

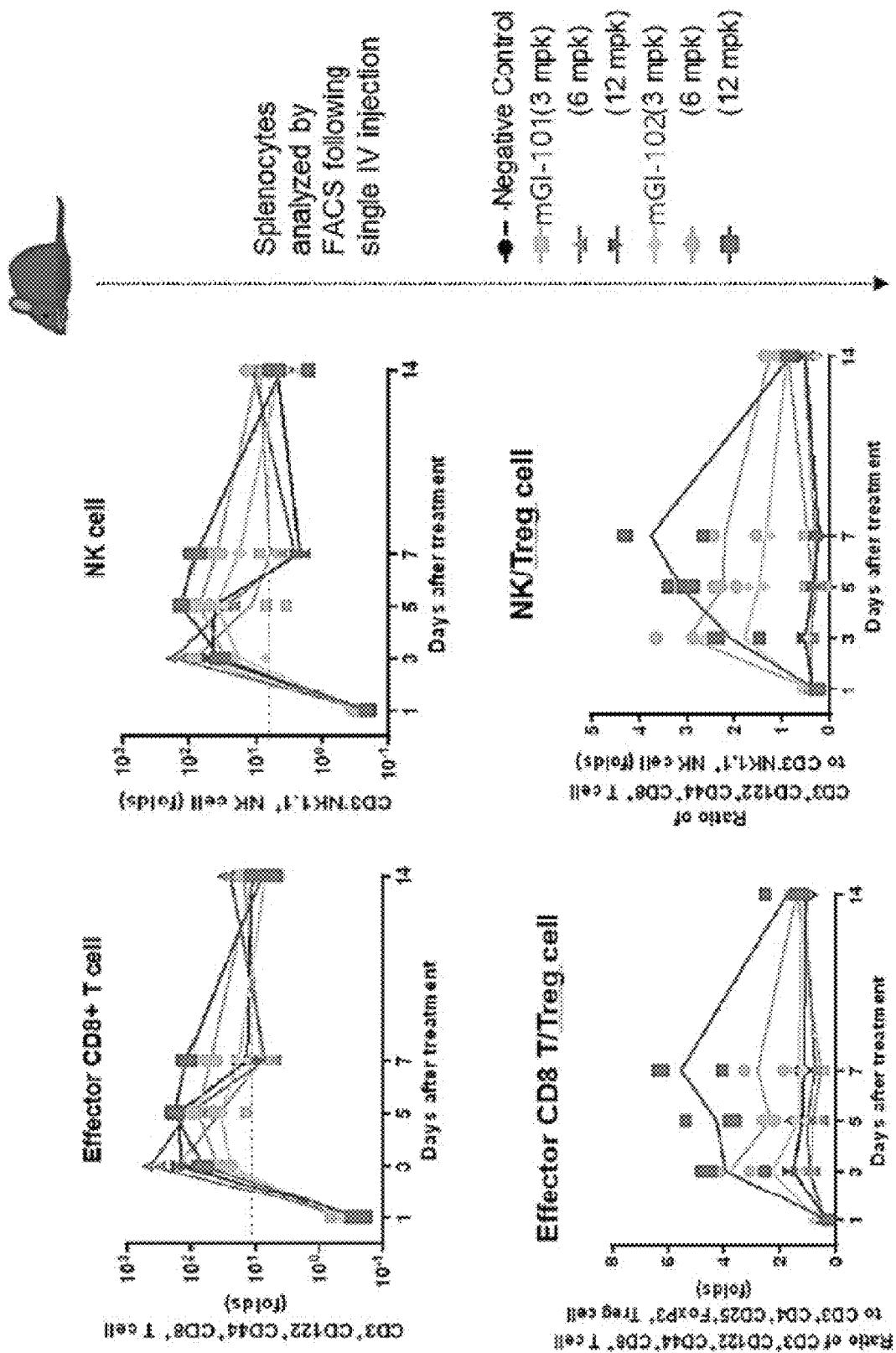
[Fig. 42]

[Fig. 43]
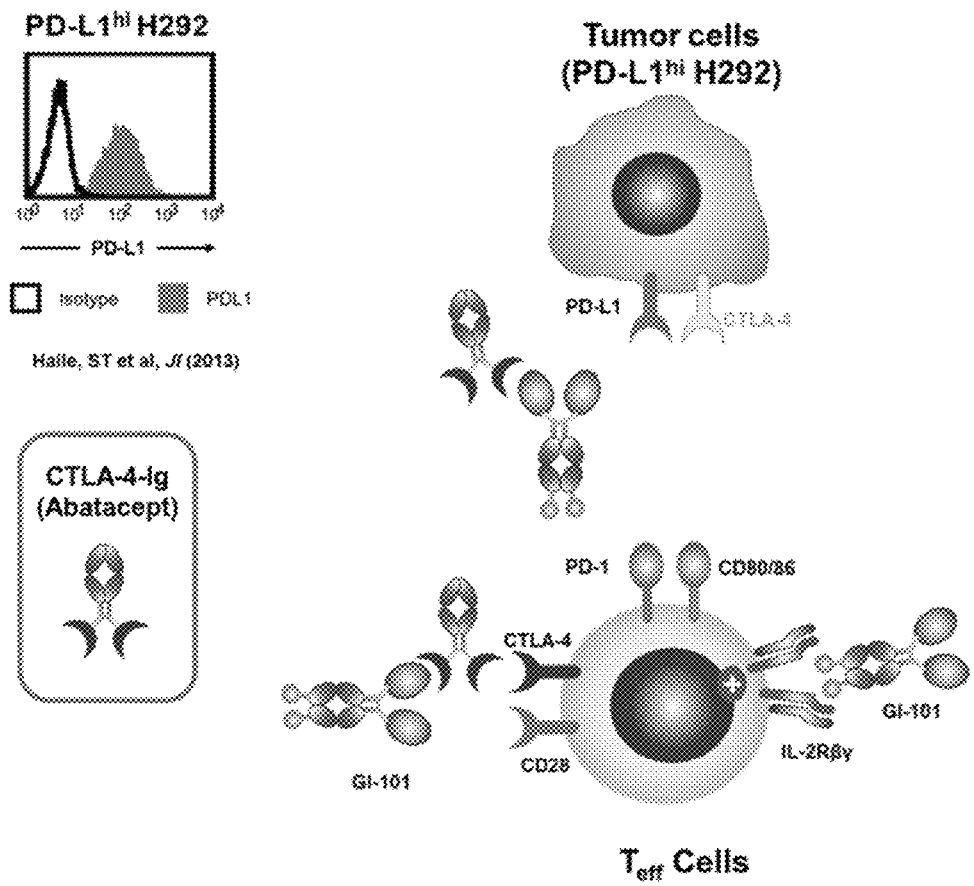
[Fig. 44]
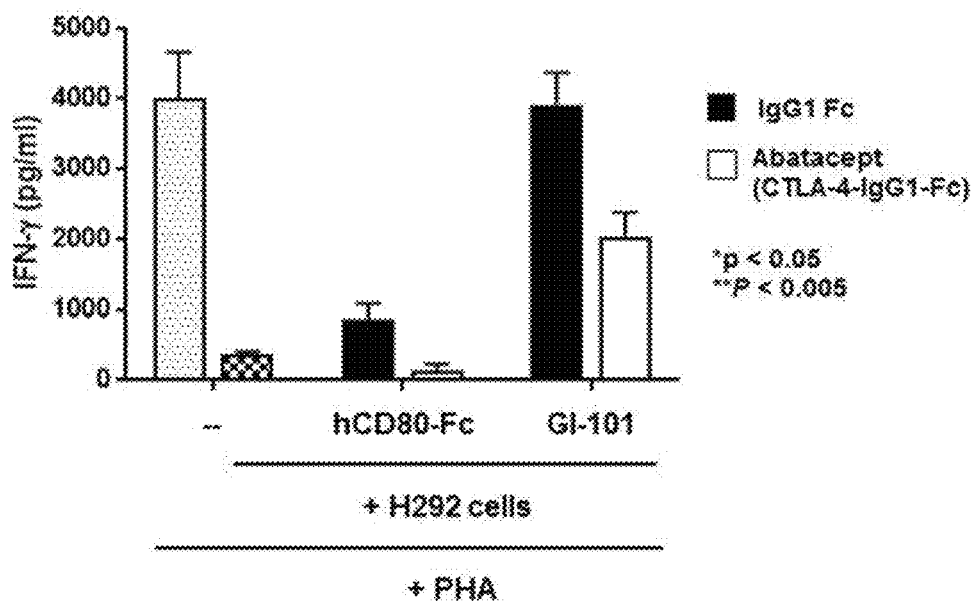

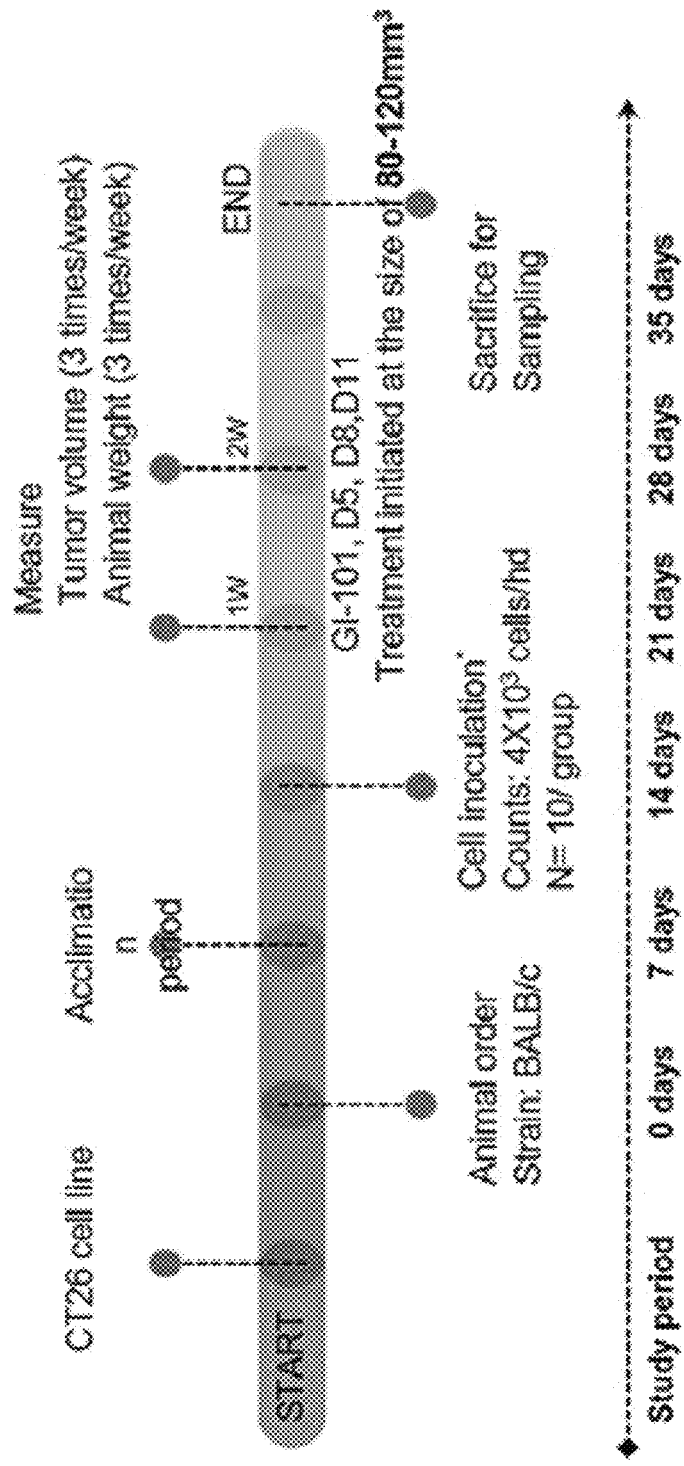
[Fig. 45]

[Fig. 46]
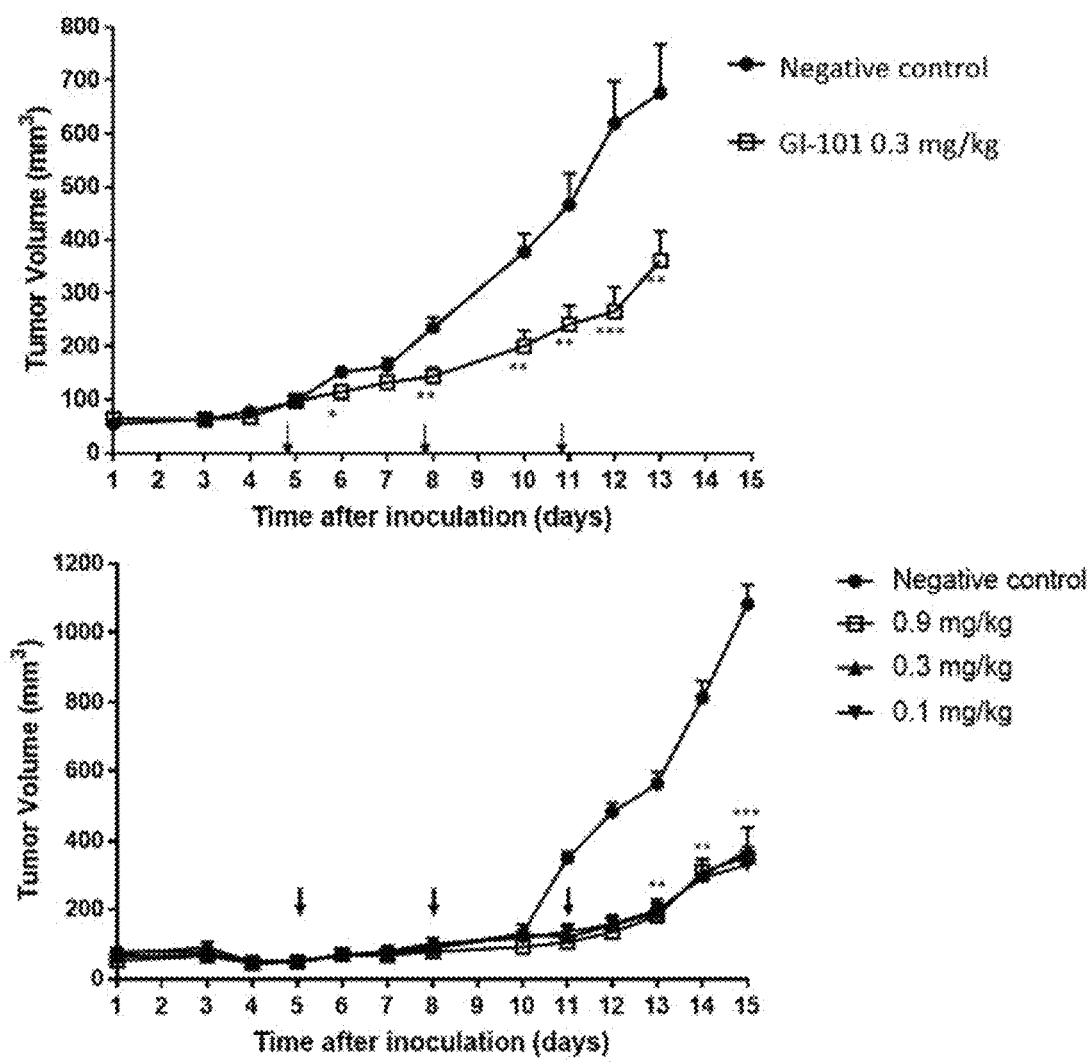
* p<0.05,  p<0.005, * p<0.001
Each point represents mean + SE (n=10)

[Fig. 47]
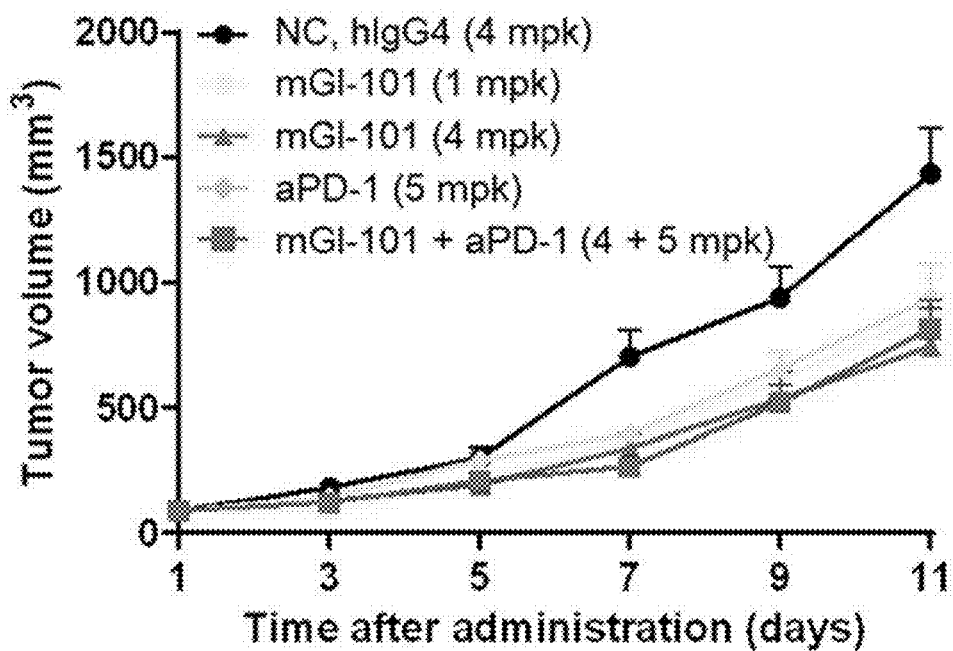
[Fig. 48]
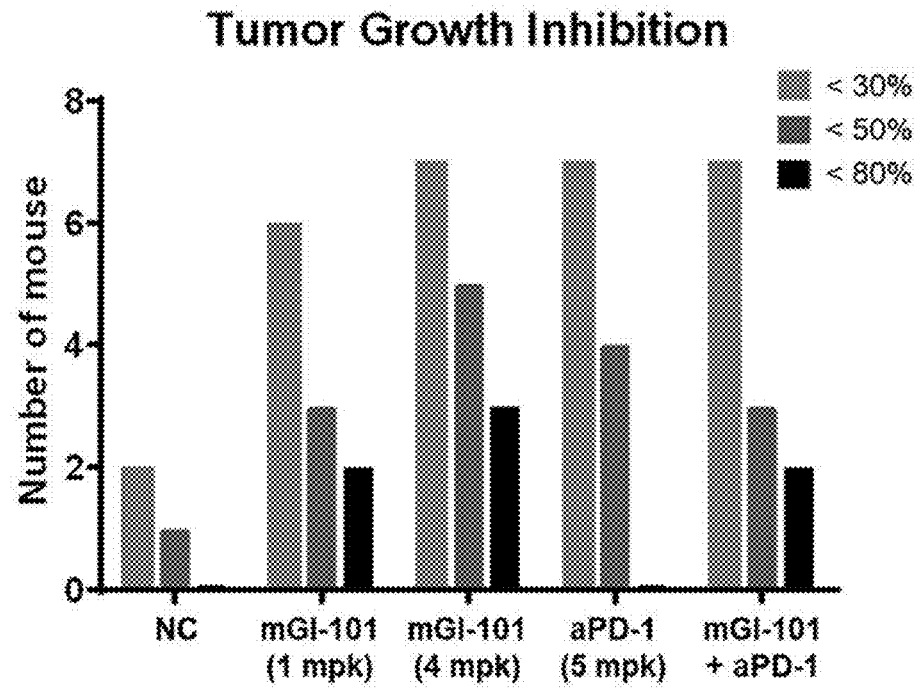

[Fig. 49]
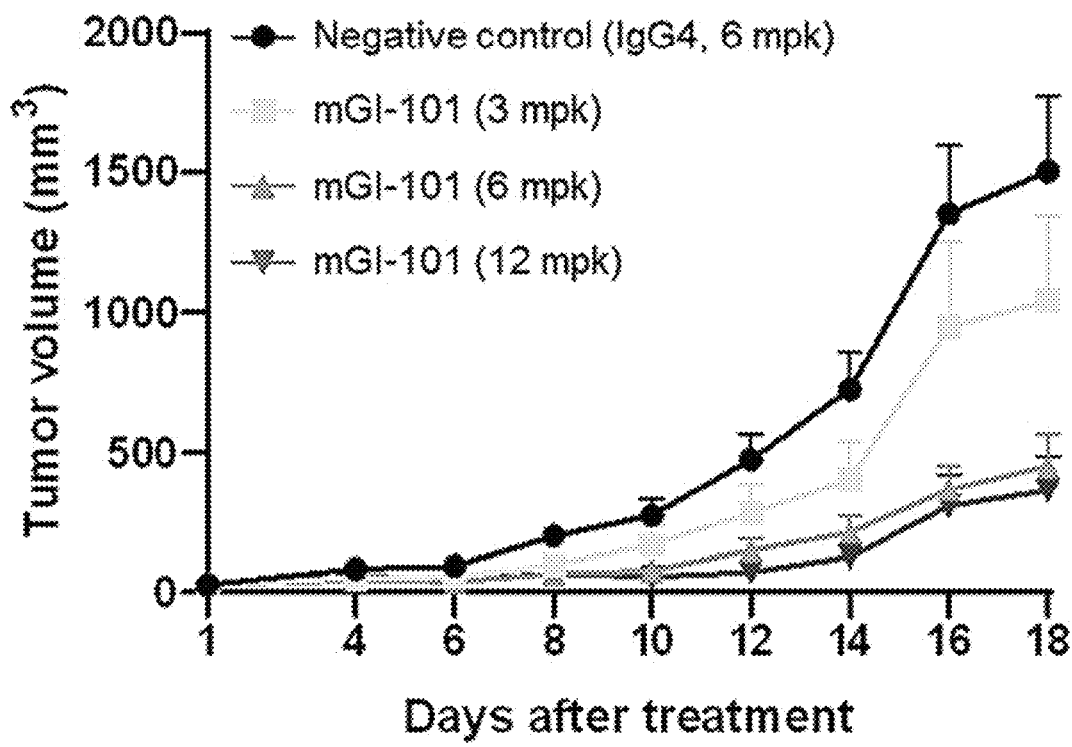
[Fig. 50]
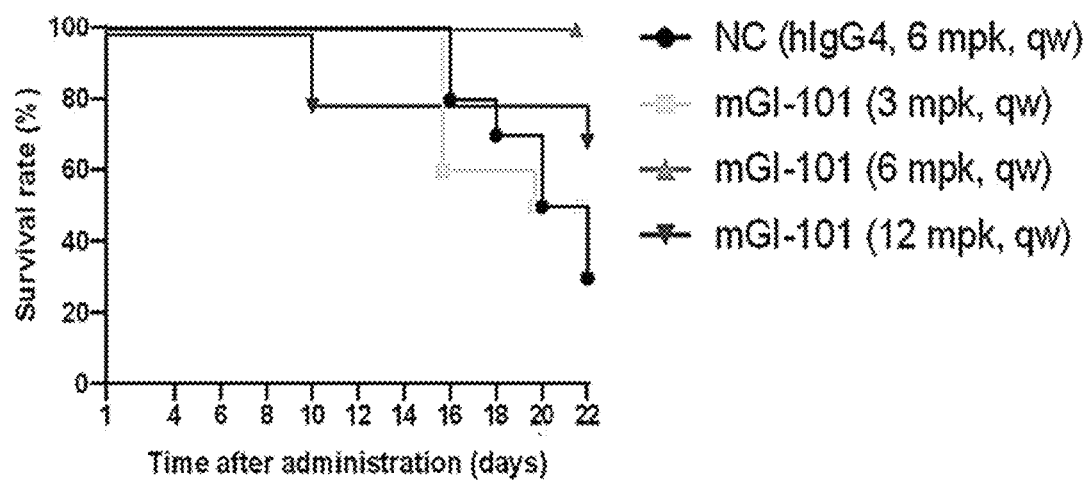

[Fig. 51]
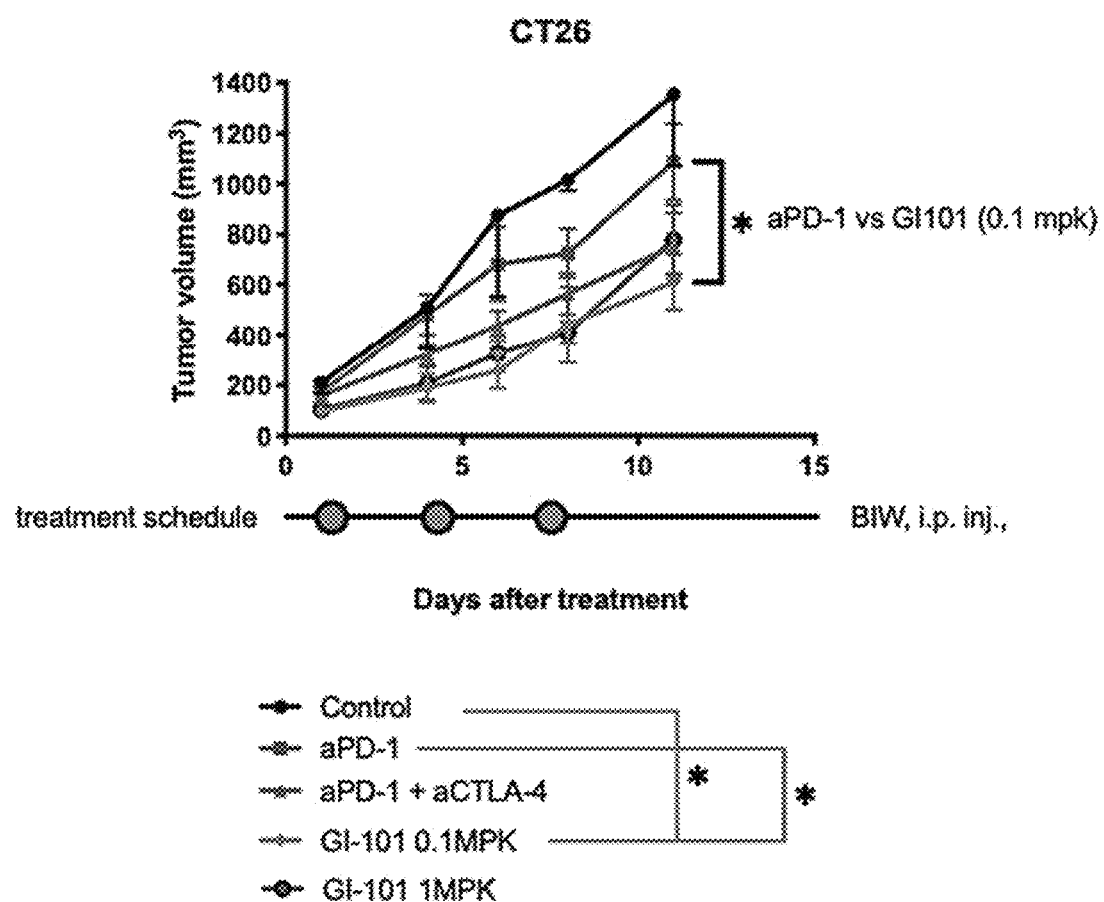

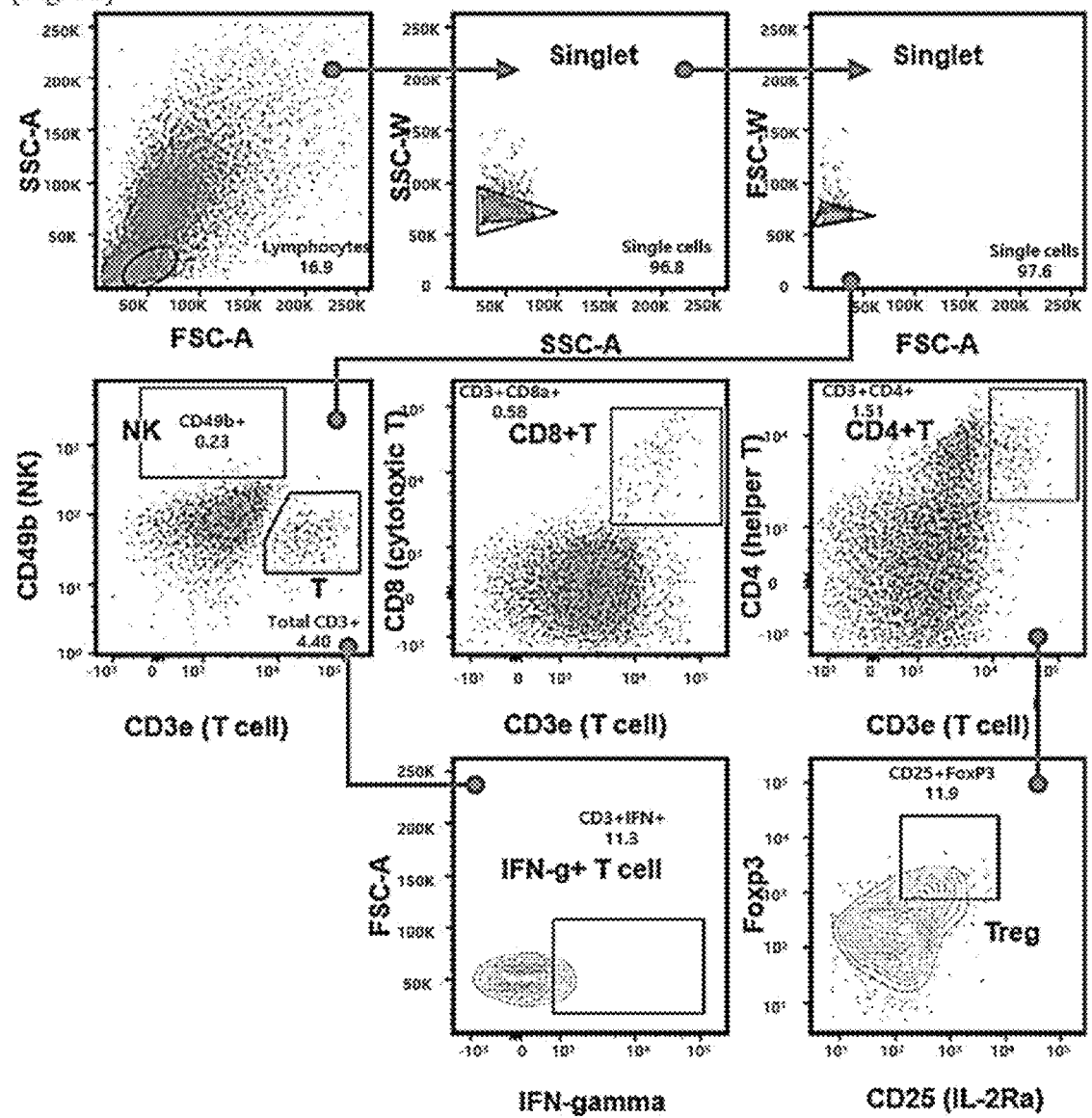

[Fig. 53]
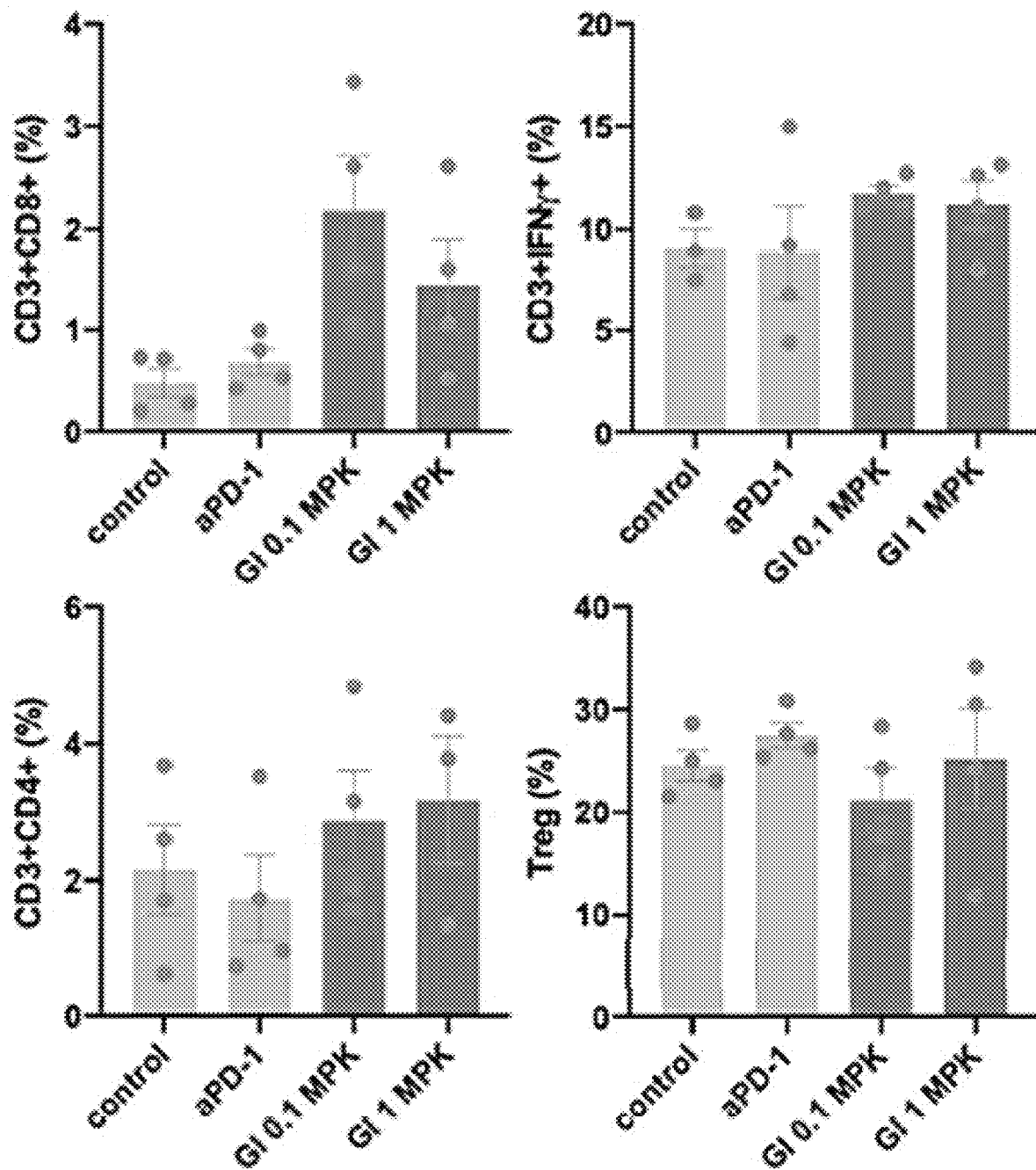

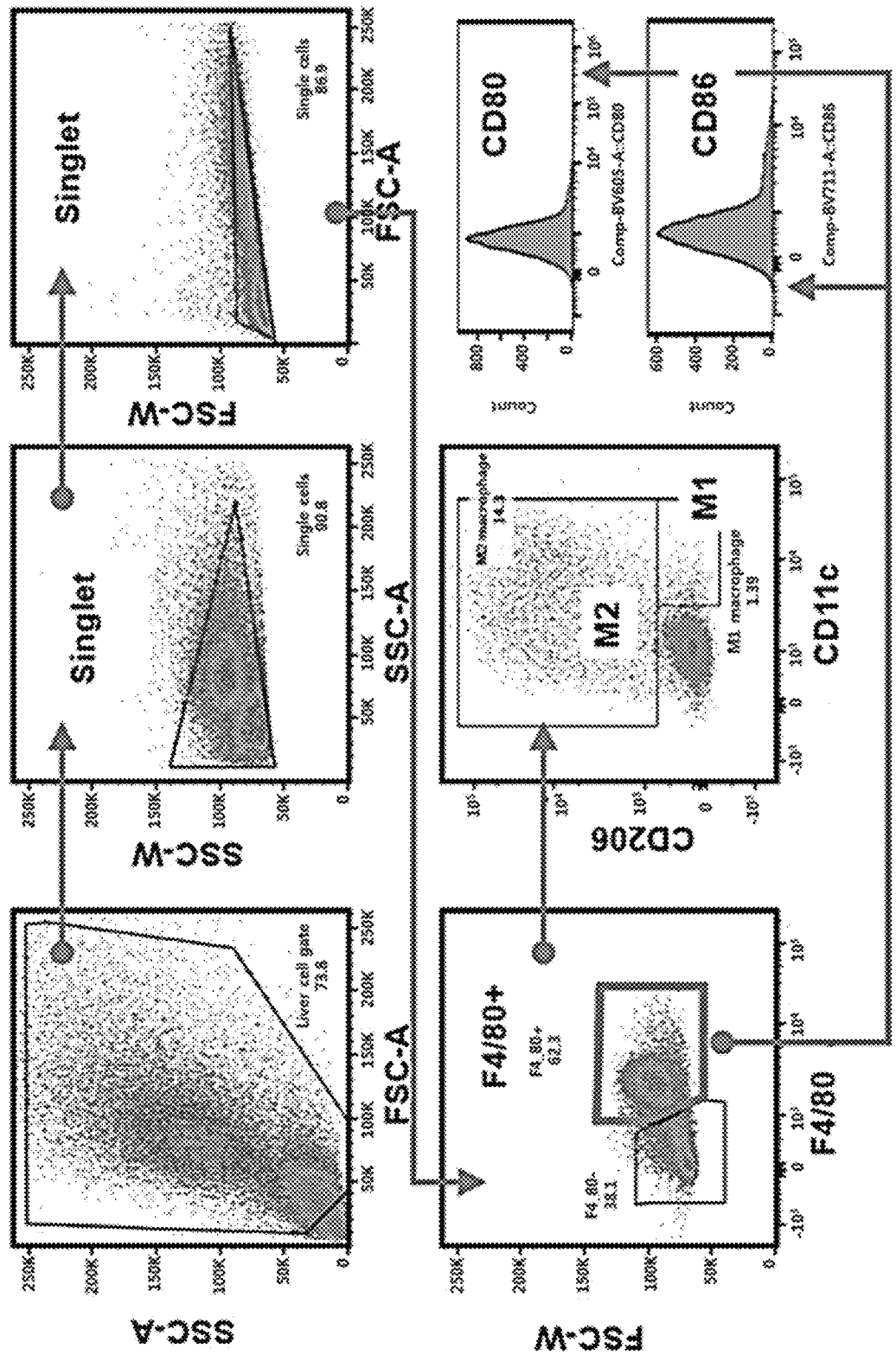
[Fig. 54]

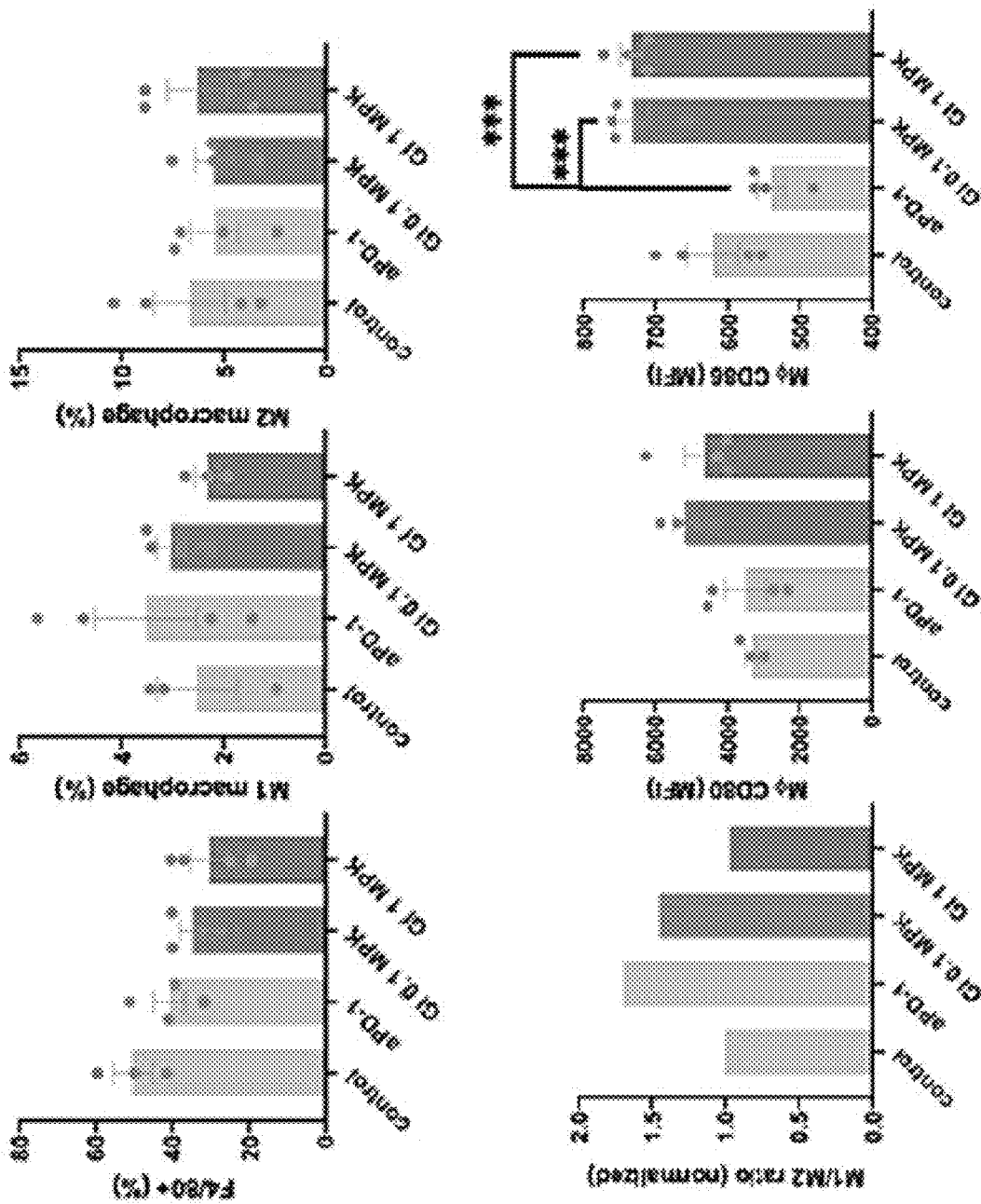
[Fig. 55]

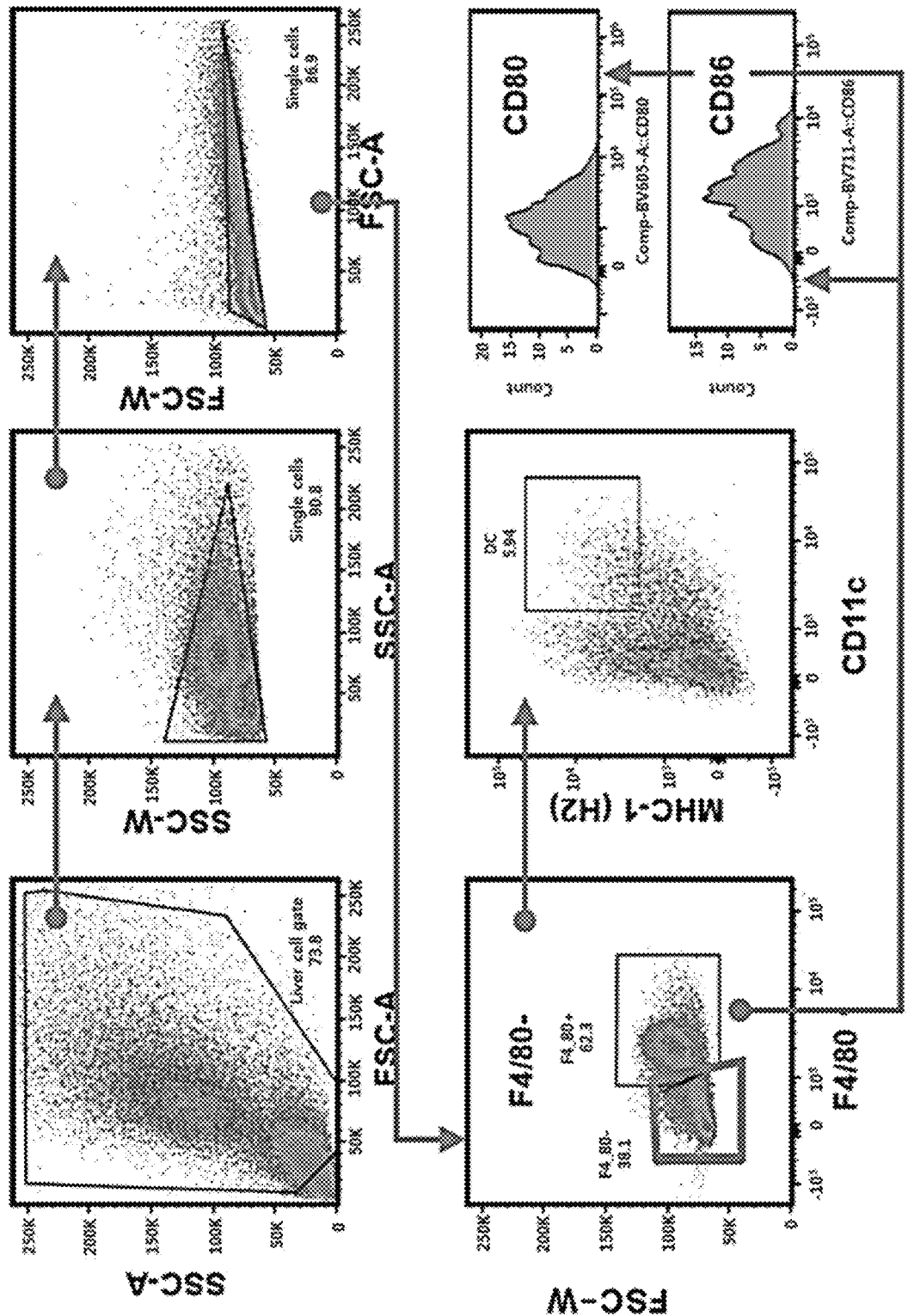
[Fig. S6]

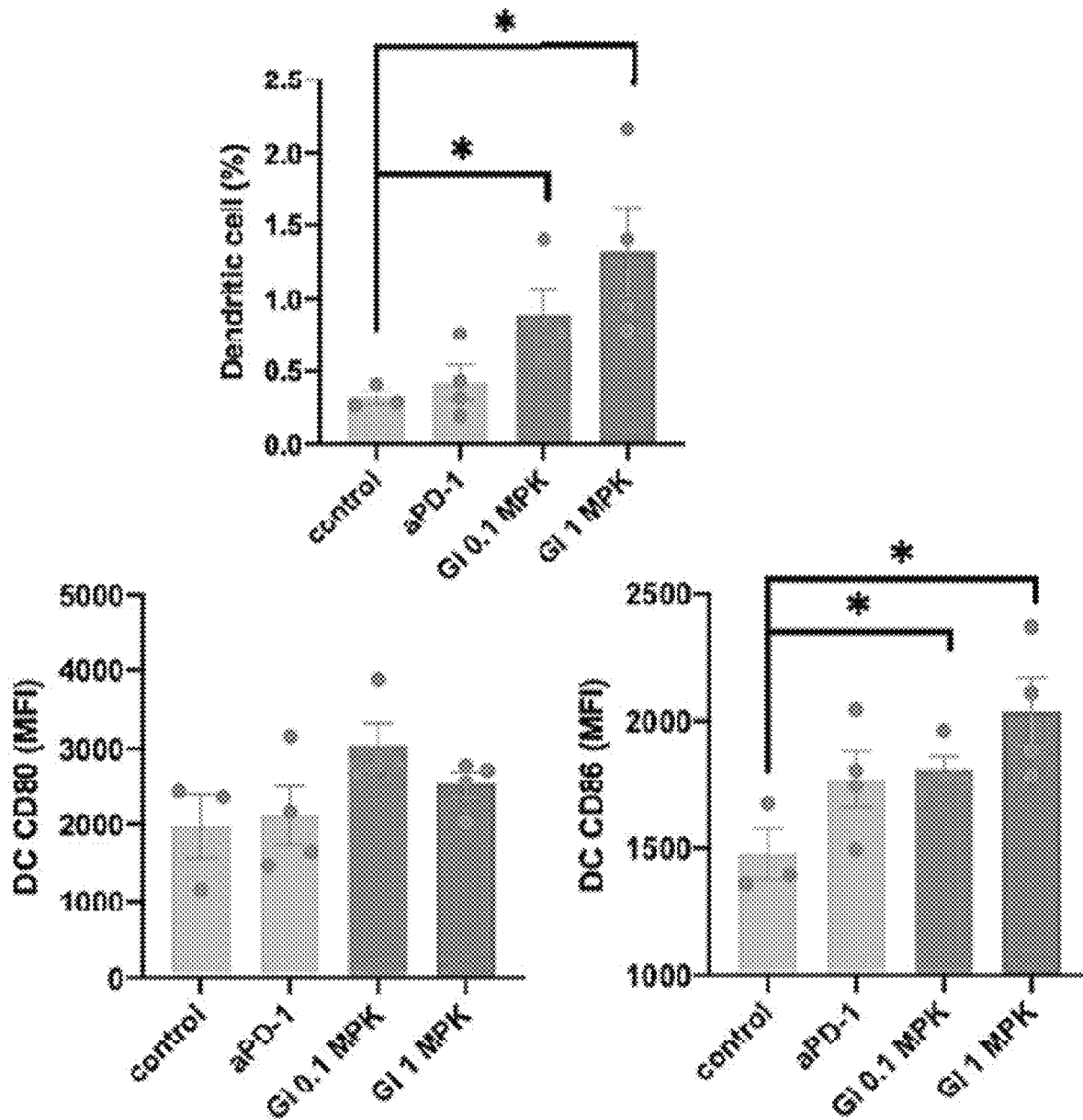
[Fig. 57]

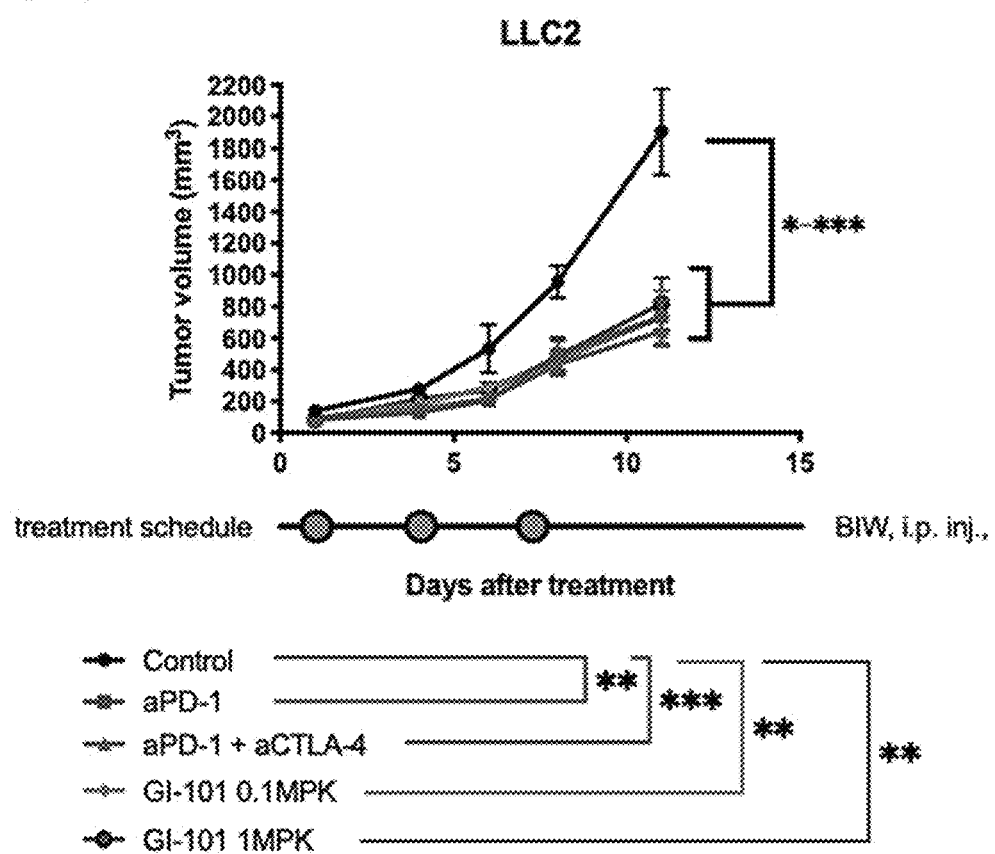

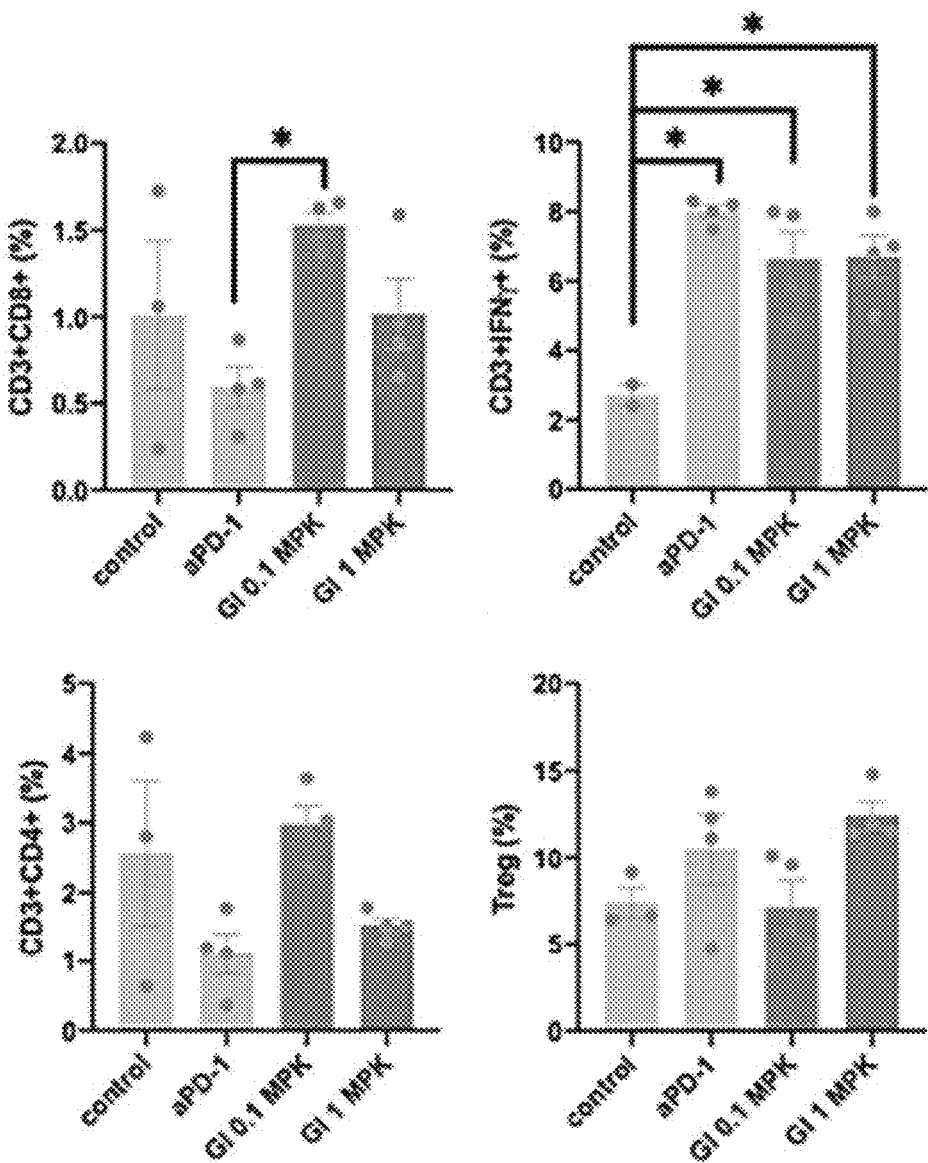

[Fig. 60]
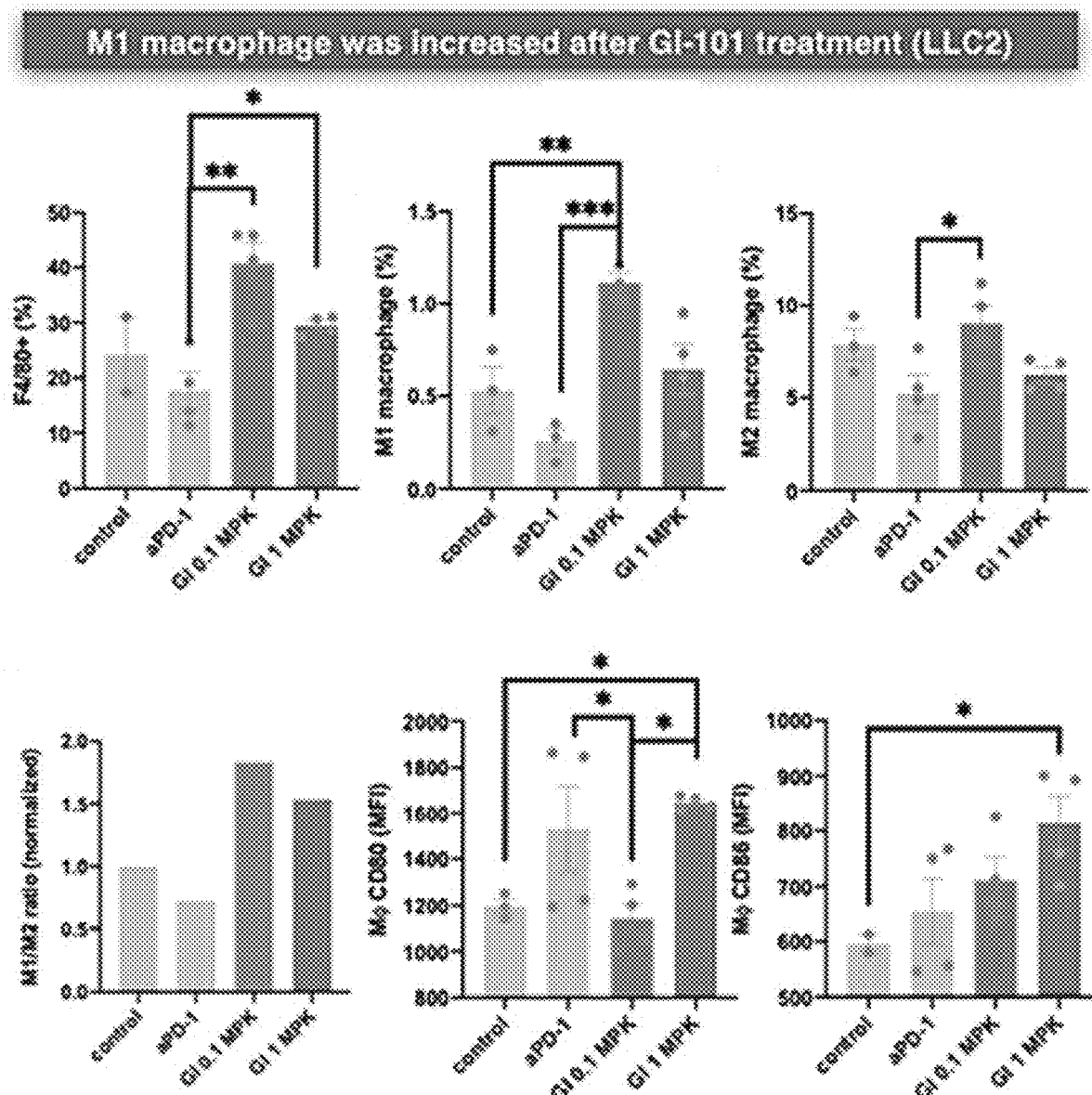

[Fig. 61]
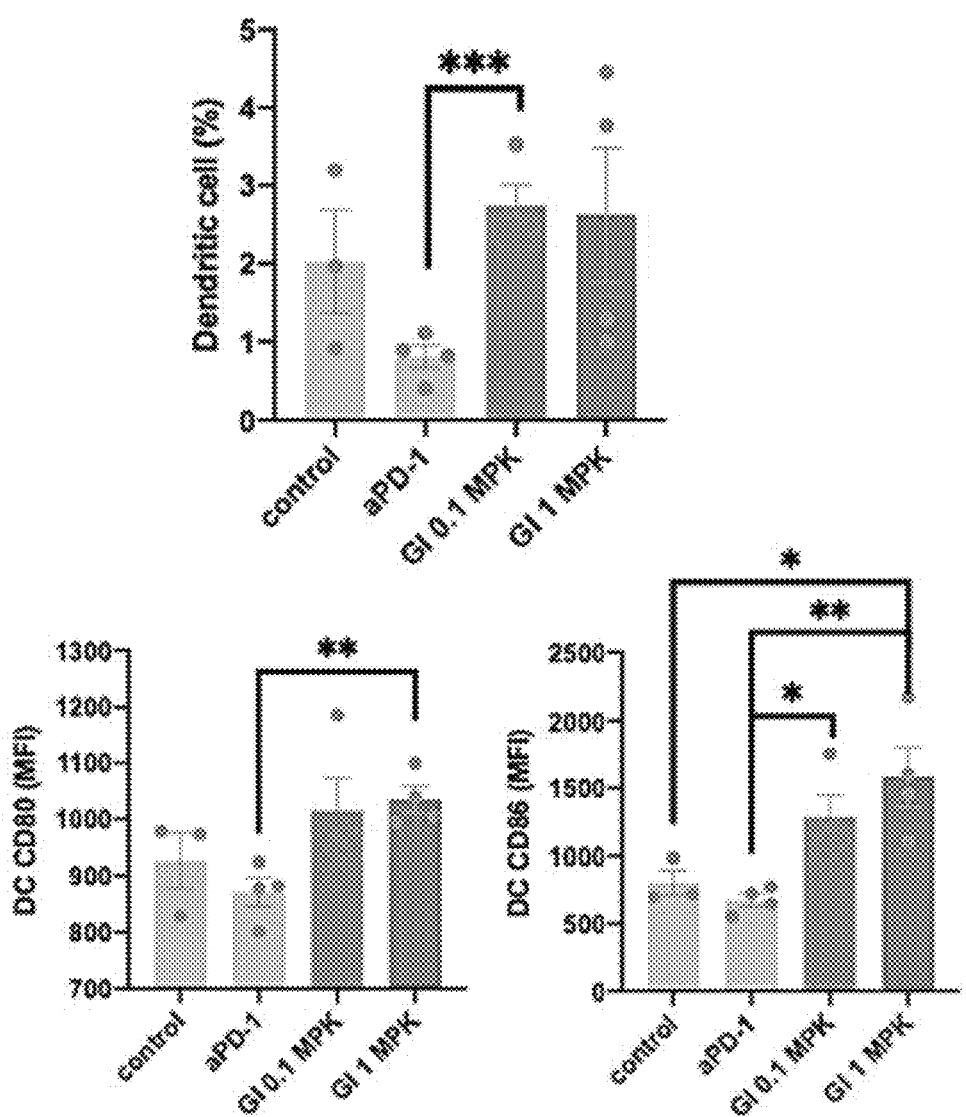

[Fig. 62]
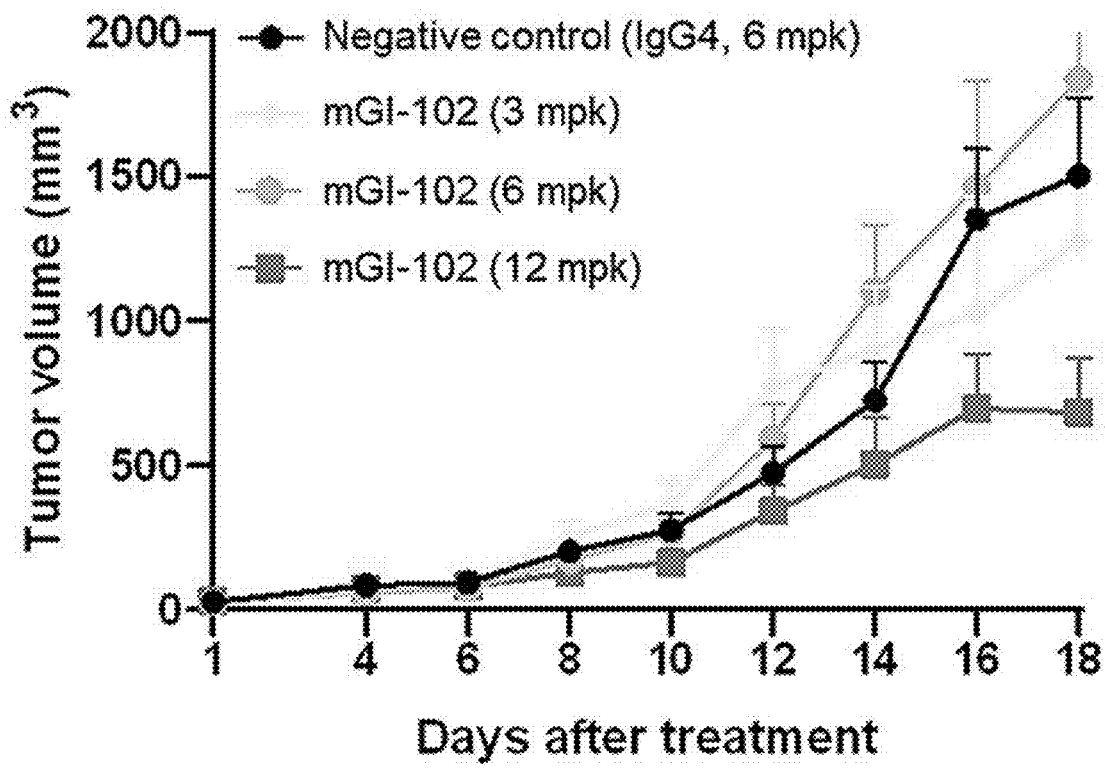
[Fig. 63]
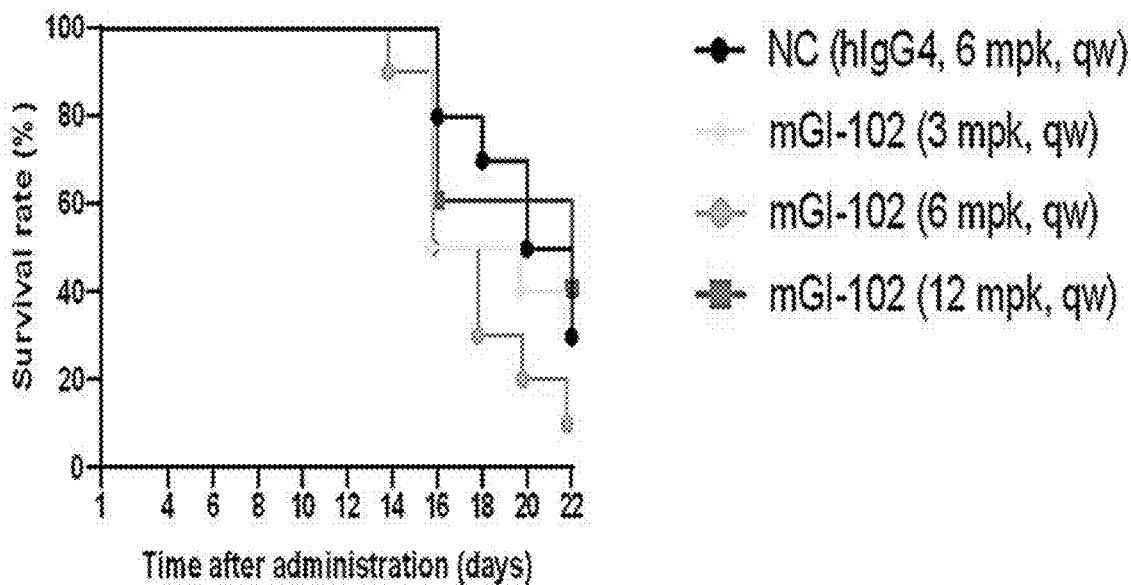

[Fig. 64]
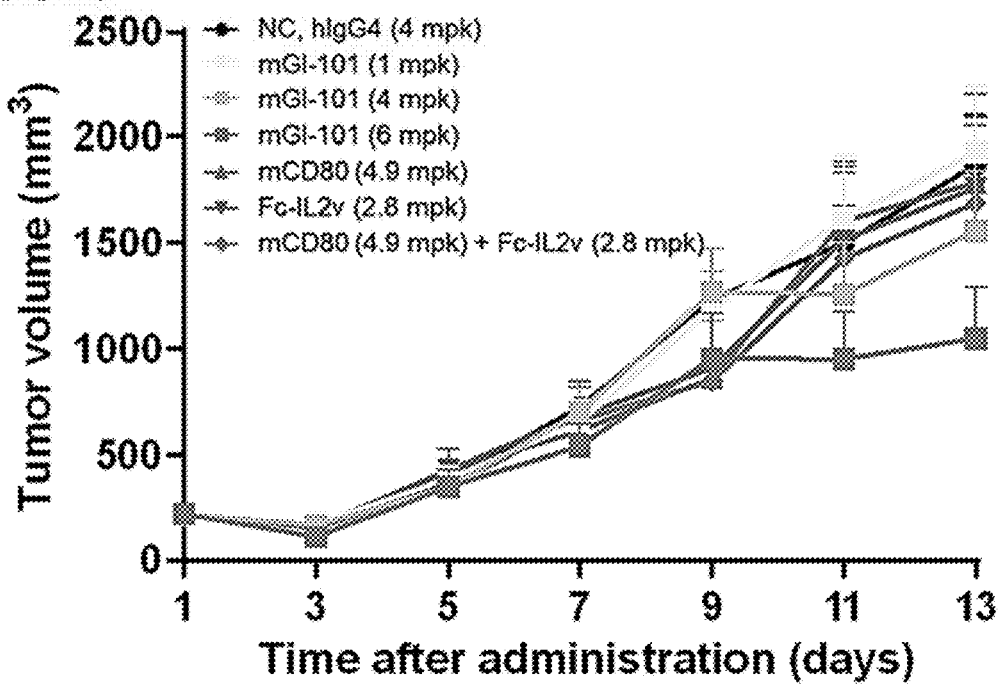
[Fig. 65]
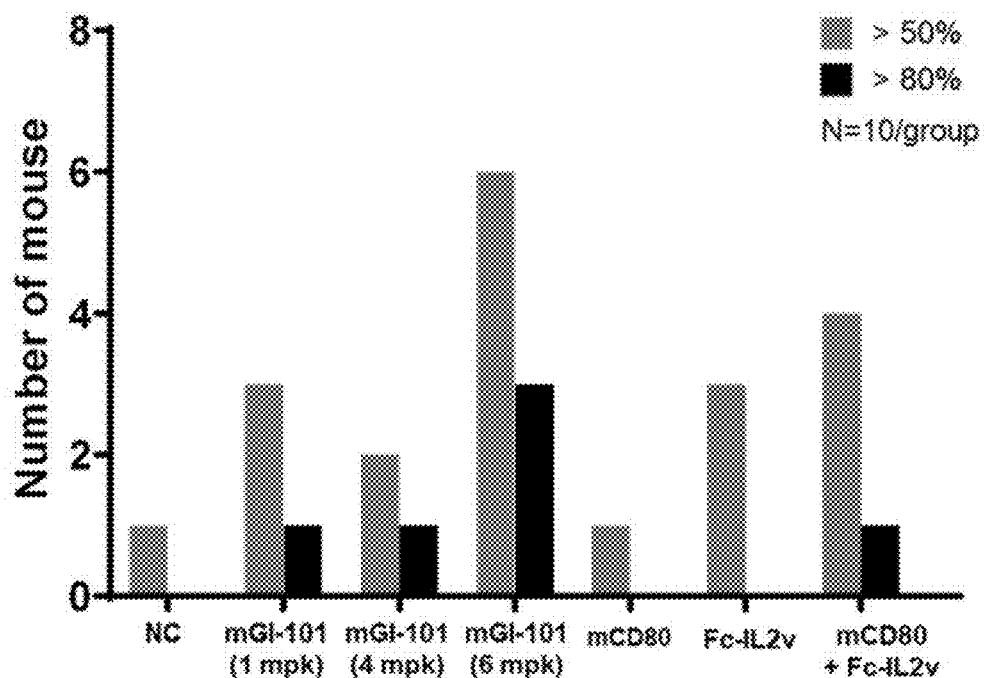

[Fig. 66]

A 2-Week Intravenous Dose Toxicity Study of GI-101 in Cynomolgus Monkeys

Table 1 Clinical observations

Sex: Male

| Group | Animal No. | -1 | | 1 | | 2 | 3 | 4 | 5 | 6 | 7 | 8 | | 9 | 10 | 11 | 12 | 13 | 14 | Day of necropsy |
|---|---|---|---|---|---|---|---|---|---|---|---|---|---|---|---|---|---|---|---|---|
| | | am | Pre | 0.5 h | am | am | am | am | am | am | am | Pre | 0.5 h | am | am | am | am | am | am | am |
| 0 mg/kg/day | CJ1M01 | NA | NA | NA | NA | NA | NA | NA | NA | NA | NA | NA | NA | NA | NA | NA | NA | NA | NA | NA |
| | CJ1M02 | NA | NA | NA | NA | NA | NA | NA | NA | NA | NA | NA | NA | NA | NA | NA | NA | NA | NA | NA |
| | CJ1M03 | NA | NA | NA | NA | NA | NA | NA | NA | NA | NA | NA | NA | NA | NA | NA | NA | NA | NA | NA |
| 5 mg/kg/day | CJ2M01 | NA | NA | NA | NA | NA | NA | NA | NA | NA | NA | NA | NA | NA | NA | NA | NA | NA | NA | NA |
| | CJ2M02 | NA | NA | NA | NA | NA | NA | NA | NA | NA | NA | NA | NA | NA | NA | NA | NA | NA | NA | NA |
| | CJ2M03 | NA | NA | NA | NA | NA | NA | NA | NA | NA | NA | NA | NA | NA | NA | NA | NA | NA | NA | NA |
| 10 mg/kg/day | CJ3M01 | NA | NA | NA | NA | NA | NA | NA | NA | NA | NA | NA | NA | NA | NA | NA | NA | NA | NA | NA |
| | CJ3M02 | NA | NA | NA | NA | NA | NA | NA | NA | NA | NA | NA | NA | NA | NA | NA | NA | NA | NA | NA |
| | CJ3M03 | NA | NA | NA | NA | NA | NA | NA | NA | NA | NA | NA | NA | NA | NA | NA | NA | NA | NA | NA |

General Footnote: Pre: Pre-dosing   0.5 h: 0.5 hours post-dosing
NA: No clinical or fecal abnormalities

[Fig. 67]
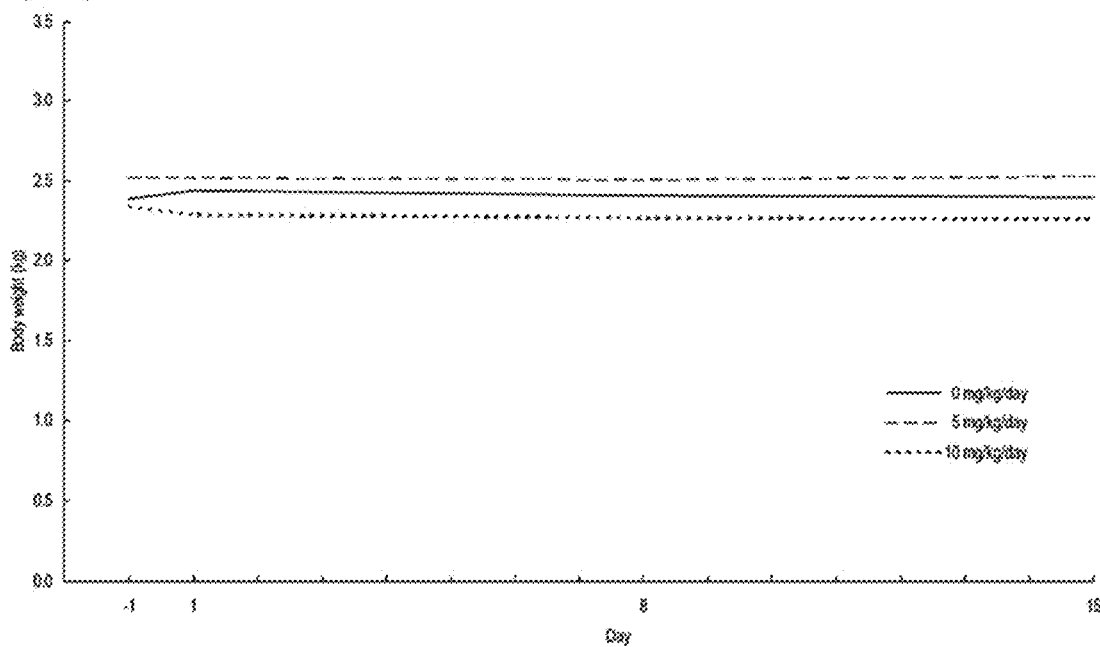
[Fig. 68]
Body weight (kg)
| Sex: Male<br>Day(s) Relative to Start Date | | 0<br>mg/kg/day | 5<br>mg/kg/day | 10<br>mg/kg/day |
|---|---|---|---|---|
| -1 | Mean | 2.39 | 2.52 | 2.34 |
|  | S.D. | 0.10 | 0.31 | 0.16 |
|  | N | 3 | 3 | 3 |
| 1 | Mean | 2.44 | 2.52 | 2.29 |
|  | S.D. | 0.07 | 0.31 | 0.16 |
|  | N | 3 | 3 | 3 |
| 8 | Mean | 2.41 | 2.51 | 2.27 |
|  | S.D. | 0.12 | 0.34 | 0.08 |
|  | N | 3 | 3 | 3 |
| 15 | Mean | 2.40 | 2.53 | 2.26 |
|  | S.D. | 0.12 | 0.34 | 0.11 |
|  | N | 3 | 3 | 3 |
Statistical Test: Generalised Anova/Ancova Test   Transformation: Identity (No Transformation)

[Fig. 69]

A 2-Week Intravenous Dose Toxicity Study of GI-101 in Cynomolgus Monkeys

Table 3  Food consumption

Sex: Male
Unit: (g/day)

| Group | Animal No. | -1 | 1 | 2 | 3 | 4 | 5 | 6 | 7 | Day 8 | 9 | 10 | 11 | 12 | 13 | 14 |
|---|---|---|---|---|---|---|---|---|---|---|---|---|---|---|---|---|
| 0 mg/kg/day | CJ1M01 | 100 | 100 | 100 | 100 | 100 | 100 | 100 | 100 | 100 | 100 | 100 | 100 | 100 | 100 | 100 |
| | CJ1M02 | 100 | 100 | 100 | 100 | 100 | 100 | 100 | 100 | 100 | 100 | 100 | 100 | 100 | 100 | 100 |
| | CJ1M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |
| 5 mg/kg/day | CJ2M01 | 100 | 100 | 100 | 100 | 100 | 100 | 100 | 100 | 100 | 100 | 100 | 100 | 100 | 100 | 100 |
| | CJ2M02 | 100 | 100 | 100 | 100 | 100 | 100 | 100 | 100 | 100 | 100 | 100 | 100 | 100 | 100 | 100 |
| | CJ2M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |
| 10 mg/kg/day | CJ3M01 | 100 | 100 | 100 | 100 | 100 | 100 | 100 | 100 | 100 | 100 | 100 | 100 | 100 | 100 | 100 |
| | CJ3M02 | 100 | 100 | 100 | 100 | 100 | 100 | 100 | 100 | 100 | 100 | 100 | 100 | 100 | 100 | 100 |
| | CJ3M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |

[Fig. 70]

| Sex: Male | | | 0 mg/kg/day | 5 mg/kg/day | 10 mg/kg/day |
|---|---|---|---|---|---|
| | Day(s) Relative to Start Date | | | | |
| %Retic. (%) | -2 | Mean | 0.75 | 1.40 | 0.53 |
| | | S.D. | 0.07 | 0.52 | 0.30 |
| | | N | 3 | 3 | 3 |
| | 15 | Mean | 1.67 | 3.10 d¹ | 3.14 d¹ |
| | | S.D. | 0.61 | 0.55 | 0.32 |
| | | N | 3 | 3 | 3 |
| #Retic (10^9/L) | -2 | Mean | 44.0 | 81.9 | 55.1 |
| | | S.D. | 7.0 | 26.4 | 19.7 |
| | | N | 3 | 3 | 3 |
| | 15 | Mean | 91.5 | 171.6 d¹ | 161.5 d¹ |
| | | S.D. | 33.6 | 32.3 | 17.2 |
| | | N | 3 | 3 | 3 |
| PLT (10^3/μL) | -2 | Mean | 404 | 383 | 380 |
| | | S.D. | 25 | 80 | 28 |
| | | N | 3 | 3 | 3 |
| | 15 | Mean | 581 | 522 | 601 |
| | | S.D. | 29 | 135 | 85 |
| | | N | 3 | 3 | 3 |

[Fig. 71]

| Sex: Male | | | 0 mg/kg/day | 5 mg/kg/day | 10 mg/kg/day |
|---|---|---|---|---|---|
| | Day(s) Relative to Start Date | | | | |
| WBC (10^3/μL) | -2 | Mean | 10.59 | 8.18 | 8.29 |
| | | S.D. | 1.63 | 1.43 | 2.11 |
| | | N | 3 | 3 | 3 |
| | 15 | Mean | 8.09 | 12.06 | 16.52 |
| | | S.D. | 0.25 | 0.74 | 6.81 |
| | | N | 3 | 3 | 3 |
| %Neut (%) | -2 | Mean | 38.1 | 23.1 | 23.6 |
| | | S.D. | 23.2 | 3.2 | 13.1 |
| | | N | 3 | 3 | 3 |
| | 15 | Mean | 35.9 | 14.5 | 22.4 |
| | | S.D. | 14.3 | 2.1 | 14.2 |
| | | N | 3 | 3 | 3 |
| %Lymph (%) | -2 | Mean | 57.7 | 71.6 | 68.8 |
| | | S.D. | 21.7 | 2.8 | 13.7 |
| | | N | 3 | 3 | 3 |
| | 15 | Mean | 59.6 | 81.2 | 69.5 |
| | | S.D. | 13.1 | 1.4 | 15.0 |
| | | N | 3 | 3 | 3 |

[Fig. 72]

| Sex: Male | | | 0 mg/kg/day | 5 mg/kg/day | 10 mg/kg/day |
|---|---|---|---|---|---|
| | Day(s) Relative to Start Date | | | | |
| #Neut (10^3/µL) | -2 | Mean | 4.24 | 1.86 | 1.77 |
| | | S.D. | 3.09 | 0.22 | 0.52 |
| | | N | 3 | 3 | 3 |
| | 15 | Mean | 2.93 | 1.76 | 3.11 |
| | | S.D. | 1.26 | 0.35 | 0.63 |
| | | N | 3 | 3 | 3 |
| #Lymph (10^3/µL) | -2 | Mean | 5.92 | 5.87 | 5.98 |
| | | S.D. | 1.78 | 1.24 | 2.54 |
| | | N | 3 | 3 | 3 |
| | 15 | Mean | 4.80 | 9.80 | 12.05 |
| | | S.D. | 0.94 | 0.49 | 6.47 |
| | | N | 3 | 3 | 3 |
| #Mono (10^3/µL) | -2 | Mean | 0.36 | 0.37 | 0.45 |
| | | S.D. | 0.18 | 0.09 | 0.08 |
| | | N | 3 | 3 | 3 |
| | 15 | Mean | 0.32 | 0.33 | 0.77 d' |
| | | S.D. | 0.11 | 0.06 | 0.26 |
| | | N | 3 | 3 | 3 |

[Fig. 73]

| Sex: Male | | | 0 mg/kg/day | 5 mg/kg/day | 10 mg/kg/day |
|---|---|---|---|---|---|
| | Day(s) Relative to Start Date | | | | |
| AST (U/L) | -2 | Mean | 36 | 45 | 30 |
| | | S.D. | 19 | 21 | 7 |
| | | N | 3 | 3 | 3 |
| | 15 | Mean | 24 | 34 | 33 |
| | | S.D. | 5 | 5 | 8 |
| | | N | 3 | 3 | 3 |
| ALT (U/L) | -2 | Mean | 58 | 72 | 34 |
| | | S.D. | 51 | 71 | 8 |
| | | N | 3 | 3 | 3 |
| | 15 | Mean | 34 | 52 | 36 |
| | | S.D. | 6 | 44 | 5 |
| | | N | 3 | 3 | 3 |
| ALP (U/L) | -2 | Mean | 1511 | 1638 | 1972 |
| | | S.D. | 542 | 258 | 357 |
| | | N | 3 | 3 | 3 |
| | 15 | Mean | 1395 | 1444 | 1565 |
| | | S.D. | 365 | 346 | 235 |
| | | N | 3 | 3 | 3 |

[Fig. 74]

| Sex: Male | | | 0 mg/kg/day | 5 mg/kg/day | 10 mg/kg/day |
|---|---|---|---|---|---|
| | Day(s) Relative to Start Date | | | | |
| LD (U/L) | -2 | Mean | 255 | 289 | 292 |
| | | S.D. | 6 | 57 | 47 |
| | | N | 3 | 3 | 3 |
| | 15 | Mean | 236 | 304 | 351 d#' |
| | | S.D. | 15 | 47 | 38 |
| | | N | 3 | 3 | 3 |
| CK (U/L) | -2 | Mean | 132 | 140 | 182 |
| | | S.D. | 23 | 4 | 61 |
| | | N | 3 | 3 | 3 |
| | 15 | Mean | 128 | 128 | 140 |
| | | S.D. | 31 | 19 | 23 |
| | | N | 3 | 3 | 3 |
| GLU (mg/dL) | -2 | Mean | 98 | 91 | 112 |
| | | S.D. | 17 | 4 | 15 |
| | | N | 3 | 3 | 3 |
| | 15 | Mean | 87 | 88 | 104 |
| | | S.D. | 9 | 17 | 5 |
| | | N | 3 | 3 | 3 |

[Fig. 75]

| Sex: Male | | | 0 mg/kg/day | 5 mg/kg/day | 10 mg/kg/day |
|---|---|---|---|---|---|
| | Day(s) Relative to Start Date | | | | |
| BIL (mg/dL) | -2 | Mean | 0.10 | 0.15 d' | 0.10 |
| | | S.D. | 0.02 | 0.03 | 0.01 |
| | | N | 3 | 3 | 3 |
| | 15 | Mean | 0.11 | 0.15 | 0.10 |
| | | S.D. | 0.04 | 0.03 | 0.03 |
| | | N | 3 | 3 | 3 |
| UN (mg/dL) | -2 | Mean | 19.1 | 15.4 | 18.8 |
| | | S.D. | 7.2 | 2.3 | 4.5 |
| | | N | 3 | 3 | 3 |
| | 15 | Mean | 16.2 | 13.9 | 14.2 |
| | | S.D. | 5.6 | 0.7 | 2.4 |
| | | N | 3 | 3 | 3 |
| CRE (mg/dL) | -2 | Mean | 0.73 | 0.69 | 0.73 |
| | | S.D. | 0.07 | 0.17 | 0.10 |
| | | N | 3 | 3 | 3 |
| | 15 | Mean | 0.72 | 0.66 | 0.65 |
| | | S.D. | 0.06 | 0.13 | 0.11 |
| | | N | 3 | 3 | 3 |

[Fig. 76]

| Sex: Male | | | 0 mg/kg/day | 5 mg/kg/day | 10 mg/kg/day |
|---|---|---|---|---|---|
| | Day(s) Relative to Start Date | | | | |
| CHO (mg/dL) | -2 | Mean | 109 | 162 | 147 |
| | | S.D. | 23 | 59 | 47 |
| | | N | 3 | 3 | 3 |
| | 15 | Mean | 108 | 159 | 143 |
| | | S.D. | 24 | 46 | 34 |
| | | N | 3 | 3 | 3 |
| TG (mg/dL) | -2 | Mean | 44 | 27 | 40 |
| | | S.D. | 24 | 12 | 2 |
| | | N | 3 | 3 | 3 |
| | 15 | Mean | 35 | 29 | 34 |
| | | S.D. | 2 | 14 | 14 |
| | | N | 3 | 3 | 3 |
| PL (mg/dL) | -2 | Mean | 180 | 236 | 220 |
| | | S.D. | 48 | 43 | 65 |
| | | N | 3 | 3 | 3 |
| | 15 | Mean | 164 | 218 | 195 |
| | | S.D. | 31 | 52 | 40 |
| | | N | 3 | 3 | 3 |

[Fig. 77]

| Sex: Male | | | 0 mg/kg/day | 5 mg/kg/day | 10 mg/kg/day |
|---|---|---|---|---|---|
| | Day(s) Relative to Start Date | | | | |
| IP (mg/dL) | -2 | Mean | 5.16 | 5.14 | 5.00 |
| | | S.D. | 1.16 | 0.91 | 0.90 |
| | | N | 3 | 3 | 3 |
| | 15 | Mean | 5.52 | 5.94 | 5.66 |
| | | S.D. | 0.61 | 0.51 | 0.94 |
| | | N | 3 | 3 | 3 |
| CA (mg/dL) | -2 | Mean | 9.53 | 9.82 | 9.79 |
| | | S.D. | 0.59 | 0.55 | 0.19 |
| | | N | 3 | 3 | 3 |
| | 15 | Mean | 9.45 | 9.48 | 9.31 |
| | | S.D. | 0.57 | 0.25 | 0.03 |
| | | N | 3 | 3 | 3 |
| NA (mEq/L) | -2 | Mean | 152.8 | 154.5 | 153.9 |
| | | S.D. | 2.4 | 4.2 | 2.5 |
| | | N | 3 | 3 | 3 |
| | 15 | Mean | 151.8 | 153.5 | 153.4 |
| | | S.D. | 3.3 | 2.0 | 3.3 |
| | | N | 3 | 3 | 3 |

[Fig. 78]

| Sex: Male | | | 0 mg/kg/day | 5 mg/kg/day | 10 mg/kg/day |
|---|---|---|---|---|---|
| | Day(s) Relative to Start Date | | | | |
| K (mEq/L) | -2 | Mean | 4.28 | 4.17 | 3.90 |
| | | S.D. | 0.69 | 0.29 | 0.40 |
| | | N | 3 | 3 | 3 |
| | 15 | Mean | 3.99 | 4.09 | 3.85 |
| | | S.D. | 0.50 | 0.18 | 0.14 |
| | | N | 3 | 3 | 3 |
| CL (mEq/L) | -2 | Mean | 112.3 | 111.1 | 110.7 |
| | | S.D. | 2.2 | 3.9 | 2.6 |
| | | N | 3 | 3 | 3 |
| | 15 | Mean | 111.5 | 109.6 | 110.2 |
| | | S.D. | 0.7 | 3.7 | 2.8 |
| | | N | 3 | 3 | 3 |
| TP (g/dL) | -2 | Mean | 7.20 | 7.36 | 7.53 |
| | | S.D. | 0.59 | 0.42 | 0.22 |
| | | N | 3 | 3 | 3 |
| | 15 | Mean | 6.99 | 7.22 | 7.30 |
| | | S.D. | 0.52 | 0.37 | 0.11 |
| | | N | 3 | 3 | 3 |

[Fig. 79]

| Sex: Male | | | 0 mg/kg/day | 5 mg/kg/day | 10 mg/kg/day |
|---|---|---|---|---|---|
| | Day(s) Relative to Start Date | | | | |
| ALB (g/dL) | -2 | Mean | 4.18 | 4.11 | 4.14 |
| | | S.D. | 0.34 | 0.46 | 0.19 |
| | | N | 3 | 3 | 3 |
| | 15 | Mean | 4.09 | 3.98 | 3.88 |
| | | S.D. | 0.36 | 0.47 | 0.17 |
| | | N | 3 | 3 | 3 |
| A/G | -2 | Mean | 1.39 | 1.27 | 1.22 |
| | | S.D. | 0.06 | 0.19 | 0.04 |
| | | N | 3 | 3 | 3 |
| | 15 | Mean | 1.41 | 1.24 | 1.13 |
| | | S.D. | 0.04 | 0.22 | 0.07 |
| | | N | 3 | 3 | 3 |

Sex: Male

| Group | Animal No. | Interleukin-6 (pg/mL) | | | | Interleukin-8 (pg/mL) | | | | Interleukin-10 (pg/mL) | | | | Interleukin-12 (pg/mL) | | | |
|---|---|---|---|---|---|---|---|---|---|---|---|---|---|---|---|---|---|
| | | Pretest | Day 3 | Day 8 | Day 15 | Pretest | Day 3 | Day 8 | Day 15 | Pretest | Day 3 | Day 8 | Day 15 | Pretest | Day 3 | Day 8 | Day 15 |
| 0 mg/kg/day | CJ1M01 | BLQ | 2.95 | BLQ | 3.34 | 4047.41 | 4861.65 | 7894.37 | 6780.89 | BLQ | BLQ | BLQ | BLQ | BLQ | BLQ | BLQ | BLQ |
| | CJ1M02 | BLQ | BLQ | BLQ | BLQ | 3418.18 | 1382.07 | 6035.41 | 4095.95 | BLQ | BLQ | BLQ | BLQ | BLQ | BLQ | BLQ | BLQ |
| | CJ1M03 | BLQ | 2.78 | BLQ | BLQ | 809.60 | 905.96 | 972.78 | 981.31 | BLQ | BLQ | BLQ | BLQ | BLQ | BLQ | BLQ | BLQ |
| | Mean | N.C. | 2.87 | N.C. | N.C. | 2758.40 | 2383.23 | 4967.52 | 3854.03 | N.C. | N.C. | N.C. | N.C. | N.C. | N.C. | N.C. | N.C. |
| | S.D. | N.C. | N.C. | N.C. | N.C. | 1716.78 | 2159.54 | 3582.23 | 2803.93 | N.C. | N.C. | N.C. | N.C. | N.C. | N.C. | N.C. | N.C. |
| | N | 0 | 2 | 0 | 1 | 3 | 3 | 3 | 3 | 0 | 0 | 0 | 0 | 0 | 0 | 0 | 0 |
| 5 mg/kg/day | CJ2M01 | BLQ | BLQ | BLQ | BLQ | 4860.40 | 3357.4 | 5386.48 | 5511.93 | BLQ | BLQ | BLQ | BLQ | BLQ | BLQ | BLQ | BLQ |
| | CJ2M02 | BLQ | BLQ | BLQ | BLQ | 2633.61 | 2338.95 | 4778.15 | 5255.08 | BLQ | BLQ | BLQ | BLQ | BLQ | BLQ | BLQ | BLQ |
| | CJ2M03 | BLQ | 2.91 | BLQ | BLQ | 7482.97 | 6571.81 | 9663.74 | 8592.13 | BLQ | BLQ | BLQ | BLQ | 7.07 | 6.31 | BLQ | BLQ |
| | Mean | N.C. | N.C. | N.C. | N.C. | 4972.33 | 4105.43 | 6609.46 | 6556.69 | N.C. | N.C. | N.C. | N.C. | N.C. | N.C. | N.C. | N.C. |
| | S.D. | N.C. | N.C. | N.C. | N.C. | 2429.25 | 2189.79 | 2544.64 | 2026.29 | N.C. | N.C. | N.C. | N.C. | N.C. | N.C. | N.C. | N.C. |
| | N | 0 | 1 | 0 | 0 | 3 | 3 | 3 | 3 | 0 | 0 | 0 | 0 | 1 | 1 | 0 | 0 |
| 10 mg/kg/day | CJ3M01 | BLQ | 5.26 | BLQ | BLQ | 8312.88 | 2753.66 | 7101.75 | 8973.45 | BLQ | 19.41 | BLQ | BLQ | 3.41 | BLQ | BLQ | 2.95 |
| | CJ3M02 | BLQ | BLQ | BLQ | BLQ | 7136.73 | 2722.78 | 9685.51 | 9298.79 | BLQ | 108.34 | BLQ | BLQ | BLQ | BLQ | BLQ | BLQ |
| | CJ3M03 | BLQ | 2.41 | BLQ | BLQ | 5832.12 | 4900.91 | 8873.95 | 9812.62 | BLQ | 39.40 | BLQ | BLQ | BLQ | BLQ | BLQ | BLQ |
| | Mean | N.C. | 3.84 | N.C. | N.C. | 7093.94 | 3459.12 | 8653.74 | 9361.62 | N.C. | 55.72 | N.C. | N.C. | N.C. | N.C. | N.C. | N.C. |
| | S.D. | N.C. | N.C. | N.C. | N.C. | 1240.88 | 1248.73 | 1454.44 | 423.10 | N.C. | 46.66 | N.C. | N.C. | N.C. | N.C. | N.C. | N.C. |
| | N | 0 | 2 | 0 | 0 | 3 | 3 | 3 | 3 d | 0 | 3 | 0 | 0 | 1 | 0 | 0 | 1 |

General Footnote: Day 8: Prior to dosing
BLQ: Below the lower limit of quantification (12.2 pg/mL for interleukin-10, 2.4 pg/mL for the others)
When plasma concentrations were BLQ in 1 of the 3 animals, the mean of the 2 remaining animals was calculated.
The mean was regarded as N.C. when plasma concentrations in 2 of the 3 animals were BLQ.
N.C.: Not calculated d: Test Dunnett 2 Sided p < 0.05)

[Fig. 82]

Sex: Male

| Group | Animal No. | T cell | | | | CD4 T cell | | | | CD8 T cell | | | | Regulatory T cell | | | | NK cell | | | |
|---|---|---|---|---|---|---|---|---|---|---|---|---|---|---|---|---|---|---|---|---|---|
| | | Pre | D3 | D8 | D15 | Pre | D3 | D8 | D15 | Pre | D3 | D8 | D15 | Pre | D3 | D8 | D15 | Pre | D3 | D8 | D15 |
| 0 mg/kg/day | CJ1M01 | 49.2 | 57.1 | 57.0 | 53.3 | 28.0 | 34.9 | 34.6 | 32.9 | 15.1 | 15.3 | 16.0 | 13.5 | 1.3 | 1.5 | 1.5 | 1.6 | 38.4 | 33.5 | 34.4 | 37.1 |
| | CJ1M02 | 69.4 | 68.5 | 67.3 | 55.2 | 27.3 | 29.6 | 25.4 | 19.0 | 35.7 | 31.7 | 35.6 | 30.4 | 0.8 | 0.9 | 0.8 | 0.7 | 18.3 | 10.9 | 20.3 | 30.5 |
| | CJ1M03 | 55.4 | 70.8 | 61.2 | 51.6 | 27.5 | 38.7 | 29.9 | 22.3 | 22.5 | 26.9 | 26.3 | 24.8 | 1.3 | 1.7 | 1.3 | 1.5 | 31.7 | 16.6 | 29.0 | 35.5 |
| | Mean | 58.0 | 65.5 | 61.8 | 53.4 | 27.6 | 34.4 | 30.0 | 24.7 | 24.4 | 24.6 | 26.0 | 22.9 | 1.1 | 1.4 | 1.2 | 1.3 | 29.5 | 20.3 | 27.9 | 34.4 |
| | S.D. | 10.3 | 7.3 | 5.2 | 1.8 | 0.4 | 4.6 | 4.6 | 7.3 | 10.4 | 8.4 | 9.8 | 8.6 | 0.3 | 0.4 | 0.4 | 0.5 | 10.2 | 11.8 | 7.1 | 3.4 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 5 mg/kg/day | CJ2M01 | 62.6 | 86.7 | 60.8 | 59.7 | 25.0 | 55.3 | 22.7 | 17.1 | 32.2 | 25.1 | 32.2 | 33.4 | 1.0 | 4.4 | 2.0 | 2.0 | 28.0 | 4.4 | 28.2 | 29.6 |
| | CJ2M02 | 52.7 | 75.9 | 55.3 | 51.9 | 22.7 | 41.0 | 24.3 | 19.4 | 24.8 | 28.2 | 25.6 | 25.6 | 0.8 | 3.6 | 2.6 | 1.6 | 27.2 | 6.3 | 28.9 | 34.4 |
| | CJ2M03 | 61.0 | 78.0 | 62.9 | 59.3 | 17.2 | 31.0 | 18.2 | 17.2 | 38.0 | 39.4 | 40.8 | 36.4 | 0.8 | 3.5 | 2.5 | 2.6 | 19.0 | 6.9 | 17.8 | 21.3 |
| | Mean | 58.8 | 80.2 | 59.7 | 57.0 | 21.6 | 42.4 | 21.1 | 17.9 | 31.7 | 30.9 | 32.9 | 32.5 | 0.9 | 3.8 | 2.4 | 2.1 | 24.1 | 5.9 | 25.0 | 28.4 |
| | S.D. | 5.3 | 5.7 | 3.9 | 4.4 | 4.0 | 12.2 | 4.3 | 1.3 | 6.6 | 7.5 | 7.6 | 6.0 | 0.1 | 0.5 | 0.3 | 0.5 | 4.4 | 1.3 | 6.2 | 6.6 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 10 mg/kg/day | CJ3M01 | 69.3 | 80.8 | 73.6 | 69.8 | 15.2 | 32.7 | 18.3 | 18.0 | 43.8 | 34.0 | 45.4 | 44.1 | 0.8 | 4.1 | 3.0 | 2.5 | 17.1 | 6.5 | 14.1 | 15.1 |
| | CJ3M02 | 65.2 | 66.4 | 65.4 | 66.0 | 18.4 | 28.4 | 13.7 | 16.6 | 39.0 | 48.8 | 42.1 | 37.3 | 0.6 | 2.8 | 1.6 | 1.9 | 16.0 | 3.8 | 14.8 | 15.3 |
| | CJ3M03 | 70.2 | 89.7 | 76.8 | 74.0 | 19.2 | 46.7 | 23.8 | 28.2 | 44.9 | 33.8 | 44.9 | 37.5 | 1.0 | 7.6 | 4.6 | 5.9 | 17.5 | 3.0 | 10.6 | 16.5 |
| | Mean | 68.2 | 85.6 | 71.9 | 69.9 | 17.6 | 35.9 | 18.6 | 20.9 | 42.6 | 39.1 | 44.1 | 39.6 | 0.8 | 4.8 | 3.1 | 3.4 | 16.9 | 4.4 | 13.2 | 15.6 |
| | S.D. | 2.7 | 4.5 | 5.9 | 4.0 | 2.1 | 9.6 | 5.1 | 6.3 | 3.1 | 8.4 | 1.8 | 3.9 | 0.2 | 2.5 | 1.5 | 2.2 | 0.8 | 1.8 | 2.3 | 0.8 |
| | N | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest    D3, D8 and D15: Days 3, 8 (prior to dosing) and 15
1 [d - Test: Dunnett 2 Sided p < 0.05]    2 [dd - Test: Dunnett 2 Sided p < 0.01]

[Fig. 83]

Sex: Male

| Group | Animal No. | Lymphocytes (10^3/μL) | | Absolute count (10^3/μL) | | | | | | | | |
|---|---|---|---|---|---|---|---|---|---|---|---|---|
| | | | | T cell | | CD4 T cell | | CD8 T cell | | Regulatory T cell | | NK cell |
| | | Pre | D15 | Pre | D15 | Pre | D15 | Pre | D15 | Pre | D15 | Pre | D15 |
| 0 mg/kg/day | CJ1M01 | 7.40 | 5.60 | 3.64 | 2.98 | 2.07 | 1.84 | 1.12 | 0.76 | 0.10 | 0.09 | 2.84 | 2.98 |
| | CJ1M02 | 6.42 | 5.03 | 4.46 | 2.78 | 1.75 | 0.96 | 2.29 | 1.53 | 0.05 | 0.04 | 1.17 | 1.53 |
| | CJ1M03 | 3.94 | 3.77 | 2.18 | 1.95 | 1.08 | 0.84 | 0.89 | 0.93 | 0.05 | 0.06 | 1.25 | 1.34 |
| | Mean | 5.92 | 4.80 | 3.43 | 2.57 | 1.63 | 1.21 | 1.43 | 1.07 | 0.07 | 0.06 | 1.75 | 1.95 |
| | S.D. | 1.78 | 0.94 | 1.15 | 0.55 | 0.51 | 0.55 | 0.75 | 0.40 | 0.03 | 0.03 | 0.94 | 0.90 |
| | N | 3 | 3 | 3 | 3 | 3 | 3 | 3 | 3 | 3 | 3 | 3 | 3 |
| 5 mg/kg/day | CJ2M01 | 5.01 | 9.42 | 3.14 | 5.62 | 1.25 | 1.81 | 1.61 | 3.33 | 0.05 | 0.19 | 1.30 | 2.79 |
| | CJ2M02 | 7.29 | 10.34 | 3.84 | 5.37 | 1.65 | 2.01 | 1.81 | 2.65 | 0.06 | 0.17 | 1.98 | 3.56 |
| | CJ2M03 | 5.32 | 9.63 | 3.25 | 5.71 | 0.92 | 1.66 | 2.02 | 3.51 | 0.04 | 0.25 | 1.01 | 2.05 |
| | Mean | 5.87 | 9.80 | 3.41 | 5.57 | 1.27 | 1.76 | 1.81 | 3.16 | 0.05 | 0.20 d^d | 1.43 | 2.80 |
| | S.D. | 1.24 | 0.48 | 0.38 | 0.18 | 0.37 | 0.22 | 0.21 | 0.45 | 0.01 | 0.04 | 0.50 | 0.76 |
| | N | 3 | 3 | 3 | 3 | 3 | 3 | 3 | 3 | 3 | 3 | 3 | 3 |
| 10 mg/kg/day | CJ3M01 | 8.38 | 13.41 | 5.81 | 9.38 | 1.27 | 2.41 | 3.67 | 6.91 | 0.07 | 0.34 | 1.43 | 2.02 |
| | CJ3M02 | 6.25 | 17.73 | 4.88 | 11.70 | 1.15 | 2.94 | 2.44 | 6.61 | 0.04 | 0.34 | 1.00 | 2.71 |
| | CJ3M03 | 3.32 | 5.01 | 2.33 | 3.71 | 0.64 | 1.41 | 1.49 | 1.88 | 0.03 | 0.30 | 0.58 | 0.83 |
| | Mean | 5.98 | 12.05 | 4.07 d^d | 8.26 | 1.02 | 2.25 | 2.53 d^d | 4.80 | 0.05 | 0.33 d^d | 1.00 | 1.85 |
| | S.D. | 2.54 | 6.47 | 1.74 | 4.11 | 0.33 | 0.78 | 1.09 | 2.56 | 0.02 | 0.02 | 0.43 | 0.95 |
| | N | 3 | 3 | 3 | 3 | 3 | 3 | 3 | 3 | 3 | 3 | 3 | 3 |

General Footnote: Pre: Pretest  D15: Day 15
1 [d - Test Dunnett 2 Sided p < 0.05]
2 [dd - Test Dunnett 2 Sided p < 0.01]

[Fig. 84]

Sex: Male

| Group | Animal No. | Ratio to baseline (pretest, %) | | | | | | | | | | | | | | | |
|---|---|---|---|---|---|---|---|---|---|---|---|---|---|---|---|---|---|
| | | T cell | | | | CD4 T cell | | | | CD8 T cell | | | | Regulatory T cell | | | | NK cell |
| | | Pre | D3 | D8 | D15 | Pre | D3 | D8 | D15 | Pre | D3 | D8 | D15 | Pre | D3 | D8 | D15 | Pre | D3 | D8 | D15 |
| 0 mg/kg/day | CJ1M01 | 1.00 | 1.16 | 1.16 | 1.06 | 1.00 | 1.25 | 1.24 | 1.18 | 1.00 | 1.01 | 1.06 | 0.89 | 1.00 | 1.15 | 1.15 | 1.23 | 1.00 | 0.87 | 0.90 | 0.97 |
| | CJ1M02 | 1.00 | 0.99 | 0.97 | 0.80 | 1.00 | 1.08 | 0.93 | 0.70 | 1.00 | 0.89 | 1.00 | 0.85 | 1.00 | 1.13 | 1.00 | 0.88 | 1.00 | 0.60 | 1.11 | 1.57 |
| | CJ1M03 | 1.00 | 1.28 | 1.10 | 0.93 | 1.00 | 1.41 | 1.09 | 0.81 | 1.00 | 1.20 | 1.17 | 1.10 | 1.00 | 1.31 | 1.08 | 1.15 | 1.00 | 0.52 | 0.91 | 1.12 |
| | Mean | 1.00 | 1.14 | 1.08 | 0.94 | 1.00 | 1.25 | 1.09 | 0.90 | 1.00 | 1.03 | 1.08 | 0.95 | 1.00 | 1.20 | 1.05 | 1.09 | 1.00 | 0.66 | 0.97 | 1.25 |
| | S.D. | 0.00 | 0.15 | 0.10 | 0.14 | 0.00 | 0.17 | 0.16 | 0.25 | 0.00 | 0.16 | 0.09 | 0.13 | 0.00 | 0.10 | 0.08 | 0.18 | 0.00 | 0.18 | 0.12 | 0.37 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 5 mg/kg/day | CJ2M01 | 1.00 | 1.38 | 0.97 | 0.95 | 1.00 | 2.21 | 0.91 | 0.68 | 1.00 | 0.78 | 1.00 | 1.10 | 1.00 | 4.40 | 2.00 | 2.00 | 1.00 | 0.17 | 1.08 | 1.14 |
| | CJ2M02 | 1.00 | 1.44 | 1.05 | 0.98 | 1.00 | 1.81 | 1.07 | 0.85 | 1.00 | 1.14 | 1.03 | 1.03 | 1.00 | 4.50 | 3.25 | 2.00 | 1.00 | 0.23 | 1.06 | 1.26 |
| | CJ2M03 | 1.00 | 1.28 | 1.03 | 0.97 | 1.00 | 1.80 | 0.94 | 1.00 | 1.00 | 1.04 | 1.07 | 0.96 | 1.00 | 4.38 | 3.13 | 3.25 | 1.00 | 0.36 | 0.94 | 1.12 |
| | Mean | 1.00 | 1.37 | 1.02 | 0.97 | 1.00 | 1.94 | 0.97 | 0.84 | 1.00 | 0.99 | 1.03 | 1.03 | 1.00 | 4.43 dd^ | 2.79 d^ | 2.42 | 1.00 | 0.25 d^ | 1.03 | 1.17 |
| | S.D. | 0.00 | 0.08 | 0.04 | 0.02 | 0.00 | 0.23 | 0.09 | 0.16 | 0.00 | 0.19 | 0.04 | 0.07 | 0.00 | 0.06 | 0.69 | 0.72 | 0.00 | 0.10 | 0.08 | 0.08 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 10 mg/kg/day | CJ3M01 | 1.00 | 1.17 | 1.05 | 1.01 | 1.00 | 2.15 | 1.20 | 1.18 | 1.00 | 0.79 | 1.04 | 1.01 | 1.00 | 5.13 | 3.75 | 3.13 | 1.00 | 0.38 | 0.82 | 0.88 |
| | CJ3M02 | 1.00 | 1.33 | 1.00 | 1.01 | 1.00 | 1.54 | 0.74 | 0.90 | 1.00 | 1.25 | 1.08 | 0.96 | 1.00 | 4.67 | 2.67 | 3.17 | 1.00 | 0.24 | 0.93 | 0.95 |
| | CJ3M03 | 1.00 | 1.28 | 1.09 | 1.05 | 1.00 | 2.43 | 1.24 | 1.47 | 1.00 | 0.75 | 1.00 | 0.84 | 1.00 | 7.60 | 4.60 | 5.90 | 1.00 | 0.17 | 0.61 | 0.94 |
| | Mean | 1.00 | 1.26 | 1.05 | 1.02 | 1.00 | 2.04 d^ | 1.06 | 1.18 | 1.00 | 0.93 | 1.04 | 0.94 | 1.00 | 5.80 dd^ | 3.67 dd^ | 4.07 d^ | 1.00 | 0.26 d^ | 0.79 | 0.93 |
| | S.D. | 0.00 | 0.08 | 0.05 | 0.02 | 0.00 | 0.46 | 0.28 | 0.29 | 0.00 | 0.28 | 0.04 | 0.09 | 0.00 | 1.58 | 0.97 | 1.59 | 0.00 | 0.11 | 0.16 | 0.04 |
| | N | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest  D3, D8 and D15: Days 3, 8 (prior to dosing) and 15
1 [d - Test Dunnett 2 Sided p < 0.05]
2 [dd - Test Dunnett 2 Sided p < 0.01]

Sex: Male

| Group | Animal No. | K67+ T cell | | K67+ CD4 T cell | | K67+ CD8 T cell | | K67+ Treg | | K67+ ICOS+ Treg | | ICOS+ Treg | | K67+ NK cell | |
|---|---|---|---|---|---|---|---|---|---|---|---|---|---|---|---|
| | | Pre | D15 | Pre | D15 | Pre | D15 | Pre | D15 | Pre | D15 | Pre | D15 | Pre | D15 |
| 0 mg/kg/day | CJ1M01 | 0.35 | 0.31 | 0.19 | 0.15 | 0.07 | 0.07 | 0.03 | 0.02 | 0.03 | 0.02 | 0.05 | 0.03 | 0.20 | 0.20 |
| | CJ1M02 | 0.49 | 0.28 | 0.13 | 0.10 | 0.27 | 0.11 | 0.01 | 0.01 | 0.01 | 0.01 | 0.01 | 0.01 | 0.24 | 0.13 |
| | CJ1M03 | 0.22 | 0.33 | 0.08 | 0.13 | 0.11 | 0.15 | 0.01 | 0.01 | 0.01 | 0.02 | 0.02 | 0.03 | 0.19 | 0.34 |
| | Mean | 0.35 | 0.31 | 0.13 | 0.13 | 0.15 | 0.11 | 0.02 | 0.01 | 0.02 | 0.02 | 0.03 | 0.02 | 0.21 | 0.22 |
| | S.D. | 0.14 | 0.03 | 0.06 | 0.03 | 0.11 | 0.04 | 0.01 | 0.01 | 0.01 | 0.01 | 0.02 | 0.01 | 0.03 | 0.11 |
| | N | 3 | | 3 | | 3 | | 3 | | 3 | | 3 | | 3 | |
| 5 mg/kg/day | CJ2M01 | 0.33 | 1.71 | 0.12 | 0.24 | 0.16 | 1.15 | 0.02 | 0.12 | 0.02 | 0.09 | 0.02 | 0.10 | 0.11 | 1.26 |
| | CJ2M02 | 0.25 | 1.32 | 0.09 | 0.23 | 0.09 | 0.75 | 0.02 | 0.07 | 0.02 | 0.05 | 0.03 | 0.07 | 0.23 | 0.86 |
| | CJ2M03 | 0.32 | 1.88 | 0.11 | 0.29 | 0.16 | 1.27 | 0.02 | 0.12 | 0.01 | 0.06 | 0.02 | 0.07 | 0.08 | 0.93 |
| | Mean | 0.30 | 1.61 | 0.11 | 0.25 | 0.14 | 1.06 | 0.02 | 0.10 | 0.02 | 0.07 | 0.02 | 0.08 | 0.14 | 1.35 |
| | S.D. | 0.04 | 0.29 | 0.02 | 0.03 | 0.04 | 0.27 | 0.01 | 0.03 | 0.01 | 0.02 | 0.01 | 0.02 | 0.08 | 0.47 |
| | N | 3 | | 3 | | 3 | | 3 | | 3 | | 3 | | 3 | |
| 10 mg/kg/day | CJ3M01 | 0.66 | 3.08 | 0.16 | 0.44 | 0.35 | 2.18 | 0.03 | 0.19 | 0.03 | 0.11 | 0.04 | 0.09 | 0.08 | 0.48 |
| | CJ3M02 | 0.37 | 3.45 | 0.10 | 0.39 | 0.18 | 2.15 | 0.01 | 0.16 | 0.01 | 0.11 | 0.02 | 0.15 | 0.13 | 1.19 |
| | CJ3M03 | 0.23 | 1.28 | 0.07 | 0.29 | 0.12 | 0.50 | 0.01 | 0.18 | 0.01 | 0.11 | 0.02 | 0.15 | 0.06 | 0.42 |
| | Mean | 0.42 | 2.58 | 0.11 | 0.37 | 0.22 | 1.68 | 0.02 | 0.18 | 0.02 | 0.10 | 0.03 | 0.13 | 0.09 | 0.70 |
| | S.D. | 0.22 | 1.21 | 0.05 | 0.08 | 0.12 | 0.83 | 0.01 | 0.02 | 0.01 | 0.02 | 0.01 | 0.03 | 0.04 | 0.43 |
| | N | 3 | | 3 | | 3 | | 3 | | 3 | | 3 | | 3 | |

General Footnote: Pre: Pretest    D15: Day 15    Treg: Regulatory T cell
1 [a - Test: Dunnett 2 Sided p < 0.05]    2 [aa - Test: Dunnett 2 Sided p < 0.01]

[Fig. 87]

[Fig. 88]
Day(s): 15 Relative to Start Date
| Sex: Male | | 0 mg/kg/day | 5 mg/kg/day | 10 mg/kg/day |
|---|---|---|---|---|
| Liver (g) | Mean | 41.5 | 42.7 | 42.1 |
| | S.D. | 0.9 | 7.1 | 5.6 |
| | N | 3 | 3 | 3 |
| Liver (%) | Mean | 1.73 | 1.88 | 1.86 |
| | S.D. | 0.09 | 0.10 | 0.10 |
| | N | 3 | 3 | 3 |
| Spleen (g) | Mean | 1.727 | 3.358 | 3.886 d* |
| | S.D. | 0.520 | 0.758 | 1.087 |
| | N | 3 | 3 | 3 |
| Spleen (%) | Mean | 0.072 | 0.132 | 0.171 d* |
| | S.D. | 0.023 | 0.025 | 0.040 |
| | N | 3 | 3 | 3 |
| Pancreas (g) | Mean | 4.27 | 4.27 | 3.24 |
| | S.D. | 0.54 | 1.20 | 0.38 |
| | N | 3 | 3 | 3 |
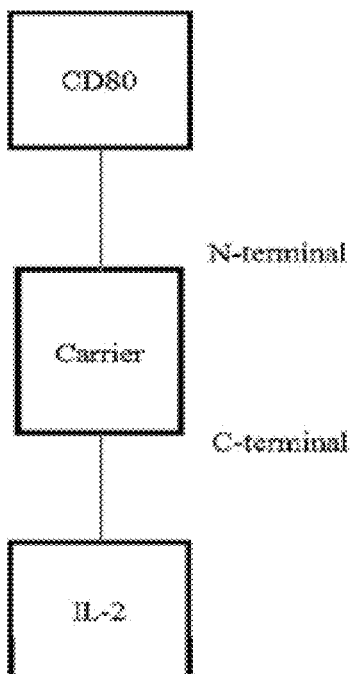
[Fig. 89A]
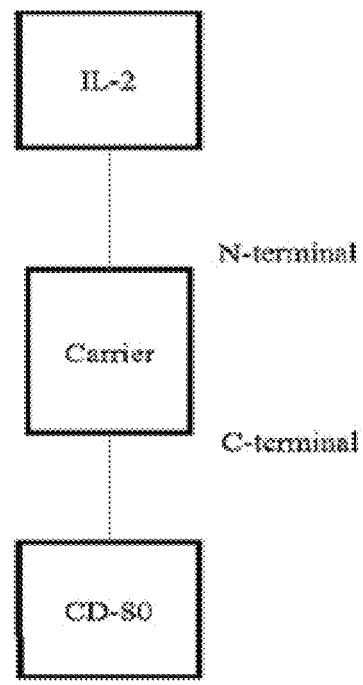
[Fig. 89B]

SEQUENCE LISTING

```
<160> NUMBER OF SEQ ID NOS: 37

<210> SEQ ID NO 1
<211> LENGTH: 25
<212> TYPE: PRT
<213> ORGANISM: Artificial Sequence
<220> FEATURE:
<223> OTHER INFORMATION: signal peptide (TPA)

<400> SEQUENCE: 1

Met Asp Ala Met Leu Arg Gly Leu Cys Cys Val Leu Leu Leu Cys Gly
1               5                   10                  15

Ala Val Phe Val Ser Pro Ser His Ala
            20                  25

<210> SEQ ID NO 2
<211> LENGTH: 208
<212> TYPE: PRT
<213> ORGANISM: Artificial Sequence
```

```
<220> FEATURE:
<223> OTHER INFORMATION: hB7-1:35-242

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
        50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 3
<211> LENGTH: 30
<212> TYPE: PRT
<213> ORGANISM: Artificial Sequence
<220> FEATURE:
<223> OTHER INFORMATION: hinge

<400> SEQUENCE: 3

Gly Ser Gly Gly Gly Ser Gly Gly Gly Ser Gly Gly Gly
1               5                   10                  15

Ser Ala Glu Ser Lys Tyr Gly Pro Pro Cys Pro Pro Cys Pro
                20                  25                  30

<210> SEQ ID NO 4
<211> LENGTH: 216
<212> TYPE: PRT
<213> ORGANISM: Artificial Sequence
<220> FEATURE:
<223> OTHER INFORMATION: immunoglobulin fc

<400> SEQUENCE: 4

Ala Pro Glu Ala Ala Gly Gly Pro Ser Val Phe Leu Phe Pro Pro Lys
1               5                   10                  15

Pro Lys Asp Gln Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45
```

```
Val Asp Gly Val Glu Val His Asn Ala Lys Thr Lys Pro Arg Glu Glu
 50                  55                  60
Gln Phe Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                     85                  90                  95
Gly Leu Pro Ser Ser Ile Glu Lys Thr Ile Ser Lys Ala Lys Gly Gln
                100                 105                 110
Pro Arg Glu Pro Gln Val Tyr Thr Leu Pro Pro Ser Gln Glu Glu Met
                115                 120                 125
Thr Lys Asn Gln Val Ser Leu Thr Cys Leu Val Lys Gly Phe Tyr Pro
130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Arg Leu Thr Val Asp Lys Ser Arg Trp Gln Glu Gly Asn Val
                180                 185                 190
Phe Ser Cys Ser Val Leu His Glu Ala Leu His Asn His Tyr Thr Gln
                195                 200                 205
Lys Ser Leu Ser Leu Ser Leu Gly
    210                 215

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Gly Gly Ser
1               5

<210> SEQ ID NO 6
<211> LENGTH: 133
<212> TYPE: PRT
<213> ORGANISM: Artificial Sequence
<220> FEATURE:
<223> OTHER INFORMATION: hIL-2M

<400> SEQUENCE: 6

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Ala Met Leu Thr Ala Lys Phe Tyr Met Pro Lys
                35                  40                  45
Lys Ala Thr Glu Leu Lys His Leu Gln Cys Leu Glu Glu Glu Leu Lys
 50                  55                  60
Pro Leu Glu Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Cys Gln Ser Ile
            115                 120                 125

Ile Ser Thr Leu Thr
            130

<210> SEQ ID NO 7
<211> LENGTH: 617
<212> TYPE: PRT
<213> ORGANISM: Artificial Sequence
<220> FEATURE:
<223> OTHER INFORMATION: fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
                20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
            260                 265                 270

Val Phe Leu Phe Pro Pro Lys Pro Lys Asp Gln Leu Met Ile Ser Arg
        275                 280                 285

Thr Pro Glu Val Thr Cys Val Val Val Asp Val Ser Gln Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335
```

```
Ser Val Leu Thr Val Leu His Gln Asp Trp Leu Asn Gly Lys Glu Tyr
            340                 345                 350
Lys Cys Lys Val Ser Asn Lys Gly Leu Pro Ser Ser Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Gln Glu Glu Met Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Arg Leu Thr Val Asp Lys Ser
        435                 440                 445
Arg Trp Gln Glu Gly Asn Val Phe Ser Cys Ser Val Leu His Glu Ala
    450                 455                 460
Leu His Asn His Tyr Thr Gln Lys Ser Leu Ser Leu Ser Leu Gly Gly
465                 470                 475                 480
Gly Gly Gly Ser Ala Pro Thr Ser Ser Ser Thr Lys Lys Thr Gln Leu
                485                 490                 495
Gln Leu Glu His Leu Leu Leu Asp Leu Gln Met Ile Leu Asn Gly Ile
            500                 505                 510
Asn Asn Tyr Lys Asn Pro Lys Leu Thr Ala Met Leu Thr Ala Lys Phe
        515                 520                 525
Tyr Met Pro Lys Lys Ala Thr Glu Leu Lys His Leu Gln Cys Leu Glu
    530                 535                 540
Glu Glu Leu Lys Pro Leu Glu Glu Val Leu Asn Leu Ala Gln Ser Lys
545                 550                 555                 560
Asn Phe His Leu Arg Pro Arg Asp Leu Ile Ser Asn Ile Asn Val Ile
                565                 570                 575
Val Leu Glu Leu Lys Gly Ser Glu Thr Thr Phe Met Cys Glu Tyr Ala
            580                 585                 590
Asp Glu Thr Ala Thr Ile Val Glu Phe Leu Asn Arg Trp Ile Thr Phe
        595                 600                 605
Cys Gln Ser Ile Ile Ser Thr Leu Thr
    610                 615

<210> SEQ ID NO 8
<211> LENGTH: 1857
<212> TYPE: DNA
<213> ORGANISM: Artificial Sequence
<220> FEATURE:
<223> OTHER INFORMATION: nucleotiedes coding fusion protein (GI101)

<400> SEQUENCE: 8
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120 tgcggccaca acgtttcagt ggaagaactg cccagacca ggatctactg cagaaagaa      180 aagaaaatgg tgctgaccat gatgtccggc gacatgaaca tctggcctga gtacaagaac     240
cggaccatct tcgacatcac caacaacctg tccatcgtga ttctggccct gaggccttct     300
gatgagggca cctatgagtg cgtggtgctg aagtacgaga aggacgcctt caagcgcgag     360
cacctggctg aagtgacact gtccgtgaag gccgactttc ccacaccttc catctccgac     420
ttcgagatcc ctaccttcaa catccggcgg atcatctgtt ctacctctgg cggctttcct     480
```

```
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg aagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg ccagcctag ggaaccccag   1140 gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt ctttctgtac   1320
tctcgcctga ccgtggacaa gtctagatgg caagagggca acgtgttctc ctgctctgtg   1380
ctgcacgagg ccctgcacaa tcactacacc cagaagtccc tgtctctgtc tcttggaggt   1440
ggtggcggtt ctgccccctac cagctcctct accaagaaaa cccagctcca gttggagcat   1500
ctgctgctgg acctccagat gattctgaac gggatcaaca actataagaa ccccaagctg   1560
accgccatgc tgaccgctaa gttctacatg cccaagaagg ccaccgagct gaagcacctc   1620
cagtgcctgg aagaagaact gaagcccctg aagaggtgc tgaatctggc ccagtccaag   1680
aacttccacc tgaggccacg ggacctgatc agcaacatca cgtgatcgt gctggaactg   1740 aagggctccg agacaacctt tatgtgcgag tacgccgacg agacagccac catcgtggaa   1800
tttctgaacc ggtggatcac cttctgccag agcatcatct ccacactgac ctgatga     1857
```

<210> SEQ ID NO 9
<211> LENGTH: 592
<212> TYPE: PRT
<213> ORGANISM: Artificial Sequence
<220> FEATURE:
<223> OTHER INFORMATION: fusion protein (GI101)

<400> SEQUENCE: 9

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
        50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125
```

-continued

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
530                 535                 540

```
Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 10
<211> LENGTH: 133
<212> TYPE: PRT
<213> ORGANISM: Artificial Sequence
<220> FEATURE:
<223> OTHER INFORMATION: hIL-2

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 11
<211> LENGTH: 288
<212> TYPE: PRT
<213> ORGANISM: Artificial Sequence
<220> FEATURE:
<223> OTHER INFORMATION: CD80

<400> SEQUENCE: 11

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125
```

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 12
<211> LENGTH: 215
<212> TYPE: PRT
<213> ORGANISM: Artificial Sequence
<220> FEATURE:
<223> OTHER INFORMATION: modified Fc

<400> SEQUENCE: 12

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

```
Cys Ser Val Met His Glu Ala Leu His Asn His Tyr Thr Gln Lys Ser
        195                 200                 205
Leu Ser Leu Ser Leu Gly Lys
    210                 215

<210> SEQ ID NO 13
<211> LENGTH: 306
<212> TYPE: PRT
<213> ORGANISM: Artificial Sequence
<220> FEATURE:
<223> OTHER INFORMATION: mCD80

<400> SEQUENCE: 13

Met Ala Cys Asn Cys Gln Leu Met Gln Asp Thr Pro Leu Leu Lys Phe
1               5                   10                  15
Pro Cys Pro Arg Leu Ile Leu Leu Phe Val Leu Leu Ile Arg Leu Ser
                20                  25                  30
Gln Val Ser Ser Asp Val Asp Glu Gln Leu Ser Lys Ser Val Lys Asp
            35                  40                  45
Lys Val Leu Leu Pro Cys Arg Tyr Asn Ser Pro His Glu Asp Glu Ser
    50                  55                  60
Glu Asp Arg Ile Tyr Trp Gln Lys His Asp Lys Val Val Leu Ser Val
65                  70                  75                  80
Ile Ala Gly Lys Leu Lys Val Trp Pro Glu Tyr Lys Asn Arg Thr Leu
                85                  90                  95
Tyr Asp Asn Thr Thr Tyr Ser Leu Ile Ile Leu Gly Leu Val Leu Ser
                100                 105                 110
Asp Arg Gly Thr Tyr Ser Cys Val Val Gln Lys Lys Glu Arg Gly Thr
            115                 120                 125
Tyr Glu Val Lys His Leu Ala Leu Val Lys Leu Ser Ile Lys Ala Asp
    130                 135                 140
Phe Ser Thr Pro Asn Ile Thr Glu Ser Gly Asn Pro Ser Ala Asp Thr
145                 150                 155                 160
Lys Arg Ile Thr Cys Phe Ala Ser Gly Gly Phe Pro Lys Pro Arg Phe
                165                 170                 175
Ser Trp Leu Glu Asn Gly Arg Glu Leu Pro Gly Ile Asn Thr Thr Ile
                180                 185                 190
Ser Gln Asp Pro Glu Ser Glu Leu Tyr Thr Ile Ser Ser Gln Leu Asp
            195                 200                 205
Phe Asn Thr Thr Arg Asn His Thr Ile Lys Cys Leu Ile Lys Tyr Gly
    210                 215                 220
Asp Ala His Val Ser Glu Asp Phe Thr Trp Glu Lys Pro Pro Glu Asp
225                 230                 235                 240
Pro Pro Asp Ser Lys Asn Thr Leu Val Leu Phe Gly Ala Gly Phe Gly
                245                 250                 255
Ala Val Ile Thr Val Val Val Ile Val Val Ile Ile Lys Cys Phe Cys
                260                 265                 270
Lys His Arg Ser Cys Phe Arg Arg Asn Glu Ala Ser Arg Glu Thr Asn
            275                 280                 285
Asn Ser Leu Thr Phe Gly Pro Glu Glu Ala Leu Ala Glu Gln Thr Val
    290                 295                 300
Phe Leu
305
```

<210> SEQ ID NO 14
<211> LENGTH: 1848
<212> TYPE: DNA
<213> ORGANISM: Artificial Sequence
<220> FEATURE:
<223> OTHER INFORMATION: nucleotiedes coding fusion protein (mGI101)

<400> SEQUENCE: 14

```
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240
aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct      480
aagcctcggt tctcttggct ggaaaacggc agagagctgc ccggcatcaa taccaccatt     540
tctcaggacc cagagtccga gctgtacacc atctccagcc agctcgactt aaacaccacc     600
agaaaccaca ccatcaagtg cctgattaag tacggcgacg cccacgtgtc cgaggacttt     660
acttgggaga aacctcctga ggaccctcct gactctggat ctggcggcgg aggttctggc     720
ggaggtggaa gcggaggcgg aggatctgct gagtctaagt atggccctcc ttgtcctcca     780
tgtcctgctc cagaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca caacgccaag     960
accaagccta gagaggaaca gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga accccaggtt    1140
tacaccctgc ctccaagcca agaggaaatg accaagaacc aggtgtccct gacctgcctg    1200
gtcaagggct ctaccccttc cgacattgcc gtggaatggg agtccaatgg ccagcctgag    1260
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtctct ggaggtggt    1440
ggcggttctg cccctaccct cagctctacc aagaaaaccc agctccagtt ggagcatctg    1500
ctgctggacc tccagatgat cctgaatggc atcaacaatt acaagaaccc caagctgacc    1560
gccatgctga ccgctaagtt ctacatgccc aagaaggcca ccgagctgaa gcacttgcag    1620
tgcctggaag aggaactgaa gcccctggaa gaagtgctga atctggccca gtccaagaac    1680
ttccacctga ggcctaggga cctgatctcc aacatcaacg tgatcgtgct ggaactgaaa    1740
ggctccgaga caaccttcat gtgcgagtac gccgacgaga cagccaccat cgtggaattt    1800
ctgaaccggt ggatcacctt ctgccagagc atcatctcca cactgacc               1848
```

<210> SEQ ID NO 15
<211> LENGTH: 616
<212> TYPE: PRT
<213> ORGANISM: Artificial Sequence
<220> FEATURE:
<223> OTHER INFORMATION: fusion protein (mGI101)

<400> SEQUENCE: 15

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415
```

Gly Gln Pro Glu Asn Asn Tyr Lys Thr Thr Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Glu
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615

<210> SEQ ID NO 16
<211> LENGTH: 1437
<212> TYPE: DNA
<213> ORGANISM: Artificial Sequence
<220> FEATURE:
<223> OTHER INFORMATION: nucleotiedes coding fusion protein (GI101C1)

<400> SEQUENCE: 16

| | | | | | |
|---|---|---|---|---|---|
| atggatgcta | tgctgagagg | cctgtgttgc | gtgctgctgc | tgtgtggcgc | tgtgttcgtg | 60 |
| tctccttctc | acgctgtgat | ccacgtgacc | aaagaagtga | agaggtcgc | cacactgtcc | 120 |
| tgcggccaca | cgtttcagt | ggaagaactg | gcccagacca | ggatctactg | cagaaagaa | 180 |
| aagaaaatgg | tgctgaccat | gatgtccggc | gacatgaaca | tctggcctga | gtacaagaac | 240 |
| cggaccatct | tcgacatcac | caacaacctg | tccatcgtga | ttctggccct | gaggccttct | 300 |
| gatgagggca | cctatgagtg | cgtggtgctg | aagtacgaga | ggacgcctt | caagcgcgag | 360 |
| cacctggctg | aagtgacact | gtccgtgaag | gccgactttc | ccacaccttc | catctccgac | 420 |
| ttcgagatcc | ctacctccaa | catccggcgg | atcatctgtt | ctacctctgg | cggctttcct | 480 |
| gagcctcacc | tgtcttggct | ggaaaacggc | gaggaactga | cgccatcaa | caccaccgtg | 540 |
| tctcaggacc | ccgaaaccga | gctgtacgct | gtgtcctcca | gctggactt | caacatgacc | 600 |
| accaaccaca | gcttcatgtg | cctgattaag | tacggccacc | tgagagtgaa | ccagaccttc | 660 |
| aactggaaca | ccaccaagca | agagcacttc | cctgacaatg | gatctggcgg | cggaggttct | 720 |
| ggcggaggtg | gaagcggagg | cggaggatct | gctgagtcta | agtatggccc | tccttgtcct | 780 |
| ccatgtcctg | ctccagaagc | tgctggcgga | ccctctgtgt | tcctgtttcc | tccaaagcct | 840 |
| aaggaccagc | tcatgatctc | tcggacaccc | gaagtgacct | gcgtggtggt | ggatgtgtct | 900 |

-continued

```
caagaggacc ctgaggtgca gttcaattgg tacgtggacg gcgtggaagt gcacaacgcc       960
aagaccaagc ctagagagga acagttcaac tccacctaca gagtggtgtc cgtgctgacc      1020
gtgctgcacc aggattggct gaacggcaaa gagtacaagt gcaaggtgtc caacaagggc      1080 ctgcccttcca gcatcgaaaa gaccatctcc aaggctaagg ccagcctag ggaaccccag      1140 gtttacaccc tgcctccaag ccaagaggaa atgaccaaga accaggtgtc cctgacctgc      1200
ctggtcaagg gcttctaccc ttccgacatt gccgtggaat gggagtccaa tggccagcct      1260
gagaacaact acaagaccac acctcctgtg ctggactccg acggctcctt ctttctgtac      1320
tctcgcctga ccgtggacaa gtctaggtgg caagagggca acgtgttctc ctgctctgtg      1380
ctgcacgagg ccctgcacaa tcactacacc cagaagtccc tgtctctgtc cctgggc        1437
```

<210> SEQ ID NO 17
<211> LENGTH: 454
<212> TYPE: PRT
<213> ORGANISM: Artificial Sequence
<220> FEATURE:
<223> OTHER INFORMATION: fusion protein (GI101C1)

<400> SEQUENCE: 17

```
Val Ile His Val Thr Lys Glu Val Lys Glu Val Ala Thr Leu Ser Cys
1               5                  10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270
```

```
Asp Val Ser Gln Glu Asp Pro Glu Val Gln Phe Asn Trp Tyr Val Asp
            275                 280                 285
Gly Val Glu Val His Asn Ala Lys Thr Lys Pro Arg Glu Glu Gln Phe
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Gly Leu
                325                 330                 335
Pro Ser Ser Ile Glu Lys Thr Ile Ser Lys Ala Lys Gly Gln Pro Arg
            340                 345                 350
Glu Pro Gln Val Tyr Thr Leu Pro Pro Ser Gln Glu Glu Met Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Arg Leu Thr Val Asp Lys Ser Arg Trp Gln Glu Gly Asn Val Phe Ser
            420                 425                 430
Cys Ser Val Leu His Glu Ala Leu His Asn His Tyr Thr Gln Lys Ser
        435                 440                 445
Leu Ser Leu Ser Leu Gly
    450

<210> SEQ ID NO 18
<211> LENGTH: 1176
<212> TYPE: DNA
<213> ORGANISM: Artificial Sequence
<220> FEATURE:
<223> OTHER INFORMATION: nucleotiedes coding fusion protein (GI101C2)

<400> SEQUENCE: 18
atggatgcta tgctgagagg cctgtgttgc gtgctgctgc tgtgtggcgc tgtgttcgtg      60
tctccatctc acgccgctga gtctaagtac ggccctcctt gtcctccatg tcctgctcca     120
gaagctgctg gcggaccctc tgtgttcctg tttcctccaa agcctaagga ccagctcatg     180
atctctcgga cccctgaagt gacctgcgtg tggtggatg tgtctcaaga ggaccctgag     240
gtgcagttca attggtacgt ggacggcgtg gaagtgcaca acgccaagac caagcctaga     300
gaggaacagt tcaactccac ctacagagtg gtgtccgtgc tgaccgtgct gcaccaggat     360
tggctgaacg gcaaagagta caagtgcaag gtgtccaaca agggcctgcc ttccagcatc     420
gaaaagacca tctccaaggc taagggccag cctagggaac ccaggtttta cacctgcct     480 ccaagccaag aggaaatgac caagaaccag gtgtccctga cctgcctggt caagggcttc     540
tacccttccg acattgccgt ggaatgggag tccaatggcc agcctgagaa caactacaag     600
accacacctc ctgtgctgga ctccgacggc tccttctttc tgtactctcg cctgaccgtg     660
gacaagtcta ggtggcaaga gggcaacgtg ttctcctgct ctgtgctgca cgaggccctg     720
cacaatcact acacccagaa gtccctgtct ctgtctcttg gcggaggcgg aggatctgct     780
cctacctcca gctccaccaa gaaaacccag ctccagttgg agcatctgct gctggacctc     840
cagatgatcc tgaatggcat caacaattac aagaaccca agctgaccgc catgctgacc     900
gctaagttct acatgcccaa gaaggccacc gagctgaagc acctccagtg cctggaagag     960
gaactgaagc ccctggaaga agtgctgaat ctggcccagt ccaagaactt ccacctgagg    1020
```

-continued

```
cctagggacc tgatctccaa catcaacgtg atcgtgctgg aactgaaagg ctccgagaca      1080
accttcatgt gcgagtacgc cgacgagaca gccaccatcg tggaatttct gaaccggtgg      1140
atcaccttct gccagtccat catctccaca ctgacc                                1176
```

<210> SEQ ID NO 19
<211> LENGTH: 367
<212> TYPE: PRT
<213> ORGANISM: Artificial Sequence
<220> FEATURE:
<223> OTHER INFORMATION: fusion protein (GI101C2)

<400> SEQUENCE: 19

```
Ala Glu Ser Lys Tyr Gly Pro Pro Cys Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220

Ser Leu Ser Leu Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Ala
            260                 265                 270

Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335
```

```
Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365

<210> SEQ ID NO 20
<211> LENGTH: 1434
<212> TYPE: DNA
<213> ORGANISM: Artificial Sequence
<220> FEATURE:
<223> OTHER INFORMATION: nucleotiedes coding fusion protein (mGI101C1)

<400> SEQUENCE: 20
atggatgcta tgctgagagg cctgtgttgc gtgctgctgc tgtgtggcgc tgtgttcgtg    60
tctccttctc acgctgtgga cgagcagctc tccaagtccg tgaaggataa ggtcctgctg   120
ccttgccggt acaactctcc tcacgaggac gagtctgagg accggatcta ctggcagaaa   180
cacgacaagg tggtgctgtc cgtgatcgcc ggaaagctga agtgtggcc tgagtacaag    240 aacaggaccc tgtacgacaa caccacctac agcctgatca tcctgggcct cgtgctgagc   300
gatagaggca ctattcttg cgtggtgcag aagaaagagc ggggcaccta cgaagtgaag    360
cacctggctc tggtcaagct gtccatcaag gccgacttca gcacccctaa catcaccgag   420
tctggcaacc cttccgccga caccaagaga atcacctgtt cgcctctgg cggcttccct    480 aagcctcggt tctcttggct ggaaaacggc agagagctgc ccggcatcaa taccaccatt   540
tctcaggacc cagagtccga gctgtacacc atctccagcc agctcgactt aacaccacc    600 agaaaccaca ccatcaagtg cctgattaag tacggcgacg cccacgtgtc cgaggacttt   660
acttgggaga aacctcctga ggaccctcct gactctggat ctggcggcgg aggttctggc   720
ggaggtggaa gcgaggcgg aggatctgct gagtctaagt atggccctcc ttgtcctcca   780
tgtcctgctc cagaagctgc tggcggaccc tctgtgttcc tgtttcctcc aaagcctaag   840
gaccagctca tgatctctcg gaccctgaa gtgacctgcg tggtggtgga tgtgtctcaa    900
gaggaccctg aggtgcagtt caattggtac gtggacggcg tggaagtgca aacgccaag    960 accaagccta gagaggaaca gttcaactcc acctatagag tggtgtccgt gctgaccgtg   1020
ctgcaccagg attggctgaa cggcaaagag tacaagtgca aggtgtccaa caagggcctg   1080
ccttccagca tcgaaaagac catcagcaag gctaagggcc agcctaggga accccaggtt   1140
tacaccctgc ctccaagcca gaggaaatg accaagaacc aggtgtccct gacctgcctg   1200
gtcaagggct ctaccccttc cgacattgcc gtgaatggg agtccaatgg ccagcctgag   1260
aacaactaca agaccacacc tcctgtgctg gactccgacg gctccttctt tctgtactct   1320
cgcctgaccg tggacaagtc taggtggcaa gagggcaacg tgttctcctg ctctgtgctg   1380
cacgaggctc tgcacaacca ctacacccag aagtccctgt ctctgtccct gggc        1434

<210> SEQ ID NO 21
<211> LENGTH: 478
<212> TYPE: PRT
<213> ORGANISM: Artificial Sequence
<220> FEATURE:
<223> OTHER INFORMATION: fusion protein (mGI101C1)

<400> SEQUENCE: 21

Met Asp Ala Met Leu Arg Gly Leu Cys Cys Val Leu Leu Cys Gly
1               5                   10                  15

Ala Val Phe Val Ser Pro Ser His Ala Val Asp Glu Gln Leu Ser Lys
                20                  25                  30
```

```
Ser Val Lys Asp Lys Val Leu Leu Pro Cys Arg Tyr Asn Ser Pro His
         35                  40                  45

Glu Asp Glu Ser Glu Asp Arg Ile Tyr Trp Gln Lys His Asp Lys Val
 50                  55                  60

Val Leu Ser Val Ile Ala Gly Lys Leu Lys Val Trp Pro Glu Tyr Lys
 65                  70                  75                  80

Asn Arg Thr Leu Tyr Asp Asn Thr Thr Tyr Ser Leu Ile Ile Leu Gly
                 85                  90                  95

Leu Val Leu Ser Asp Arg Gly Thr Tyr Ser Cys Val Val Gln Lys Lys
                100                 105                 110

Glu Arg Gly Thr Tyr Glu Val Lys His Leu Ala Leu Val Lys Leu Ser
                115                 120                 125

Ile Lys Ala Asp Phe Ser Thr Pro Asn Ile Thr Glu Ser Gly Asn Pro
130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
                180                 185                 190

Ser Gln Leu Asp Phe Asn Thr Thr Arg Asn His Thr Ile Lys Cys Leu
                195                 200                 205

Ile Lys Tyr Gly Asp Ala His Val Ser Glu Asp Phe Thr Trp Glu Lys
210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
                260                 265                 270

Phe Leu Phe Pro Pro Lys Pro Lys Asp Gln Leu Met Ile Ser Arg Thr
                275                 280                 285

Pro Glu Val Thr Cys Val Val Val Asp Val Ser Gln Glu Asp Pro Glu
                290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Gly Leu Pro Ser Ser Ile Glu Lys Thr Ile
                355                 360                 365

Ser Lys Ala Lys Gly Gln Pro Arg Glu Pro Gln Val Tyr Thr Leu Pro
                370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Arg Leu Thr Val Asp Lys Ser Arg
                435                 440                 445
```

-continued

Trp Gln Glu Gly Asn Val Phe Ser Cys Ser Val Leu His Glu Ala Leu
            450                 455                 460

His Asn His Tyr Thr Gln Lys Ser Leu Ser Leu Gly
465                 470                 475

<210> SEQ ID NO 22
<211> LENGTH: 133
<212> TYPE: PRT
<213> ORGANISM: Artificial Sequence
<220> FEATURE:
<223> OTHER INFORMATION: variants of IL-2 (3M, M45)

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 23
<211> LENGTH: 133
<212> TYPE: PRT
<213> ORGANISM: Artificial Sequence
<220> FEATURE:
<223> OTHER INFORMATION: variants of IL-2 (3M, M61)

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

```
<210> SEQ ID NO 24
<211> LENGTH: 133
<212> TYPE: PRT
<213> ORGANISM: Artificial Sequence
<220> FEATURE:
<223> OTHER INFORMATION: variants of IL-2 (3M, M72)

<400> SEQUENCE: 24

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
            130

<210> SEQ ID NO 25
<211> LENGTH: 1851
<212> TYPE: DNA
<213> ORGANISM: Artificial Sequence
<220> FEATURE:
<223> OTHER INFORMATION: nucleotiedes coding fusion protein (GI102-M45)

<400> SEQUENCE: 25
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120 tgcggccaca acgtttcagt ggaagaactg gcccagacca ggatctactg cagaaagaa      180 aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540 tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg gaagcggagg cggaggatct gctgagtcta gtatggccc tccttgtcct      780 ccatgtcctg ctccagaagc tgctggcgga ccctctgtgt tcctgttttcc tccaaagcct      840 aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gtggtgtgtc cgtgctgacc      1020
```

-continued

```
gtgctgcacc aggattggct gaacggcaaa gagtacaagt gcaaggtgtc caacaagggc    1080
ctgccttcca gcatcgaaaa gaccatctcc aaggctaagg ccagcctag ggaaccccag     1140 gtttacaccc tgcctccaag ccaagaggaa atgaccaaga accaggtgtc cctgacctgc    1200
ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctagatgg caagagggca acgtgttctc ctgctctgtg    1380
ctgcacgagg ccctgcacaa tcactacacc cagaagtccc tgtctctgtc tcttggaggt    1440
ggtggcggtt ctgcccctac cagctcctct accaagaaaa cccagctcca gttggagcat    1500
ctgctgctgg acctccagat gattctgaac gggatcaaca actataagaa ccccaagctg    1560
accgccatgc tgaccgctaa gttcgccatg cccaagaagg ccaccgagct gaagcacctc    1620
cagtgcctgg aagaagaact gaagcccctg aagaggtgc tgaatctggc ccagtccaag    1680
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac c             1851
```

<210> SEQ ID NO 26
<211> LENGTH: 592
<212> TYPE: PRT
<213> ORGANISM: Artificial Sequence
<220> FEATURE:
<223> OTHER INFORMATION: fusion protein (GI102-M45)

<400> SEQUENCE: 26

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220
```

```
Ser Ala Glu Ser Lys Tyr Gly Pro Pro Cys Pro Cys Pro Ala Pro
225                 230                 235                 240

Glu Ala Ala Gly Gly Pro Ser Val Phe Leu Phe Pro Pro Lys Pro Lys
            245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 27
<211> LENGTH: 1851
<212> TYPE: DNA
<213> ORGANISM: Artificial Sequence
<220> FEATURE:
<223> OTHER INFORMATION: nucleotiedes coding fusion protein (GI102-M61)

<400> SEQUENCE: 27

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120
tgcggccaca acgtttcagt ggaagaactg gcccagacca ggatctactg cagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga acgccatcaa ccaccaccgtg     540
tctcaggacc ccgaaaccga gctgtacgct gtgtcctcca gctggacttt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg aagcggagg cggaggatct gctgagtcta gtatgggccc tccttgtcct      780
ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc tagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg ccagcctag gaaccccag      1140
gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca acgtgttctc ctgctctgtg     1380
ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca actataagaa cccccaagctg    1560
accgccatgc tgaccgctaa gttctacatg cccaagaagg ccaccgagct gaagcacctc     1620
cagtgcctgg aaagggaact gaagcccctg gaagaggtgc tgaatctggc ccagtccaag     1680
aacttccacc tgaggccacg ggacctgatc agcaacatca acgtgatcgt gctggaactg     1740
aagggctccg agacaacctt tatgtgcgag tacgccgacg agacagccac catcgtggaa     1800
tttctgaacc ggtggatcac cttctgccag agcatcatct ccacactgac c             1851
```

<210> SEQ ID NO 28
<211> LENGTH: 592
<212> TYPE: PRT
<213> ORGANISM: Artificial Sequence
<220> FEATURE:
<223> OTHER INFORMATION: fusion protein (GI102-M61)

<400> SEQUENCE: 28

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

-continued

```
Gln Lys Glu Lys Lys Met Val Leu Thr Met Met Ser Gly Asp Met Asn
         35                  40                  45
Ile Trp Pro Glu Tyr Lys Asn Arg Thr Ile Phe Asp Ile Thr Asn Asn
 50                  55                  60
Leu Ser Ile Val Ile Leu Ala Leu Arg Pro Ser Asp Glu Gly Thr Tyr
 65                  70                  75                  80
Glu Cys Val Val Leu Lys Tyr Glu Lys Asp Ala Phe Lys Arg Glu His
                 85                  90                  95
Leu Ala Glu Val Thr Leu Ser Val Lys Ala Asp Phe Pro Thr Pro Ser
                100                 105                 110
Ile Ser Asp Phe Glu Ile Pro Thr Ser Asn Ile Arg Arg Ile Ile Cys
            115                 120                 125
Ser Thr Ser Gly Gly Phe Pro Glu Pro His Leu Ser Trp Leu Glu Asn
130                 135                 140
Gly Glu Glu Leu Asn Ala Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
            180                 185                 190
Gln Thr Phe Asn Trp Asn Thr Thr Lys Gln Glu His Phe Pro Asp Asn
        195                 200                 205
Gly Ser Gly Gly Gly Ser Gly Gly Gly Ser Gly Gly Gly Gly
        210                 215                 220
Ser Ala Glu Ser Lys Tyr Gly Pro Pro Cys Pro Pro Cys Pro Ala Pro
225                 230                 235                 240
Glu Ala Ala Gly Gly Pro Ser Val Phe Leu Phe Pro Pro Lys Pro Lys
                245                 250                 255
Asp Gln Leu Met Ile Ser Arg Thr Pro Glu Val Thr Cys Val Val Val
            260                 265                 270
Asp Val Ser Gln Glu Asp Pro Glu Val Gln Phe Asn Trp Tyr Val Asp
        275                 280                 285
Gly Val Glu Val His Asn Ala Lys Thr Lys Pro Arg Glu Glu Gln Phe
290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Gly Leu
                325                 330                 335
Pro Ser Ser Ile Glu Lys Thr Ile Ser Lys Ala Lys Gly Gln Pro Arg
            340                 345                 350
Glu Pro Gln Val Tyr Thr Leu Pro Pro Ser Gln Glu Glu Met Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Arg Leu Thr Val Asp Lys Ser Arg Trp Gln Glu Gly Asn Val Phe Ser
            420                 425                 430
Cys Ser Val Leu His Glu Ala Leu His Asn His Tyr Thr Gln Lys Ser
        435                 440                 445
```

Leu Ser Leu Ser Leu Gly Gly Gly Gly Ser Ala Pro Thr Ser Ser
              450                 455                 460

Ser Thr Lys Lys Thr Gln Leu Gln Leu Glu His Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Arg Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 29
<211> LENGTH: 1857
<212> TYPE: DNA
<213> ORGANISM: Artificial Sequence
<220> FEATURE:
<223> OTHER INFORMATION: nucleotiedes coding fusion protein (GI102-M72)

<400> SEQUENCE: 29

| | | |
|---|---|---|
| atggatgcta tgctgagagg cctgtgttgc gtgctgctgc tgtgtggcgc tgtgttcgtg | 60 |
| tctccttctc acgctgtgat ccacgtgacc aaagaagtga agaggtcgc cacactgtcc | 120 |
| tgcggccaca acgtttcagt ggaagaactg gcccagacca ggatctactg cagaaagaa | 180 |
| aagaaaatgg tgctgaccat gatgtccggc gacatgaaca tctggcctga gtacaagaac | 240 |
| cggaccatct tcgacatcac caacaacctg tccatcgtga ttctggccct gaggccttct | 300 |
| gatgagggca cctatgagtg cgtggtgctg aagtacgaga aggacgcctt caagcgcgag | 360 |
| cacctggctg aagtgacact gtccgtgaag gccgactttc ccacaccttc catctccgac | 420 |
| ttcgagatcc ctacctccaa catccggcgg atcatctgtt ctacctctgg cggctttcct | 480 |
| gagcctcacc tgtcttggct ggaaaacggc gaggaactga acgccatcaa caccaccgtg | 540 |
| tctcaggacc ccgaaaccga gctgtacgct gtgtcctcca gctggactt caacatgacc | 600 |
| accaaccaca gcttcatgtg cctgattaag tacggccacc tgagagtgaa ccagaccttc | 660 |
| aactggaaca ccaccaagca agagcacttc cctgacaatg gatctggcgg cggaggttct | 720 |
| ggcggaggtg gaagcggagg cggaggatct gctgagtcta agtatggccc ccttgtcct | 780 |
| ccatgtcctg ctccagaagc tgctggcgga ccctctgtgt tcctgttccc tccaaagcct | 840 |
| aaggaccagc tcatgatctc tcggacaccc gaagtgacct gcgtggtggt ggatgtgtct | 900 |
| caagaggacc ctgaggtgca gttcaattgg tacgtggacg gcgtggaagt gcacaacgcc | 960 |
| aagaccaagc tagagagga acagttcaac tccacctaca gagtggtgtc cgtgctgacc | 1020 |
| gtgctgcacc aggattggct gaacggcaaa gagtacaagt gcaaggtgtc caacaagggc | 1080 |
| ctgccttcca gatcgaaaa gaccatctcc aaggctaagg ccagcctag gaaccccag | 1140 |
| gtttacaccc tgcctccaag ccaagaggaa atgaccaaga accaggtgtc cctgacctgc | 1200 |
| ctggtcaagg gcttctaccc ttccgacatt gccgtggaat gggagtccaa tggccagcct | 1260 |

-continued

```
gagaacaact acaagaccac acctcctgtg ctggactccg acggctcctt ctttctgtac    1320
tctcgcctga ccgtggacaa gtctagatgg caagagggca acgtgttctc ctgctctgtg    1380
ctgcacgagg ccctgcacaa tcactacacc cagaagtccc tgtctctgtc tcttggaggt    1440
ggtggcggtt ctgccoctac cagctcctct accaagaaaa cccagctcca gttggagcat    1500
ctgctgctgg acctccagat gattctgaac gggatcaaca actataagaa ccccaagctg    1560
accgccatgc tgaccgctaa gttctacatg cccaagaagg ccaccgagct gaagcacctc    1620
cagtgcctgg aagaagaact gaagcccctg aagaggtgc tgaatggggc ccagtccaag    1680
aacttccacc tgaggccacg ggacctgatc agcaacatca cgtgatcgt gctggaactg    1740 aagggctccg agacaacctt tatgtgcgag tacgccgacg agacagccac catcgtggaa    1800
tttctgaacc ggtggatcac cttctgccag agcatcatct ccacactgac ctgatga      1857
```

<210> SEQ ID NO 30
<211> LENGTH: 592
<212> TYPE: PRT
<213> ORGANISM: Artificial Sequence
<220> FEATURE:
<223> OTHER INFORMATION: fusion protein (GI102-M72)

<400> SEQUENCE: 30

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270
```

```
Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 31
<211> LENGTH: 1851
<212> TYPE: DNA
<213> ORGANISM: Artificial Sequence
<220> FEATURE:
<223> OTHER INFORMATION: nucleotiedes coding fusion protein (GI101w)

<400> SEQUENCE: 31
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120 tgcggccaca acgtttcagt ggaagaactg cccagacca ggatctactg cagaaagaa      180 aagaaaatgg tgctgaccat gatgtccggc gacatgaaca tctggcctga gtacaagaac     240
cggaccatct tcgacatcac caacaacctg tccatcgtga ttctggccct gaggccttct     300
```

```
gatgaggca cctatgagtg cgtggtgctg aagtacgaga aggacgcctt caagcgcgag      360
cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga acgccatcaa caccaccgtg      540
tctcaggacc ccgaaaccga gctgtacgct gtgtcctcca agctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg aagcggaggc ggaggatct gctgagtcta agtatggccc tccttgtcct      780
ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg gccagcctag ggaaccccag     1140
gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca acgtgttctc ctgctctgtg     1380
ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca actataagaa ccccaagctg     1560
acccgcatgc tgacctttaa gttctacatg cccaagaagg ccaccgagct gaagcacctc     1620
cagtgcctga agaagaaact gaagcccctg aagaggtgc tgaatctggc ccagtccaag     1680
aacttccacc tgaggccacg ggacctgatc agcaacatca cgtgatcgt gctggaactg     1740
aagggctccg agacaacctt tatgtgcgag tacgccgacg agacagccac catcgtggaa     1800
tttctgaacc ggtggatcac cttctgccag agcatcatct ccacactgac c              1851
```

<210> SEQ ID NO 32
<211> LENGTH: 592
<212> TYPE: PRT
<213> ORGANISM: Artificial Sequence
<220> FEATURE:
<223> OTHER INFORMATION: fusion protein (GI101w)

<400> SEQUENCE: 32

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95
```

```
Leu Ala Glu Val Thr Leu Ser Val Lys Ala Asp Phe Pro Thr Pro Ser
                100                 105                 110
Ile Ser Asp Phe Glu Ile Pro Thr Ser Asn Ile Arg Arg Ile Ile Cys
            115                 120                 125
Ser Thr Ser Gly Gly Phe Pro Glu Pro His Leu Ser Trp Leu Glu Asn
        130                 135                 140
Gly Glu Glu Leu Asn Ala Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
            180                 185                 190
Gln Thr Phe Asn Trp Asn Thr Thr Lys Gln Glu His Phe Pro Asp Asn
        195                 200                 205
Gly Ser Gly Gly Gly Ser Gly Gly Gly Ser Gly Gly Gly Gly
210                 215                 220
Ser Ala Glu Ser Lys Tyr Gly Pro Pro Cys Pro Pro Cys Pro Ala Pro
225                 230                 235                 240
Glu Ala Ala Gly Gly Pro Ser Val Phe Leu Phe Pro Pro Lys Pro Lys
                245                 250                 255
Asp Gln Leu Met Ile Ser Arg Thr Pro Glu Val Thr Cys Val Val Val
            260                 265                 270
Asp Val Ser Gln Glu Asp Pro Glu Val Gln Phe Asn Trp Tyr Val Asp
        275                 280                 285
Gly Val Glu Val His Asn Ala Lys Thr Lys Pro Arg Glu Glu Gln Phe
290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Gly Leu
                325                 330                 335
Pro Ser Ser Ile Glu Lys Thr Ile Ser Lys Ala Lys Gly Gln Pro Arg
            340                 345                 350
Glu Pro Gln Val Tyr Thr Leu Pro Pro Ser Gln Glu Glu Met Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Arg Leu Thr Val Asp Lys Ser Arg Trp Gln Glu Gly Asn Val Phe Ser
            420                 425                 430
Cys Ser Val Leu His Glu Ala Leu His Asn His Tyr Thr Gln Lys Ser
        435                 440                 445
Leu Ser Leu Ser Leu Gly Gly Gly Gly Ser Ala Pro Thr Ser Ser
450                 455                 460
Ser Thr Lys Lys Thr Gln Leu Gln Leu Glu His Leu Leu Leu Asp Leu
465                 470                 475                 480
Gln Met Ile Leu Asn Gly Ile Asn Asn Tyr Lys Asn Pro Lys Leu Thr
                485                 490                 495
Arg Met Leu Thr Phe Lys Phe Tyr Met Pro Lys Lys Ala Thr Glu Leu
            500                 505                 510
```

```
Lys His Leu Gln Cys Leu Glu Glu Leu Lys Pro Leu Glu Glu Val
            515                 520                 525

Leu Asn Leu Ala Gln Ser Lys Asn Phe His Leu Arg Pro Arg Asp Leu
            530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 33
<211> LENGTH: 1848
<212> TYPE: DNA
<213> ORGANISM: Artificial Sequence
<220> FEATURE:
<223> OTHER INFORMATION: nucleotiedes coding fusion protein (mGI102-M61)

<400> SEQUENCE: 33
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcaccccta a catcaccgag    420 tctggcaacc cttccgccga caccaagaga atcacctgtt cgcctctgg cggcttccct     480 aagcctcggt tctcttggct ggaaaacggc agagagctgc ccggcatcaa taccaccatt     540
tctcaggacc cagagtccga gctgtacacc atctccagcc agctcgactt taacaccacc     600
agaaaccaca ccatcaagtg cctgattaag tacggcgacg cccacgtgtc cgaggacttt     660
acttgggaga aacctcctga ggaccctcct gactctggat ctggcggcgg aggttctggc     720
ggaggtggaa gcggaggcgg aggatctgct gagtctaagt atgggccctcc ttgtcctcca     780 tgtcctgctc cagaagctgc tggcggaccc tctgtgttcc tgtttcctcc aaagcctaag     840
gaccagctca tgatctctcg gacccctgaa gtgacctgcg tggtggtgga tgtgtctcaa     900
gaggaccctg aggtgcagtt caattggtac gtggacggcg tggaagtgca aacgccaag      960 accaagccta gagaggaaca gttcaactcc acctatagag tggtgtccgt gctgaccgtg    1020
ctgcaccagg attggctgaa cggcaaagag tacaagtgca aggtgtccaa caagggcctg    1080
ccttccagca tcgaaaagac catcagcaag gctaagggcc agcctaggga ccccaggtt     1140 tacaccctgc ctccaagcca agaggaaatg accaagaacc aggtgtccct gacctgcctg    1200
gtcaagggct ctaccccttc cgacattgcc gtggaatggg agtccaatgg ccagcctgag    1260
aacaactaca agaccacacc tcctgtgctg gactccgacg gctccttctt tctgtactct    1320
cgcctgaccg tggacaagtc taggtggcaa gagggcaacg tgttctcctg ctctgtgctg    1380
cacgaggctc tgcacaacca ctacacccag aagtccctgt ctctgtctct ggaggtggt     1440 ggcggttctg cccctacctc cagctctacc aagaaaaccc agctccagtt ggagcatctg    1500
ctgctggacc tccagatgat cctgaatggg atcaacaatt acaagaaccc caagctgacc    1560
gccatgctga ccgctaagtt ctacatgccc aagaaggcca ccgagctgaa gcacttgcag    1620
```

```
tgcctggaaa gggaactgaa gcccctggaa gaagtgctga atctggccca gtccaagaac    1680
ttccacctga ggcctaggga cctgatctcc aacatcaacg tgatcgtgct ggaactgaaa    1740
ggctccgaga caaccttcat gtgcgagtac gccgacgaga cagccaccat cgtggaattt    1800
ctgaaccggt ggatcacctt ctgccagagc atcatctcca cactgacc                1848
```

<210> SEQ ID NO 34
<211> LENGTH: 616
<212> TYPE: PRT
<213> ORGANISM: Artificial Sequence
<220> FEATURE:
<223> OTHER INFORMATION: fusion protein (mGI102-M61)

<400> SEQUENCE: 34

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Ser Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320
```

```
Thr Lys Pro Arg Glu Glu Gln Phe Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
            355                 360                 365

Ser Lys Ala Lys Gly Gln Pro Arg Glu Pro Gln Val Tyr Thr Leu Pro
        370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Arg Met Leu Thr Ala Lys Phe Tyr
        515                 520                 525

Met Pro Lys Lys Ala Thr Glu Leu Lys His Leu Gln Cys Leu Glu Arg
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
        610                 615

<210> SEQ ID NO 35
<211> LENGTH: 153
<212> TYPE: PRT
<213> ORGANISM: Artificial Sequence
<220> FEATURE:
<223> OTHER INFORMATION: wild type hIL-2

<400> SEQUENCE: 35

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60
```

```
Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 36
<211> LENGTH: 158
<212> TYPE: PRT
<213> ORGANISM: Artificial Sequence
<220> FEATURE:
<223> OTHER INFORMATION: IL-2 with signal sequence

<400> SEQUENCE: 36

Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
                20                  25                  30

Lys Lys Thr Gln Leu Gln Leu Glu His Leu Leu Leu Asp Leu Gln Met
            35                  40                  45

Ile Leu Asn Gly Ile Asn Asn Tyr Lys Asn Pro Lys Leu Thr Arg Met
        50                  55                  60

Leu Thr Phe Lys Phe Tyr Met Pro Lys Lys Ala Thr Glu Leu Lys His
 65                  70                  75                  80

Leu Gln Cys Leu Glu Glu Glu Leu Lys Pro Leu Glu Glu Val Leu Asn
                 85                  90                  95

Leu Ala Gln Ser Lys Asn Phe His Leu Arg Pro Arg Asp Leu Ile Ser
            100                 105                 110

Asn Ile Asn Val Ile Val Leu Glu Leu Lys Gly Ser Glu Thr Thr Phe
        115                 120                 125

Met Cys Glu Tyr Ala Asp Glu Thr Ala Thr Ile Val Glu Phe Leu Asn
    130                 135                 140

Arg Trp Ile Thr Phe Cys Gln Ser Ile Ile Ser Thr Leu Thr
145                 150                 155

<210> SEQ ID NO 37
<211> LENGTH: 474
<212> TYPE: DNA
<213> ORGANISM: Artificial Sequence
<220> FEATURE:
<223> OTHER INFORMATION: nucleotide sequence coding IL-2 with signal
      sequence

<400> SEQUENCE: 37
atggatgcta tgctgagagg cctgtgttgc gtgctgctgc tgtgtggcgc tgtgttcgtg      60
tctccttctc acgctgcccc taccagctcc tctaccaaga aaacccagct ccagttggag     120
catctgctgc tggacctcca gatgattctg aacgggatca acaactataa gaaccccaag     180
ctgacccgca tgctgacctt taagttctac atgcccaaga aggccaccga gctgaagcac     240
ctccagtgcc tggaagaaga actgaagccc tggaagaggt gctgaatct ggcccagtcc     300
```

```
aagaacttcc acctgaggcc acgggacctg atcagcaaca tcaacgtgat cgtgctggaa      360
ctgaagggct ccgagacaac ctttatgtgc gagtacgccg acgagacagc caccatcgtg      420
gaatttctga accggtggat caccttctgc cagagcatca tctccacact gacc            474
```

FUSION PROTEIN COMPRISING IL-2 PROTEIN AND CD80 PROTEIN, AND USE THEREOF

CROSS REFERENCE TO RELATED APPLICATIONS

This application is a National Stage of International Application No. PCT/KR2019/011928 filed Sep. 16, 2019, claiming priority based on Korean Patent Application No. 10-2018-0110698 filed Sep. 17, 2018, Korean Patent Application No. 10-2019-0001867 filed Jan. 7, 2019, U.S. Provisional Patent Application No. 62/832,013 filed Apr. 10, 2019, and Korean Patent Application No. 10-2019-0053436 filed May 8, 2019.

TECHNICAL FIELD

The present invention relates to a fusion protein comprising an IL-2 protein and a CD80 protein, and a use thereof. Specifically, the present invention relates to a novel fusion protein having cancer therapeutic and immunopotentiating efficacy.

BACKGROUND ART

Interleukin 2 (IL-2), also called T-cell growth factor (TCGF), is a globular glycoprotein that plays a central role in lymphocyte production, survival, and homeostasis. IL-2 has a protein size of 15.5 kDa to 16 kDa and consists of 133 amino acids. IL-2 mediates various immune actions by binding to an IL-2 receptor composed of three distinct subunits.

In addition, IL-2 is synthesized mainly by activated T cells, in particular by CD4+ helper T cells. IL-2 stimulates proliferation and differentiation of T cells, and induces production of cytotoxic T lymphocytes (CTLs) and differentiation of peripheral blood lymphocytes into cytotoxic cells and lymphokine-activated killer cells (LAK cells).

Furthermore, IL-2 is involved in proliferation and differentiation of B cells, promotes immunoglobulin synthesis by B cells, and stimulates production, proliferation, and activation of natural killer cells (NK cells). Therefore, IL-2 is used as an anticancer agent, because it can increase lymphocyte populations and increase the function of the immune cells in the living body. Currently, therapy with IL-2 has been approved and used for patients with metastatic renal cell carcinoma and malignant melanoma.

However, IL-2 has a dual function in immune responses in that it is important not only for mediating an increase in number of immune cells and activity thereof, but also for maintaining immune tolerance. In addition, it has been reported that IL-2 may not be optimal for inhibiting tumor growth. The reason is that in the presence of IL-2, activation-induced cell death (AICD) may occur in the resulting cytotoxic T lymphocytes and immune responses may be inhibited by IL-2-dependent regulatory T cells (Treg cells) (Imai et al., Cancer Sci 98, 416-423, 2007).

In addition, severe cardiovascular, pulmonary, renal, hepatic, gastrointestinal, neuronal, cutaneous, hematological, and systemic side effects occur in patients who have received immunotherapy with IL-2. Therefore, various IL-2 mutations have been studied to improve therapeutic efficacy of IL-2 and minimize side effects thereof (U.S. Pat. No. 5,229,109 B). However, there are still many problems to be solved in order to utilize IL-2 for pharmacological purposes.

Meanwhile, CD80, also known as B7-1, is a member of the B7 family of membrane-bound proteins that are involved in immune regulation by binding to its ligand by way of delivering costimulatory responses and coinhibitory responses. CD80 is a transmembrane protein expressed on the surface of T cells, B cells, dendritic cells, and monocytes. CD80 is known to bind CD28, CTLA4 (CD152), and PD-L1. CD80, CD86, CTLA4, and CD28 are involved in a costimulatory-coinhibitory system. For example, they regulate activity of T cells and are involved in proliferation, differentiation, and survival thereof.

For example, when CD80 and CD86 interact with CD28, costimulatory signals are generated to activate T cells. Eventually, CD80 binds to CTLA4 and stimulates CTLA4 to be upregulated. As a result, CD80 inhibits T cell responses prior to immune response activation caused by CD80/CD28 interaction. This feedback loop allows for fine regulation of immune responses.

In addition, CD80 is known to bind PD-L1, another B7 family member, with affinity similar to that with which CD28 binds PD-L1. PD-L1 is known as one of two ligands for programmed death-1 (PD-1) protein, and PD-L1 is known to be involved in T cell regulation. Binding of CD80 to PD-L1 is another mechanism that can block PD-1/PD-L1 interaction, which may prevent inhibition of T cell responses in tumors. At the same time, however, an increase in CD80 levels causes CD80 to bind to CD28 so that CTLA4 is induced, thereby inducing or inhibiting T cell responses.

DISCLOSURE OF INVENTION

Technical Problem

The present inventors have studied to develop IL-2 which is safe and effective.

As a result, the present inventors have discovered that a novel fusion protein comprising, in one molecule, an IL-2 protein and a CD80 protein can activate immune cells and effectively regulate Treg cells, thereby completing the present invention.

Solution to Problem

In order to achieve the above object, in an aspect of the present invention, there is provided a fusion protein comprising an IL-2 protein and a CD80 protein.

In another aspect of the present invention, there is provided a fusion protein dimer obtained by attaching the two fusion proteins to each other.

In yet another aspect of the present invention, there is provided a polynucleotide encoding the fusion protein.

In still yet another aspect of the present invention, there is provided a vector comprising the polynucleotide.

In still yet another aspect of the present invention, there is provided a transformed cell into which the vector has been introduced.

In still yet another aspect of the present invention, there is provided a pharmaceutical composition for preventing or treating cancer or an infectious disease, comprising, as an active ingredient, the fusion protein or the fusion protein dimer.

In still yet another aspect of the present invention, there is provided a use of the fusion protein for treatment of cancer or an infectious disease.

In still yet another aspect of the present invention, there is provided a use of the fusion protein for manufacture of a medicament for treating cancer or an infectious disease.

Advantageous Effects of Invention

A fusion protein comprising an IL-2 protein and a CD80 protein can not only activate immune cells owing to IL-2, but also effectively regulate Treg cells owing to CD80. Therefore, the fusion protein can attack cancer cells in an efficient manner, and thus can be usefully employed for treatment of cancer or an infectious disease.

BRIEF DESCRIPTION OF DRAWINGS

FIG. 1 illustrates a schematic embodiment of a fusion protein.

FIG. 2 illustrates a mechanism by which the fusion protein regulates two different types of immune cells; however, it should be understood that the mechanism by which the action of the fusion protein is expressed is not limited thereto.

FIG. 3 illustrates a mechanism by which the fusion protein exhibits an anticancer effect.

FIG. 4 illustrates a schematic view of the structure of the fusion protein. Here, each of GI101 and mGI101 is an embodiment of the fusion protein herein, and GI101C1, GI101C2, and mGI101C1 are comparative examples for comparison with activity of the fusion protein.

FIG. 5 illustrates various embodiments of the fusion protein herein. Human- and mouse-derived proteins may be combined to prepare a fusion protein. CD80 protein and IL-2 protein may be bound to each other via various linkers other than Fc.

FIG. 6 illustrates a result obtained by identifying the obtained fusion protein (GI101) with SDS-PAGE.

FIG. 7 illustrates amounts of the fusion protein (GI101) depending on absorbance.

FIG. 8 illustrates a result obtained by analyzing the obtained fusion protein (GI101) by size exclusion chromatography (SEC).

FIG. 9 illustrates a result obtained by identifying the obtained mGI101 fusion protein with SDS-PAGE.

FIG. 10 illustrates results obtained by identifying the obtained GI101C1 fusion protein with SDS-PAGE.

FIG. 11 illustrates results obtained by identifying the obtained GI101C2 fusion protein with SDS-PAGE.

FIG. 12 illustrates a result obtained by identifying the obtained mGI101C1 fusion protein with SDS-PAGE.

FIG. 13 illustrates results obtained by identifying the obtained GI102-M45 fusion protein with SDS-PAGE.

FIG. 14 illustrates results obtained by identifying the obtained GI102-M61 fusion protein with SDS-PAGE.

FIG. 15 illustrates results obtained by identifying the obtained GI102-M72 fusion protein with SDS-PAGE.

FIG. 16 illustrates binding affinity between hCTLA4 and GI101.

FIG. 17 illustrates binding affinity between hPD-L1 and GI101.

FIG. 18 illustrates binding affinity between hPD-L1 and hPD-1.

FIG. 19 illustrates binding affinity between mCTLA4 and mGI101.

FIG. 20 illustrates binding affinity between mPD-L1 and mGI101.

FIGS. 21 and 22 illustrate results obtained by identifying binding ability between GI-101 (hCD80-Fc-hIL-2v) and CTLA-4, and between GI-101 (hCD80-Fc-hIL-2v) and PD-L1. It was identified that GI-101 (hCD80-Fc-hIL-2v) has high binding ability for CTLA-4 and PD-L1.

FIG. 23 illustrates an effect of GI101 on PD-1/PD-L1 binding. GI101 effectively inhibited PD-1/PD-L1 binding.

FIG. 24 illustrates results obtained by identifying binding affinity between GI101 and IL-2Rα or IL-2Rβ.

FIG. 25 illustrates results obtained by identifying binding affinity between GI101 and IL-2Rα.

FIG. 26 illustrates results obtained by identifying binding affinity between GI101 and IL-2Rβ.

FIG. 27 illustrates results obtained by identifying binding affinity between IL-2Rα and GI102-M45.

FIG. 28 illustrates results obtained by identifying binding affinity between IL-2Rα and GI102-M61.

FIG. 29 illustrates results obtained by identifying binding affinity between IL-2Rα and GI102-M72.

FIG. 30 illustrates results obtained by identifying binding affinity between IL-2Rβ and GI102-M45.

FIG. 31 illustrates results obtained by identifying binding affinity between IL-2Rβ and GI102-M61.

FIG. 32 illustrates results obtained by identifying binding affinity between IL-2Rβ and GI102-M72.

FIGS. 33 and 34 illustrate results obtained by measuring amounts of IFN-γ secreted from cells when the cells are subjected to treatment with GI101, GI101C1, GI101C2, or IL-2 at respective concentrations and incubation is performed.

FIGS. 35 and 36 illustrate results obtained by identifying effects of GI101, GI101C1, GI101C2, and IL-2 (Proleukin) on proliferation of CD8+T cells.

FIG. 37 illustrates results obtained by identifying effects of GI101 and GI102 on proliferation of CD8+T cells and CD4+T cells. Here, FIG. 37A illustrates proportions of CD8+T cells and CD4+T cells, FIG. 37B illustrates proliferation capacity of CD8+T cells, and FIG. 37C illustrates a proportion of CD4+/FoxP3+Treg cells.

FIGS. 38 and 39 illustrate results obtained by identifying effects of GI101 and GI101w on proliferation of CD8+T cells and NK cells.

FIGS. 40 and 41 illustrate results obtained by identifying an effect of GI101 on effector T cells.

FIG. 42 illustrates results obtained by identifying effects of mGI101 and mGI102-M61 on mouse immune cells.

FIGS. 43 and 44 illustrate results obtained by identifying an effect of GI101 on cancer cells overexpressmg PD-L1.

FIGS. 45 and 46 illustrate results obtained by identifying a tumor inhibitory effect of GI101 in mouse-derived colorectal cancer cell-transplanted mice.

FIG. 47 illustrates results obtained by identifying a tumor inhibitory effect of mGI101 in mouse-derived melanoma-transplanted mice.

FIG. 48 illustrates tumor inhibition of mGI101 in mouse-derived melanoma-transplanted mice.

FIG. 49 illustrates results obtained by identifying a tumor inhibitory effect of mGI101, depending on its dose, in mouse-derived colorectal cancer cell-transplanted mice.

FIG. 50 illustrates results obtained by analyzing survival rate of mouse-derived colorectal cancer cell-transplanted mice having received mGI101.

FIG. 51 illustrates results obtained by identifying a tumor inhibitory effect of GI101 in mouse-derived colorectal cancer cell-transplanted mice.

FIG. 52 illustrates results obtained by subjecting mouse-derived colorectal cancer cell-transplanted mice to treatment with hIgG4, anti-PD-1 antibody, or GI101, and then analyzing, with FACS, CD8+T cells, IFN-γ T cells, CD4+T cells, and Treg cells in cancer tissues.

FIG. 53 graphically illustrates results obtained by subjecting mouse-derived colorectal cancer cell-transplanted mice to treatment with hIgG4, anti-PD-1 antibody, or GI101, and then analyzing, with FACS, CD8+T cells, IFN-γ T cells, CD4+T cells, and Treg cells in cancer tissues.

FIG. 54 illustrates results obtained by subjecting mouse-derived colorectal cancer cell-transplanted mice to treatment with hIgG4, anti-PD-1 antibody, or GI101, and then analyzing, with FACS, macrophages in cancer tissues.

FIG. 55 graphically illustrates results obtained by subjecting mouse-derived colorectal cancer cell-transplanted mice to treatment with hIgG4, anti-PD-1 antibody, or GI101, and then analyzing, with FACS, macrophages in cancer tissues.

FIG. 56 illustrates results obtained by subjecting mouse-derived colorectal cancer cell-transplanted mice to treatment with hIgG4, anti-PD-1 antibody, or GI101, and then analyzing, with FACS, dendritic cells in cancer tissues.

FIG. 57 graphically illustrates results obtained by subjecting mouse-derived colorectal cancer cell-transplanted mice to treatment with hIgG4, anti-PD-1 antibody, or GI101, and then analyzing, with FACS, dendritic cells in cancer tissues.

FIG. 58 illustrates results obtained by identifying a tumor inhibitory effect of GI101 in mouse-derived lung cancer cell-transplanted mice.

FIG. 59 graphically illustrates results obtained by subjecting mouse-derived lung cancer cell-transplanted mice to treatment with hIgG4, anti-PD-1 antibody, or GI101, and then analyzing, with FACS, CD8+T cells, IFN-γ T cells, CD4+T cells, and Treg cells in cancer tissues.

FIG. 60 graphically illustrates results obtained by subjecting mouse-derived lung cancer cell-transplanted mice to treatment with hIgG4, anti-PD-1 antibody, or GI101, and then analyzing, with FACS, macrophages in cancer tissues.

FIG. 61 graphically illustrates results obtained by subjecting mouse-derived lung cancer cell-transplanted mice to treatment with hIgG4, anti-PD-1 antibody, or GI101, and then analyzing, with FACS, dendritic cells in cancer tissues.

FIG. 62 illustrates results obtained by identifying a tumor inhibitory effect of mGI102-M61 in mouse-derived colorectal cancer cell-transplanted mice.

FIG. 63 illustrates results obtained by analyzing survival rate of mouse-derived colorectal cancer cell-transplanted mice having received mGI102-M61.

FIG. 64 illustrates results obtained by identifying a tumor inhibitory effect of mGI101 in mouse-derived colorectal cancer cell-transplanted mice.

FIG. 65 illustrates tumor inhibition of mGI101 in mouse-derived colorectal cancer cell-transplanted mice.

FIG. 66 illustrates results obtained by making 15-day clinical observations for monkeys having received PBS or GI101.

FIGS. 67 and 68 illustrate results obtained by measuring body weights on days −1, 1, 8, and 15 for monkeys having received PBS or GI101.

FIG. 69 illustrates 15-day food consumption for monkeys having received PBS or GI101.

FIGS. 70 to 72 illustrate results obtained by analyzing the blood on days −1, 1, 8, and 15 for monkeys having received PBS or GI101.

FIGS. 73 to 79 illustrate results obtained by performing clinical and chemical analysis on days −1, 1, 8, and 15 days for monkeys having received PBS or GI101.

Figure 80:
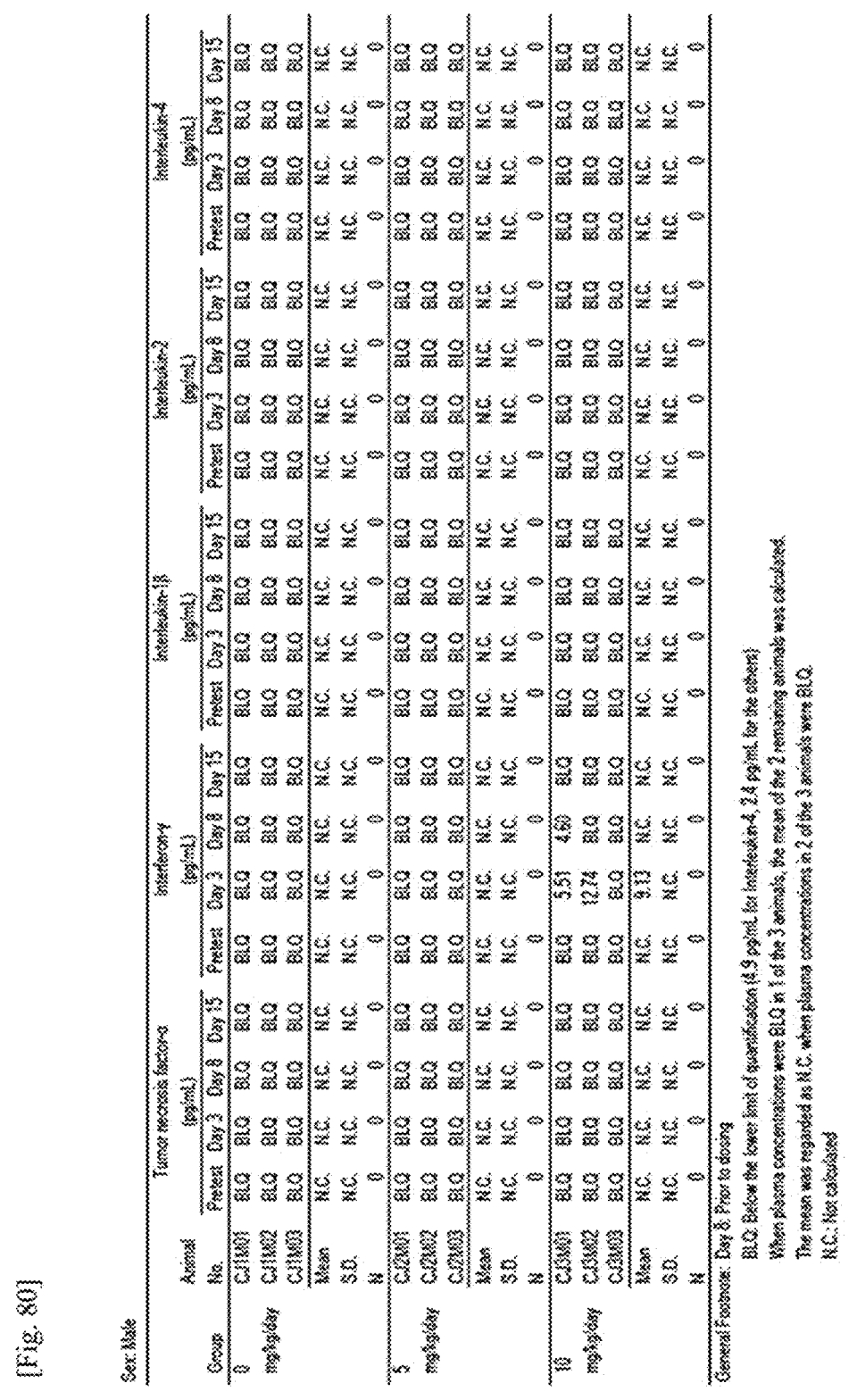

FIGS. 80 and 81 illustrate results obtained by analyzing cytokines on days −1, 1, 8, and 15 for monkeys having received PBS or GI101.

Figure 85:
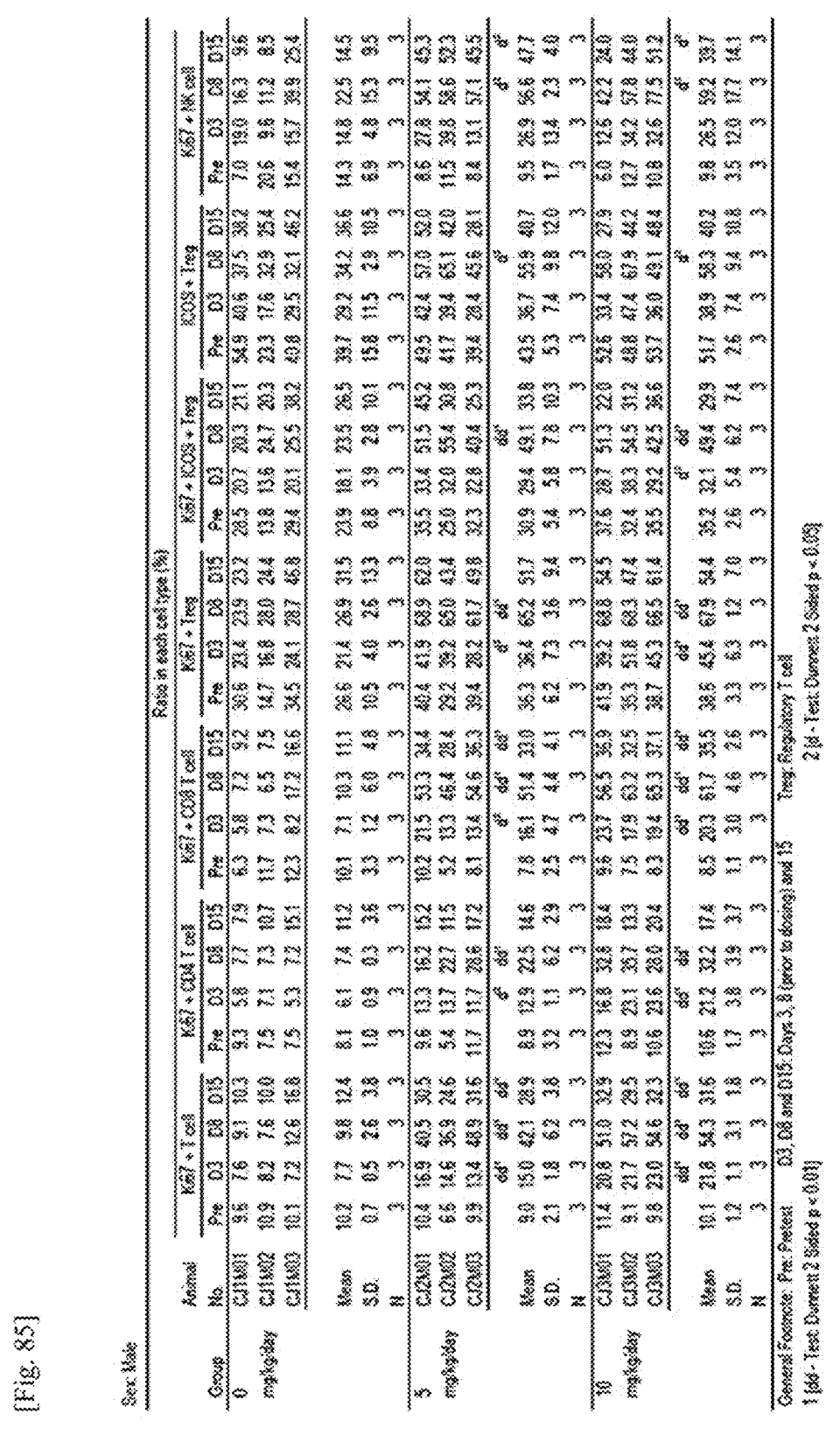
Figure 87:
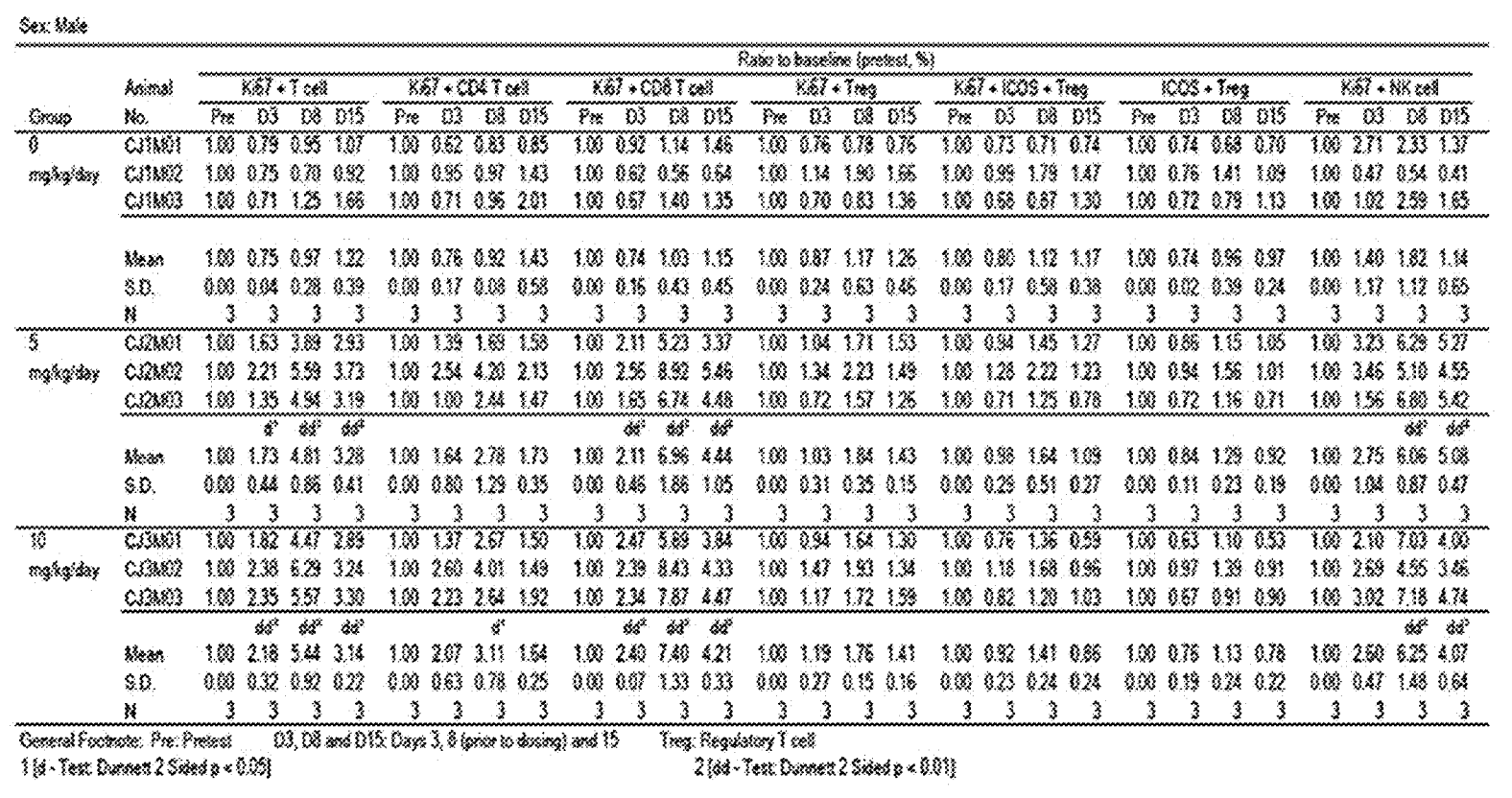

FIGS. 82 to 87 illustrate results obtained by analyzing immune cells on days −1, 1, 8, and 15 for monkeys having received PBS or GI101.

FIG. 88 illustrates results obtained by sacrificing, on day 16, monkeys having received PBS or GI101 to obtain spleen tissues, and pathologically analyzing the spleen tissues.

FIGS. 89A and 89B illustrate fusion proteins, in each of which CD80 protein and IL-2 protein are bound to a carrier protein. Specifically, FIG. 89A illustrates the fusion protein in which the CD80 protein and the IL-2 protein are bound to N-terminus and C-terminus of the carrier protein, respectively. In addition, FIG. 89B illustrates the fusion protein in which the CD80 protein and the IL-2 protein are bound to C-terminus and N-terminus of the carrier protein, respectively. lung cancer cell-transplanted mice to treatment with hIgG4, anti-PD-1 antibody, or GI101, and then analyzing, with FACS, CD8+ T cells, IFN-γ T cells, CD4+ T cells, and Treg cells in cancer tissues.

FIG. 60 graphically illustrates results obtained by subjecting mouse-derived lung cancer cell-transplanted mice to treatment with hIgG4, anti-PD-1 antibody, or GI101, and then analyzing, with FACS, macrophages in cancer tissues.

FIG. 61 graphically illustrates results obtained by subjecting mouse-derived lung cancer cell-transplanted mice to treatment with hIgG4, anti-PD-1 antibody, or GI101, and then analyzing, with FACS, dendritic cells in cancer tissues.

FIG. 62 illustrates results obtained by identifying a tumor inhibitory effect of mGI102-M61 in mouse-derived colorectal cancer cell-transplanted mice.

FIG. 63 illustrates results obtained by analyzing survival rate of mouse-derived colorectal cancer cell-transplanted mice having received mGI102-M61.

FIG. 64 illustrates results obtained by identifying a tumor inhibitory effect of mGI101 in mouse-derived colorectal cancer cell-transplanted mice.

FIG. 65 illustrates tumor inhibition of mGI101 in mouse-derived colorectal cancer cell-transplanted mice.

FIG. 66 illustrates results obtained by making 15-day clinical observations for monkeys having received PBS or GI101.

FIGS. 67 and 68 illustrate results obtained by measuring body weights on days −1, 1, 8, and 15 for monkeys having received PBS or GI101.

FIG. 69 illustrates 15-day food consumption for monkeys having received PBS or GI101.

FIGS. 70 to 72 illustrate results obtained by analyzing the blood on days −1, 1, 8, and 15 for monkeys having received PBS or GI101.

FIGS. 73 to 79 illustrate results obtained by performing clinical and chemical analysis on days −1, 1, 8, and 15 days for monkeys having received PBS or GI101.

FIGS. 80 and 81 illustrate results obtained by analyzing cytokines on days −1, 1, 8, and 15 for monkeys having received PBS or GI101.

FIGS. 82 to 87 illustrate results obtained by analyzing immune cells on days −1, 1, 8, and 15 for monkeys having received PBS or GI101.

FIG. 88 illustrates results obtained by sacrificing, on day 16, monkeys having received PBS or GI101 to obtain spleen tissues, and pathologically analyzing the spleen tissues.

FIG. 89 illustrates fusion proteins, in each of which CD80 protein and IL-2 protein are bound to a carrier protein. Specifically, FIG. 89A illustrates the fusion protein in which the CD80 protein and the IL-2 protein are bound to N-terminus and C-terminus of the carrier protein, respectively. In addition, FIG. 89B illustrates the fusion protein in which the CD80 protein and the IL-2 protein are bound to C-terminus and N-terminus of the carrier protein, respectively.

BEST MODE FOR CARRYING OUT THE INVENTION

Fusion Protein Comprising IL-2 Protein and CD80 Protein

In an aspect of the present invention, there is provided a fusion protein comprising an IL-2 protein and a CD80 protein.

As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{st}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{st}$ amino acids in the amino acid sequence of SEQ ID NO: 10. In addition, in an embodiment, the IL-2 variant may be obtained by substitution of the $45^{th}$ and $72^{nd}$ amino acids in the amino acid sequence of SEQ ID NO: 10. In addition, in an embodiment, the IL-2 variant may be obtained by substitution of the $61^{th}$ and $72^{nd}$ amino acids in the amino acid sequence of SEQ ID NO: 10.

Furthermore, an IL-2 variant may be in a form in which three amino acids are substituted. Specifically, the IL-2 variant may be obtained by substitution of the $38^{th}$ $42^{nd}$, and $45^{th}$ amino acids in the amino acid sequence of SEQ ID NO: 10. In addition, in an embodiment, the IL-2 variant may be obtained by substitution of the $38^{th}$, $42^{nd}$, and $61^{st}$ amino acids in the amino acid sequence of SEQ ID NO: 10. In addition, in an embodiment, the IL-2 variant may be obtained by substitution of the $38^{th}$, $42^{nd}$, and $72^{nd}$ amino acids in the amino acid sequence of SEQ ID NO: 10. In addition, in an embodiment, the IL-2 variant may be obtained by substitution of the $38^{th}$, $45^{th}$, and $61^{st}$ amino acids in the amino acid sequence of SEQ ID NO: 10. In addition, in an embodiment, the IL-2 variant may be obtained by substitution of the $38^{th}$, $45^{th}$, and $72^{nd}$ amino acids in the amino acid sequence of SEQ ID NO: 10. In addition, in an embodiment, the IL-2 variant may be obtained by substitution of the $38^{th}$, $61^{st}$, and $72^{nd}$ amino acids in the amino acid sequence of SEQ ID NO: 10. In addition, in an embodiment, the IL-2 variant may be obtained by substitution of the $42^{nd}$, $45^{th}$, and $61^{st}$ amino acids in the amino acid sequence of SEQ ID NO: 10. In addition, in an embodiment, the IL-2 variant may be obtained by substitution of the $42^{nd}$, $45^{th}$, and $72^{nd}$ amino acids in the amino acid sequence of SEQ ID NO: 10. In addition, in an embodiment, the IL-2 variant may be obtained by substitution of the 45$^{nd}$, 61$^{st}$, and 72$^{nd}$ amino acids in the amino acid sequence of SEQ ID NO: 10.

In addition, an IL-2 variant may be in a form in which four amino acids are substituted. Specifically, the IL-2 variant may be obtained by substitution of the 38$^{th}$ 42$^{nd}$, 45$^{th}$, and 61$^{st}$ amino acids in the amino acid sequence of SEQ ID NO: 10. In addition, in an embodiment, the IL-2 variant may be obtained by substitution of the 38$^{th}$, 42$^{nd}$, 45$^{th}$, and 72$^{nd}$ amino acids in the amino acid sequence of SEQ ID NO: 10. In addition, in an embodiment, the IL-2 variant may be obtained by substitution of the 38$^{th}$, 45$^{th}$, 61$^{st}$, and 72$^{nd}$ amino acids in the amino acid sequence of SEQ ID NO: 10. In addition, in an embodiment, the IL-2 variant may be obtained by substitution of the 38$^{th}$, 42$^{nd}$, 61$^{st}$, and 72$^{nd}$ amino acids in the amino acid sequence of SEQ ID NO: 10. In addition, in an embodiment, the IL-2 variant may be obtained by substitution of 42$^{nd}$, 45$^{th}$, 61$^{st}$, and 72$^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the 38$^{th}$, 42$^{nd}$, 45$^{th}$, 61$^{st}$, and 72$^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the 38$^{th}$ amino acid cannot be substituted with arginine, the 42$^{nd}$ amino acid cannot be substituted with phenylalanine, the 45$^{th}$ amino acid cannot be substituted with tyrosine, the 61$^{st}$ amino acid cannot be substituted with glutamic acid, and the 72$^{nd}$ amino acid cannot be substituted with leucine.

Regarding amino acid substitution for an IL-2 variant, in the amino acid sequence of SEQ ID NO: 10, the 38$^{th}$ amino acid, arginine, may be substituted with an amino acid other than arginine. Preferably, regarding amino acid substitution for an IL-2 variant, in the amino acid sequence of SEQ ID NO: 10, the 38$^{th}$ amino acid, arginine, may be substituted with alanine (R38A).

Regarding amino acid substitution for an IL-2 variant, in the amino acid sequence of SEQ ID NO: 10, the 42$^{nd}$ amino acid, phenylalanine, may be substituted with an amino acid other than phenylalanine. Preferably, regarding amino acid substitution for an IL-2 variant, in the amino acid sequence of SEQ ID NO: 10, the 42$^{nd}$ amino acid, phenylalanine, may be substituted with alanine (F42A).

Regarding amino acid substitution for an IL-2 variant, in the amino acid sequence of SEQ ID NO: 10, the 45$^{th}$ amino acid, tyrosine, may be substituted with an amino acid other than tyrosine. Preferably, regarding amino acid substitution for an IL-2 variant, in the amino acid sequence of SEQ ID NO: 10, the 45$^{th}$ amino acid, tyrosine, may be substituted with alanine (Y45A).

Regarding amino acid substitution for an IL-2 variant, in the amino acid sequence of SEQ ID NO: 10, the 61$^{st}$ amino acid, glutamic acid, may be substituted with an amino acid other than glutamic acid. Preferably, regarding amino acid substitution for an IL-2 variant, in the amino acid sequence of SEQ ID NO: 10, the 61$^{st}$ amino acid, glutamic acid, may be substituted with arginine (E61R).

Regarding amino acid substitution for an IL-2 variant, in the amino acid sequence of SEQ ID NO: 10, the 72$^{nd}$ amino acid, leucine, may be substituted with an amino acid other than leucine. Preferably, regarding amino acid substitution for an IL-2 variant, in the amino acid sequence of SEQ ID NO: 10, the 72$^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:

(a) R38A/F42A
(b) R38A/F42A/Y45A
(c) R38A/F42A/E61R
(d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Rα). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides costimulatory signals essential for activation and survival of T cells. CD80 is known as a ligand for the two different proteins, CD28 and CTLA-4, present on the surface of T cells. CD80 is composed of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a cleaved form of CD80. In addition, the CD80 fragment may be an extracellular domain of CD80. An embodiment of the CD80 fragment may be obtained by elimination of the 1$^{st}$ to 34$^{th}$ amino acids from N-terminus which are a signal sequence of CD80. Specifically, an embodiment of the CD80 fragment may be a protein composed of the 35$^{th}$ to 288$^{th}$ amino acids in SEQ ID NO: 11. In addition, an embodiment of the CD80 fragment may be a protein composed of the 35$^{th}$ to 242$^{nd}$ amino acids in SEQ ID NO: 11. In addition, an embodiment of the CD80 fragment may be a protein composed of the 35$^{th}$ to 232$^{nd}$ amino acids in SEQ ID NO: 11. In addition, an embodiment of the CD80 fragment may be a protein composed of the 35$^{th}$ to 139$^{th}$ amino acids in SEQ ID NO: 11. In addition, an embodiment of the CD80 fragment may be a protein composed of the 142$^{nd}$ to 242$^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type F domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fe domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids.

An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively (FIGS. 89A and 89B). Linkage between N-terminus or C-terminus of the Fc domain and CD-80 or IL-2 may optionally be achieved by a linker peptide.

Specifically, a fusion protein may consist of the following structural formula (I) or (II):

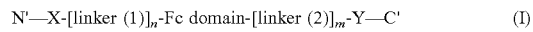

N'—X-[linker (1)]$_n$-Fc domain-[linker (2)]$_m$-Y—C'　　(I)

N'—Y-[linker (1)]$_n$-Fc domain-[linker (2)]$_m$-X—C'　　(II)

Here, in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80.

Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be $(G4S)_n$ (where n is an integer of 1 to 10). Here, in (G4S), n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

Polynucleotide Encoding Fusion Protein

In yet another aspect of the present invention, there is provided a polynucleotide encoding a fusion protein comprising an IL-2 protein and a CD80 protein. Specifically, the polynucleotide may contain the nucleotide sequence of SEQ ID NO: 8, 25, 27, or 29. The fusion protein comprising an IL-2 protein and a CD80 protein is as described above. In the polynucleotide, one or more nucleotides may be altered by substitution, deletion, insertion, or a combination thereof. When a nucleotide sequence is prepared by chemical synthesis, synthetic methods well known in the art may be used, such as those described in Engels and Uhlmann (Angew Chem IntEd Eng., 37: 73-127, 1988). Such methods may include triester, phosphite, phosphoramidite and H-phosphate methods, PCR and other autoprimer methods, oligonucleotide syntheses on solid supports, and the like.

According to an embodiment, the polypeptide may contain a nucleic acid sequence having an identity, to SEQ ID NO: 8, 25, 27, or 29, of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100%.

The polynucleotide may further contain a nucleic acid encoding a signal sequence or a leader sequence. As used herein, the term "signal sequence" refers to a signal peptide that directs secretion of a target protein. The signal peptide is translated and then cleaved in a host cell. Specifically, the signal sequence is an amino acid sequence that initiates migration of a protein across the endoplasmic reticulum (ER) membrane. In an embodiment, the signal sequence may have the amino acid sequence of SEQ ID NO: 1.

Signal sequences are well known in the art for their characteristics. Such signal sequences typically contain 16 to 30 amino acid residues, and may contain more or fewer amino acid residues than such amino acid residues. A typical signal peptide is composed of three regions, that is, a basic N-terminal region, a central hydrophobic region, and a more polar C-terminal region. The central hydrophobic region contains 4 to 12 hydrophobic residues that cause the signal sequence to be immobilized during migration of an immature polypeptide through the membrane lipid bilayer.

After initiation, signal sequences are cleaved in the lumen of ER by cellular enzymes, commonly known as signal peptidases. Here, the signal sequence may be a secretory signal sequence of tPa (tissue plasminogen activator), HSV gDs (signal sequence of Herpes simplex virus glycoprotein D), or a growth hormone. Preferably, a secretory signal sequence used in higher eukaryotic cells including mammals and the like may be used. In addition, a signal sequence included in the wild-type IL-2 and/or CD-80 may be used, or a signal sequence that has been substituted with a codon having high expression frequency in a host cell may be used.

Vector with Polynucleotide Encoding Fusion Protein

In still yet another aspect of the present invention, there is provided a vector comprising the polynucleotide.

The vector may be introduced into a host cell to be recombined with and inserted into the genome of the host cell. Or, the vector is understood as nucleic acid means containing a polynucleotide sequence which is autonomously replicable as an episome. The vectors include linear nucleic acids, plasmids, phagemids, cosmids, RNA vectors, viral vectors, and analogs thereof. Examples of the viral vector include, but are not limited to, retroviruses, adenoviruses, and adeno-associated viruses.

Specifically, the vector may include plasmid DNA, phage DNA, and the like; and commercially developed plasmids (pUC18, pBAD, pIDTSAMRT-AMP, and the like), E. coli-derived plasmids (pYG601BR322, pBR325, pUC118, pUC119, and the like), Bacillus subtilis-derived plasmids (pUB110, pTP5, and the like), yeast-derived plasmids (YEp13, YEp24, YCp50, and the like), phage DNA (Charon4A, Charon21A, EMBL3, EMBL4, λ gt10, λ gt11, λ ZAP, and the like), animal viral vectors (retroviruses, adenoviruses, vaccinia viruses, and the like), insect viral vectors (baculoviruses and the like). Since the vector exhibits different expression levels and modification of a protein depending on a host cell, it is preferred to select and use a host cell which is most suitable for the purpose.

As used herein, the term "gene expression" or "expression" of a target protein is understood to mean transcription of DNA sequences, translation of mRNA transcripts, and secretion of fusion protein products or fragments thereof. A useful expression vector may be RcCMV (Invitrogen, Carlsbad) or a variant thereof. Expression vectors may further contain human cytomegalovirus (CMV) promoter for promoting continuous transcription of a target gene in mammalian cells, and a bovine growth hormone polyadenylation signal sequence for increasing the stability level of RNA after transcription.

Transformed Cell Expressing Fusion Protein

In still yet another aspect of the present invention, there is provided a transformed cell into which the vector has been introduced.

Host cells for the transformed cell may include, but are not limited to, prokaryotic cells, eukaryotic cells, and cells of mammalian, vegetable, insect, fungal, or bacterial origin.

As an example of the prokaryotic cells, E. coli may be used. In addition, as an example of the eukaryotic cells, yeast may be used. In addition, for the mammalian cells, CHO cells, F2N cells, CSO cells, BHK cells, Bowes melanoma cells, HeLa cells, 911 cells, AT1080 cells, A549 cells, HEK 293 cells, HEK293T cells, or the like may be used. However, the mammalian cells are not limited thereto, and any cells which are known to those skilled in the art to be usable as mammalian host cells may be used.

In addition, for the introduction of an expression vector into the host cell, $CaCl_2$) precipitation, Hanahan method whose efficiency has been increased efficiency by using a reducing agent such as dimethyl sulfoxide (DMSO) in $CaCl_2$ precipitation, electroporation, calcium phosphate precipitation, protoplast fusion, agitation using silicon carbide fiber, Agrobacteria-mediated transformation, transformation using PEG, dextran sulfate-, Lipofectamine-, or dry/inhibition-mediated transformation, or the like may be used.

As described above, for optimization of properties of a fusion protein as a therapeutic agent or for any other purpose, glycosylation pattern of the fusion protein (for example, sialic acids, fucosylations, glycosylations) may be adjusted by manipulating, through methods known to those skilled in the art, glycosylation-related genes possessed by host cells.

Method for Producing a Fusion Protein

In still yet another aspect of the present invention, there is provided a method for producing a fusion protein comprising an IL-2 protein and a CD80 protein, the method comprising culturing the transformed cells. Specifically, the production method may comprise i) culturing the transformed cells to obtain a culture; and ii) collecting the fusion protein from the culture.

Culturing the transformed cells may be carried out using methods well known in the art. Specifically, the culture may be carried out in a batch process, or carried out continuously in a fed batch or repeated fed batch process.

Use of Fusion Protein or Dimer Thereof

In still yet another aspect of the present invention, there is provided a pharmaceutical composition for treating or preventing cancer or an infectious disease, and/or for increasing efficacy in treating cancer or an infectious disease, the composition comprising, as an active ingredient, a fusion protein comprising an IL-2 protein and a CD80 protein or a fusion protein dimer where the two fusion proteins are attached.

The fusion protein comprising an IL-2 protein and a CD80 protein, or the fusion protein dimer where the two fusion proteins are attached is as described above.

The cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain tumor, neuroblastoma, retinoblastoma, head and neck cancer, salivary gland cancer, and lymphoma. In addition, the infectious disease may be any one selected from the group consisting of hepatitis B, hepatitis C, human papilloma virus (HPV) infection, cytomegalovirus infection, viral respiratory disease, and influenza.

A preferred dose of the pharmaceutical composition varies depending on the patient's condition and body weight, severity of disease, form of drug, route and duration of administration and may be appropriately selected by those skilled in the art. In the pharmaceutical composition for treating or preventing cancer or an infectious disease of the present invention, the active ingredient may be contained in any amount (effective amount) depending on application, dosage form, blending purpose, and the like, as long as the active ingredient can exhibit anticancer activity or a therapeutic effect on an infectious disease. A conventional effective amount thereof will be determined within a range of 0.001% to 20.0% by weight, based on the total weight of the composition. Here, the term "effective amount" refers to an amount of an active ingredient capable of inducing an anticancer effect or an infectious disease-treating effect. Such an effective amount can be experimentally determined within the scope of common knowledge of those skilled in the art.

As used herein, the term "treatment" may be used to mean both therapeutic and prophylactic treatment. Here, prophylaxis may be used to mean that a pathological condition or disease of an individual is alleviated or mitigated. In an embodiment, the term "treatment" includes both application or any form of administration for treating a disease in a mammal, including a human. In addition, the term includes inhibiting or slowing down a disease or disease progression; and includes meanings of restoring or repairing impaired or lost function so that a disease is partially or completely alleviated; stimulating inefficient processes; or alleviating a serious disease.

As used herein, the term "efficacy" refers to capacity that can be determined by one or parameters, for example, survival or disease-free survival over a certain period of time such as one year, five years, or ten years. In addition, the parameter may include inhibition of size of at least one tumor in an individual.

Pharmacokinetic parameters such as bioavailability and underlying parameters such as clearance rate may also affect efficacy. Thus, "enhanced efficacy" (for example, improvement in efficacy) may be due to enhanced pharmacokinetic parameters and improved efficacy, which may be measured by comparing clearance rate and tumor growth in test animals or human subjects, or by comparing parameters such as survival, recurrence, or disease-free survival.

As used herein, the term "therapeutically effective amount" or "pharmaceutically effective amount" refers to an amount of a compound or composition effective to prevent or treat the disease in question, which is sufficient to treat the disease at a reasonable benefit/risk ratio applicable to medical treatment and does not cause adverse effects. A level of the effective amount may be determined depending on factors including the patient's health condition, type and severity of disease, activity of drug, the patient's sensitivity to drug, mode of administration, time of administration, route of administration and excretion rate, duration of treatment, formulation or simultaneously used drugs, and other factors well known in the medical field. In an embodiment, the therapeutically effective amount means an amount of drug effective to treat cancer.

Here, the pharmaceutical composition may further comprise a pharmaceutically acceptable carrier. The pharmaceutically acceptable carrier may be any carrier as long as the carrier is a non-toxic substance suitable for delivery to a patient. Distilled water, alcohol, fat, wax, and inert solid may be contained as the carrier. A pharmaceutically acceptable adjuvant (buffer, dispersant) may also be contained in the pharmaceutical composition.

Specifically, by including a pharmaceutically acceptable carrier in addition to the active ingredient, the pharmaceutical composition may be prepared into a parenteral formulation depending on its route of administration using conventional methods known in the art. Here, the term "pharmaceutically acceptable" means that the carrier does not have more toxicity than the subject to be applied (prescribed) can adapt while not inhibiting activity of the active ingredient.

When the pharmaceutical composition is prepared into a parenteral formulation, it may be made into preparations in the form of injections, transdermal patches, nasal inhalants, or suppositories with suitable carriers according to methods known in the art. In a case of being made into injections, sterile water, ethanol, polyol such as glycerol or propylene glycol, or a mixture thereof may be used as a suitable carrier; and an isotonic solution, such as Ringer's solution, phosphate buffered saline (PBS) containing triethanol amine or sterile water for injection, and 5% dextrose, or the like may preferably be used. Formulation of pharmaceutical compositions is known in the art, and reference may specifically be made to Remington's Pharmaceutical Sciences (19th ed., 1995) and the like. This document is considered part of the present description.

A preferred dose of the pharmaceutical composition may range from 0.01 μg/kg to 10 g/kg, or 0.01 mg/kg to 1 g/kg, per day, depending on the patient's condition, body weight, sex, age, severity of the patient, and route of administration. The dose may be administered once a day or may be divided into several times a day. Such a dose should not be construed as limiting the scope of the present invention in any aspect.

Subjects to which the pharmaceutical composition can be applied (prescribed) are mammals and humans, with humans being particularly preferred. In addition to the active ingredient, the pharmaceutical composition of the present application may further contain any compound or natural extract, which has already been validated for safety and is known to have anticancer activity or a therapeutic effect on an infectious disease, so as to boost or reinforce anticancer activity.

In still yet another aspect of the present invention, there is provided a use of a fusion protein comprising an IL-2 protein and a CD80 protein for treating cancer or an infectious disease.

In still yet another aspect of the present invention, there is provided a use of a fusion protein comprising an IL-2 protein and a CD80 protein for enhancing a therapeutic effect on cancer or an infectious disease.

In still yet another aspect of the present invention, there is provided a use of a fusion protein comprising an IL-2 protein and a CD80 protein for manufacture of a medicament for treating cancer or an infectious disease.

In still yet another aspect of the present invention, there is provided a method for treating cancer or an infectious disease, and/or a method for enhancing a therapeutic effect on cancer or an infectious disease, comprising administering, to a subject, a fusion protein comprising an IL-2 protein and a CD80 protein or a fusion protein dimer where the two fusion proteins are attached.

The subject may be an individual suffering from cancer or an infectious disease. In addition, the subject may be a mammal, preferably a human. The fusion protein comprising an IL-2 protein and a CD80 protein, or the fusion protein dimer where the two fusion proteins are attached is as described above.

Route of administration, dose, and frequency of administration of the fusion protein or fusion protein dimer may vary depending on the patient's condition and the presence or absence of side effects, and thus the fusion protein or fusion protein dimer may be administered to a subject in various ways and amounts. The optimal administration method, dose, and frequency of administration can be selected in an appropriate range by those skilled in the art. In addition, the fusion protein or fusion protein dimer may be administered in combination with other drugs or physiologically active substances whose therapeutic effect is known with respect to a disease to be treated, or may be formulated in the form of combination preparations with other drugs.

Due to IL-2 activity, the fusion protein in an embodiment of the present invention can activate immune cells such as natural killer cells. Thus, the fusion protein can be effectively used for cancer and infectious diseases. In particular, it was identified that as compared with the wild type, an IL-2 variant with two to five amino acid substitutions, in particular, an IL-2 variant that contains amino acid substitutions at two, three, four, or five positions among the positions selected from the group consisting of R38A, F42A, Y45A, E61R, and L72G, has low binding ability for the IL-2 receptor alpha chain and thus exhibits improved characteristics with respect to pharmacological side effects of conventional IL-2. Thus, such an IL-2 variant, when used alone or in the form of a fusion protein, can decrease incidence of vascular (or capillary) leakage syndrome (VLS), a problem with IL-2 conventionally known.

MODE FOR THE INVENTION

Hereinafter, the present invention will be described in more detail by way of the following examples. However, the following examples are only for illustrating the present invention, and the scope of the present invention is not limited thereto.

I. Preparation of Fusion Protein

Preparation Example 1. Preparation of hCD80-Fc-IL-2 Variant (2M): GI101

In order to produce a fusion protein comprising a human CD80 fragment, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 8) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) having two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 9. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101".

Purification was carried out using chromatography containing MabSelect SuRe protein A resin. The fusion protein was bound thereto under a condition of 25 mM Tris, 25 mM NaCl, pH 7.4. Then, elution was performed with 100 mM NaCl, 100 mM acetic acid, pH 3. 20% 1 M Tris-HCl at pH 9 was placed in a collection tube, and then the fusion protein was collected. For the collected fusion protein, the buffer was exchanged through dialysis with PBS buffer for 16 hours.

Thereafter, absorbance at 280 nm wavelength was measured, over time, with size exclusion chromatography using a TSKgel G3000SWXL column (TOSOH Bioscience), to obtain a highly concentrated fusion protein. Here, the isolated and purified fusion protein was subjected to SDS-PAGE under reduced (R) or non-reduced (NR) condition, and stained with Coomassie Blue to check its purity (FIG. 6). It was identified that the fusion protein was contained at a concentration of 2.78 mg/ml when detected with Nano-Drop (FIG. 7). In addition, the results obtained by analysis using size exclusion chromatography are provided in FIG. 8.

Preparation Example 2. Preparation of mCD80-Fc-IL-2 Variant (2M): mGI101

In order to produce a fusion protein comprising a mouse CD80, an Fe domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 14) which encodes a fusion protein that contains a signal peptide (SEQ ID NO: 1), a mCD80 (SEQ ID NO: 13), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 15. After the vector was introduced, culture was performed for 7 days in an environment of 37° C., 125 RPM, and 8% $CO_2$ concentration. Then, the culture was harvested and the fusion protein was purified therefrom. The purified fusion protein was designated "mGI101".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 9). It was found that the fusion protein was contained at a concentration of 1.95 mg/ml when detected by absorbance at 280 nm using NanoDrop.

Preparation Example 3. Preparation of hCD80-Fc: GI101C1

In order to produce a fusion protein comprising a human CD80 fragment and an Fc domain, a polynucleotide was synthesized through the Invitrogen GeneArt Gene Synthesis service of ThermoFisher Scientific. Specifically, the polynucleotide contains a nucleotide sequence (SEQ ID NO: 16) which encodes a fusion protein that contains a signal peptide (SEQ ID NO: 1), a CD80 fragment (SEQ ID NO: 2), an Ig hinge (SEQ ID NO: 3), and an Fc domain (SEQ ID NO: 4). The polynucleotide was inserted into pcDNA3_4 vector. In addition, the vector was introduced into CHO cells (Expi-CHO™) to express the fusion protein of SEQ ID NO: 17. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 10). It was observed that the fusion protein was contained at a concentration of 3.61 mg/ml when detected by absorbance at 280 nm using NanoDrop.

Preparation Example 4. Preparation of Fc-IL-2 Variant (2M): GI101C2

In order to produce a fusion protein comprising an Fc domain and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 18) which encodes a fusion protein that contains a signal peptide (SEQ ID NO: 1), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 19. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101C2".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 11). It was found that the fusion protein was contained at a concentration of 4.79 mg/ml when detected by absorbance at 280 nm using NanoDrop.

Preparation Example 5. Preparation of mCD80-Fc: mGI101C1

In order to produce a fusion protein comprising a mouse CD80 and an Fe domain, a polynucleotide was synthesized through the Invitrogen GeneArt Gene Synthesis service of ThermoFisher Scientific. Specifically, the polynucleotide contains a nucleotide sequence (SEQ ID NO: 20) which encodes a fusion protein that contains a signal peptide (SEQ ID NO: 1), a mCD80 (SEQ ID NO: 13), an Ig hinge (SEQ ID NO: 3), and an Fc domain (SEQ ID NO: 4), in this order, from the N-terminus. The polynucleotide was inserted into pcDNA3_4 vector. In addition, the vector was introduced into CHO cells (Expi-CHO™) to express the fusion protein of SEQ ID NO: 21. After the vector was introduced, culture was performed for 7 days in an environment of 37° C., 125 RPM, and 8% $CO_2$ concentration. Then, the culture was harvested and the fusion protein was purified therefrom. The purified fusion protein was designated "mGI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 12). It was observed that the fusion protein was contained at a concentration of 2.49 mg/ml when detected by absorbance at 280 nm using NanoDrop.

The fusion proteins prepared in Preparation Examples 1 to 5 are summarized in Table 1 below.

TABLE 1

| Item | N-terminus | Linker | C-terminus |
|---|---|---|---|
| Preparation Example 1 (GI101) | hCD80 fragment | Fc domain | hIL-2m |

TABLE 1-continued

| Item | N-terminus | Linker | C-terminus |
|---|---|---|---|
| Preparation Example 2 (mGI101) | mCD80 fragment | Fc domain | hIL-2m |
| Preparation Example 3 (GI101C1) | CD80 fragment | Fc domain | — |
| Preparation Example 4 (GI101C2) | — | Fc domain | IL-2m |
| Preparation Example 5 (mGI101C1) | mCD80 fragment | Fc domain | — |

Preparation Example 6. Preparation of CD80-Fc-IL-2: GI101w

In order to produce a fusion protein comprising a human CD80 fragment, an Fc domain, and a human IL-2, a polynucleotide was synthesized through the Invitrogen GeneArt Gene Synthesis service of ThermoFisher Scientific. Specifically, the polynucleotide contains a nucleotide sequence (SEQ ID NO: 31) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and mature human IL-2 (SEQ ID NO: 10), in this order, from the N-terminus. The polynucleotide was inserted into pcDNA3_4 vector. In addition, the vector was introduced into CHO cells (Expi-CHO™) to express the fusion protein of SEQ ID NO: 32. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101w". The purification and collection of the fusion protein were carried out in the same manner as in Preparation Example 1.

Preparation Example 7. Preparation of hCD80-Fc-IL-2 Variant (3M): GI102-M45

In order to produce a fusion protein comprising a human CD80 fragment, an Fc domain, and an IL-2 variant (3M) (R38A, F42A, Y45A) (GI102-M45) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 25) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 22), in this order, from the N-terminus. The polynucleotide was inserted into pcDNA3_4 vector. In addition, the vector was introduced into CHO cells (Expi-CHO™) to express the fusion protein of SEQ ID NO: 26. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M45".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 13).

Preparation Example 8. Preparation of hCD80-Fc-IL-2 Variant (3M): GI102-M61

In order to produce a fusion protein comprising a human CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 27) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 28. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M61".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 14).

Preparation Example 9. Preparation of hCD80-Fc-IL-3M: GI102-M72

In order to produce a fusion protein comprising a human CD80 fragment, an Fc domain, and an IL-2 variant (3M) (R38A, F42A, L72G) (GI102-M72) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 29) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 24), in this order, from the N-terminus. The polynucleotide was inserted into pcDNA3_4 vector. In addition, the vector was introduced into CHO cells (Expi-CHO™) to express the fusion protein of SEQ ID NO: 30. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M72".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 15).

Preparation Example 10. Preparation of mCD80-Fc-IL-3M: mGI102-M61

In order to produce a fusion protein comprising a mouse CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 33) which encodes a fusion protein that contains a signal peptide (SEQ ID NO: 1), a mCD80 fragment (SEQ ID NO: 13), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 34. After the vector was introduced, culture was performed for 7 days in an environment of 37° C., 125 RPM, and 8% $CO_2$ concentration. Then, the culture was harvested and the fusion protein was purified therefrom. The purified fusion protein was designated "mGI102-M61".

The purification and collection of the fusion protein were carried out in the same manner as in Preparation Example 1.

II. Identification of Binding Affinity Between Fusion Protein and its Ligand

In order to identify the binding affinity between the fusion protein and its ligand, the binding affinity was measured using Octet RED 384.

Experimental Example 1. Identification of Binding Affinity Between hCTLA-4 and GI101

AR2G biosensor (Amine Reactive $2^{nd}$ gen, ForteBio, Cat: 18-5092) was previously hydrated with 200 µl of distilled water in a 96-well microplate (GreinerBio-one, Cat: 655209). A ligand (CTLA-4, Human CTLA-4/CD152, His tag, Sino Biological, Cat: 11159-H08H) to be attached to the AR2G biosensor was diluted with 10 mM acetate buffer (pH 5, AR2G reagent Kit, ForteBio, Cat: 18-5095) to a concentration of 5 g/ml. In addition, GI101 to be attached to the ligand was diluted with 1×AR2G kinetic buffer (AR2G reagent Kit, ForteBio, Cat: 18-5095) to a concentration of 1,000 nM, 500 nM, 250 nM, 125 nM, or 62.5 nM. Activation buffer was prepared by mixing 20 mM EDC and 10 mM s-NHS (AR2G reagent Kit, ForteBio, Cat: 18-5095) in distilled water. 80 µl of each reagent was placed in a 384-well microplate (Greiner Bio-one, Cat: 781209) and the program was set up.

As a result, the binding affinity between hCTLA-4 and GI101 was measured as illustrated in FIG. 16.

Experimental Example 2. Identification of Binding Affinity Between hPD-L1/GI101 and hPD-L1/PD-1

Ni-NTA (Nickel charged Tris-NTA, Ni-NTA Biosensors, ForteBio, 18-5101) was previously hydrated with 200 of 1×Ni-NTA kinetic buffer (10× Kinetics buffer, ForteBio, 18-1042) in a 96-well microplate (GreinerBio-one, Cat: 655209). A ligand (Human PD-L1/B7-H1 protein, His-tag, Sino biological, Cat: 10084-H08H) to be attached to the Ni-NTA Biosensors was diluted with 1×Ni-NTA kinetic buffer to a concentration of 5 g/ml. GI101 to be attached to the ligand was diluted with 1×Ni-NTA kinetic buffer at 1,000 nM, 500 nM, 250 nM, 125 nM, or 62.5 nM. In addition, human PD-1/PDCD1 (Human PD-1/PDCD1, Fc Tag, Sino Biological, Cat: 10377-H02H) to be attached to the ligand was diluted with 1×Ni-NTA kinetic buffer to a concentration of 2,000 nM, 1,000 nM, 500 nM, 250 nM, or 125 nM. Then, 80 µl of each reagent was placed in a 384-well microplate and the program was set up.

As a result, the binding affinity between hPD-L1 and GI101 was measured as illustrated in FIG. 17. In addition, the binding affinity between hPD-L1 and hPD-1 was measured as illustrated in FIG. 18.

Experimental Example 3. Identification of Binding Affinity Between mCTLA-4 and mGI101

The binding affinity between mCTLA-4 and mGI101 was examined in the same manner as in Experimental Example 1. Here, the equipment used is as follows: Biosensor: AR2G, Ligand: mCTLA-4 (Recombinant Mouse CTLA-4 Fc chimera, R&D Systems, Cat: 434-CT-200), Analyte: mGI101 (500 nM, 250 nM, 125 nM, 62.5 nM, 31.3 nM).

As a result, the binding affinity between mCTLA-4 and mGI101 was measured as illustrated in FIG. 19.

Experimental Example 4. Identification of Binding Affinity Between mPD-L1 and mGI101

The binding affinity between mPD-L1 and mGI101 was identified in the same manner as in Experimental Example 1. Here, the equipment used is as follows. Biosensor: AR2G, Ligand: mPD-L1 (Recombinant Mouse B7-H1/PD-L1 Fc chimera, R&D Systems, Cat: 434-CT-200), Analyte: mGI101 (500 nM, 250 nM, 125 nM, 62.5 nM, 31.3 nM).

As a result, the binding affinity between mPD-L1 and mGI101 was measured as illustrated in FIG. 20.

Experimental Example 5. Identification of Binding Ability of GI-101 (hCD80-Fc-hIL-2v) to CTLA-4 and PD-L1

Binding kinetics measurements were performed using the Octet RED 384 instrument (ForteBio, Pall Life Science) with agitation at 30° C. and 1,000 rpm. The binding ability for CTLA-4 was measured using the Amine Reactive 2 generation (AR2G) biosensor chip, and the binding ability for PD-L1 was measured using the Nickel charged Tris-NTA (Ni-NTA) biosensor chip. The AR2G biosensor chip was activated with a combination of 400 mM EDC and 100 mM sulfo-NHS. Then, Human CTLA-4-His Tag (Sino Biological, Cat: 11159-H08H) was diluted with 10 mM acetate buffer (pH 5) to 5 g/ml, and loaded on the AR2G biosensor chip for 300 seconds and fixed.

Then, binding of CTLA-4 to GI-101 (hCD80-Fc-hIL-2v), GI-101C1 (hCD80-Fc), Ipilimumab (Bristol-Myers Squibb), and GI-101C2 (Fc-hIL-2v) at various concentrations was measured for 300 seconds and dissociation thereof was also measured for 300 seconds. On the other hand, Human PD-L1-His Tag (Sino biological, Cat: 10084-H08H) was diluted with 1×Ni-NTA kinetic buffer to a concentration of 5 µg/ml, and loaded on the Ni-NTA biosensor chip for 600 seconds and fixed. Then, binding of PD-L1 to GI-101, GI-101C1, hPD-1-Fc (Sino biological, Cat: 10377-H02H), and GI101C2 at various concentrations was measured for 300 seconds and dissociation thereof was also measured for 300 seconds. Binding kinetics analysis was performed using Octet Data Analysis HT software ver. 10 provided by Pall Corporation. The results are illustrated in FIGS. 21 and 22.

Experimental Example 6. Identification of Effect of GI-101 (hCD80-Fc-hIL-2v) on PD-1/PD-L1 Binding A blocking experiment was performed using the Octet RED 384 instrument (ForteBio, Pall Life Science) with agitation at 30° C. and 1,000 rpm. Human PD-L1-His Tag (Sino biological, Cat: 10084-H08H) was diluted with 1×Ni- NTA kinetic buffer to a concentration of 5 μg/ml, and loaded on the Ni-NTA biosensor chip for 600 seconds and fixed. In order to proceed with the blocking experiment, hPD-L1 fixed on the biosensor chip was allowed to bind to GI-101 at various concentrations (300 nM, 100 nM, 50 nM, 25 nM, 12.5 nM, and 0 nM) for 600 seconds, and then again allowed to bind to the competitor human PD-1 (100 nM) for 600 seconds so as to measure how much more hPD-1 can bind thereto. On the contrary, hPD-L1 was allowed to bind to hPD-1 at various concentrations (300 nM, 100 nM, 50 nM, 25 nM, 12.5 nM, and 0 nM) for 600 seconds, and then again allowed to bind to the competitor GI-101 (100 nM) for 600 seconds so as to measure how much more GI-101 can bind thereto. The blocking experiment was analyzed using the epitope binning menu of Octet Data Analysis HT software ver. 10 provided by Pall Corporation. The results are illustrated in FIG. 23.

Experimental Example 7. Identification of Binding Affinity Between IL-2Rα or IL-2Rβ and GI101

The binding ability for IL-2Rα was measured using the AR2G biosensor, and the binding ability for IL-2Rβ was measured using the Ni-NTA biosensors (Nickel charged Tris-NTA, Ni-NTA Biosensors, ForteBio, 18-5101).

A ligand (IL-2Rα-His Tag, Acro, Cat: ILA-H52H9) to be attached to the AR2G biosensor was diluted with 10 mM acetate buffer (pH 5, AR2G reagent Kit, ForteBio, Cat: 18-5095) to a concentration of 5 g/ml. The AR2G biosensor was activated with a buffer prepared by mixing 400 mM EDC and 100 mM sulfo-NHS, and then the diluted ligand was loaded on the AR2G biosensor for 300 seconds and fixed.

Meanwhile, a ligand (IL-2Rβ-His Tag, Acro, Cat: CD2-H5221) to be attached to the Ni-NTA biosensor was diluted with 1×Ni-NTA kinetic buffer to a concentration of 5 g/ml. The diluted ligand was loaded on the Ni-NTA biosensor for 600 seconds and fixed.

Thereafter, GI101, GI101w, or Proleukin (Novartis, hIL-2), at various concentrations, to be attached to the ligand was loaded thereon for 300 seconds. Then, binding thereof was measured and dissociation thereof was also measured for 300 seconds. Binding kinetics analysis was performed using Octet Data Analysis HT software ver. 10 provided by Pall Corporation. The results are illustrated in FIGS. 24 to 26.

As a result, it was identified that GI101 has low binding ability for the IL-2 receptor alpha chain, IL-2Rα, and high binding ability for IL-2Rβ, as compared with GI101w and Proleukin.

Experimental Example 8. Measurement of Binding Affinity Between Fusion Protein and Ligand In order to identify binding affinity between the fusion protein and its ligand, binding affinity was measured using Octet RED 384.

Experimental Example 8.1. Identification of Binding Affinity Between IL2 Alpha Receptor and GI101-M45, GI101-M61, or GI101-M72

AR2G biosensor (Amine Reactive 2nd gen, ForteBio, Cat: 18-5092) was previously hydrated with 200 of distilled water (DW) in a 96-well microplate (GreinerBio-one, Cat: 655209). A ligand (Human IL-2 R alpha protein, His Tag, Acro, ILA-H52H9) to be attached to the biosensor was diluted with 10 mM acetate buffer (pH 5) (AR2G reagent Kit, ForteBio, Cat: 18-5095) to a concentration of 5 g/ml. An analyte (GI101-M45, GI101-M61, GI101-M72) to be attached to the ligand was diluted with 1×AR2G kinetic buffer (AR2G reagent Kit, ForteBio, Cat: 18-5095) to 500 nM, 250 nM, 125 nM, and 62.5 nM, respectively. Activation buffer was prepared by mixing 20 mM EDC and 10 mM s-NHS (AR2G reagent Kit, ForteBio, Cat: 18-5095) in DW. 80 μl of each reagent was placed in a 384-well microplate (Greiner Bio-one, Cat: 781209) and the program was set up.

As a result, the binding affinity between IL2 alpha receptor and GI101-M45 is illustrated in FIG. 27. In addition, the binding affinity between IL2 alpha receptor and GI101-M61 is illustrated in FIG. 28, and the binding affinity between IL2 alpha receptor and GI101-M72 is illustrated in FIG. 29.

Experimental Example 8.2. Identification of Binding Affinity of GI102-M45, GI102-M61, and GI102-M72 to IL-2Rβ

Ni-NTA Biosensors were previously hydrated with 200 of 1×Ni-NTA kinetic buffer (10× Kinetics buffer, ForteBio, 18-1042) in a 96-well microplate. A ligand (Human IL-2 R beta protein, His-Tag, Acro, CD2-H5221) to be attached to the biosensor was diluted with 1×Ni-NTA kinetic buffer to a concentration of 2 g/ml. GI102-M45, GI102-M61, or GI102-M72 to be attached to the ligand was diluted with 1×Ni-NTA kinetic buffer to a concentration of 500 nM, 250 nM, 125 nM, or 62.5 nM. 80 of each reagent was placed in a 384-well microplate and the program was set up.

As a result, the binding affinity between IL-2R and GI02-M45 was measured as illustrated in FIG. 30, and the binding affinity between IL-2Rβ and GI102-M61 was measured as illustrated in FIG. 31. In addition, the binding affinity between IL-2Rβ and GI102-M72 was measured as illustrated in FIG. 32.

III. Identification of Immune Activity of Fusion Protein

Experimental Example 9. Identification of IFN-γ Production Caused by Fusion Protein Experimental Example 9.1. Culture of CFSE-Labeled PBMCs Peripheral blood mononuclear cells (PBMCs) isolated from a human were labeled with carboxyfluorescein succinimidyl ester (CFSE) by being reacted with 1 μM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well plate at 1×10⁵ cells per well. Treatment with 5 μg/ml of PHA (Lactin from Phaseolus Vulgaris, red kidney bean, Sigma-Aldrich, St. Louis, Mo., USA, Cat. No. L1668-5MG), and GI101, GI101C1, GI101C2, or IL-2 (Aldesleukin; human recombinant IL-2, Novartis) was performed and incubation was performed in a 5% $CO_2$ incubator at 37° C. for 6 days.

Here, the treatment with GI101, GI101C1, GI101C2, and IL-2 was performed at a concentration of 1 nM, 10 nM, or 100 nM. The cells were analyzed by FACS, and human IFN-γ present in the culture medium was measured using an ELISA kit (Biolegend, San Diego, Calif., USA, Cat. No. 430103).

Experimental Example 9.2. FACS Analysis

The cell pellets obtained by removing the supernatant were washed with FACS buffer (3% FBS, 10 mM EDTA, 1M HEPES, 100 unit/mL Penicillin Streptomycin, 10 g/ml, 1 mM sodium pyruvate), and then reacted with Fc blocker (Biolegend, Cat. No. 422302) at 4° C. for 5 minutes. Then, treatment with APC anti-CD3 Ab (Biolegend, Cat. No. 300412) and PE anti-CD8a Ab (Biolegend, Cat. No. 300908) was performed and reaction was allowed to proceed at 4° C. for 20 minutes. Then, the resultant was washed with FACS buffer. The cell pellets were resuspended in FACS buffer and then analyzed using BD LSR Fortessa (BD Biosciences, San Diego, Calif., USA) and FlowJo software.

Experimental Example 9.3. Human IFN-γ ELISA

The amount of human IFN-γ secreted into the supernatant of each sample in which the cells had been cultured was measured using a human IFN-γ ELISA kit (Biolegend, Cat. No. 430103). Briefly, anti-human-IFN-γ antibodies were added to an ELISA plate, and reaction was allowed to proceed overnight at 4° C. so that these antibodies were coated thereon. Then, blocking was performed at room temperature for 1 hour with a PBS solution to which 1% BSA had been added. Washing with a washing buffer (0.05% Tween-20 in PBS) was performed, and then a standard solution and each sample were properly diluted and added thereto. Then, reaction was allowed to proceed at room temperature for 2 hours.

After the reaction was completed, the plate was washed and secondary antibodies (detection antibodies) were added thereto. Reaction was allowed to proceed at room temperature for 1 hour. Washing with a washing buffer was performed, and then an Avidin-HRP solution was added thereto. Reaction was allowed to proceed at room temperature for 30 minutes. A substrate solution was added thereto and color development reaction was induced in the dark at room temperature for 20 minutes. Finally, $H_2SO_4$ was added thereto to stop the color development reaction, and the absorbance at 450 nm was measured with Epoch Microplate Spectrophotometer (BioTek Instruments, Inc., Winooski, Vt., USA).

As a result, it was found that cells treated with GI101 exhibited a remarkable increase in IFN-γ secretion, as compared with cells treated with GI101C1, GI101C2, or IL-2 (FIGS. 33 and 34).

Experimental Example 10. Identification of Effect of GI101 on Proliferation of CD8+ T Cells Peripheral blood mononuclear cells (PBMCs) isolated from a human were labeled with CFSE by being reacted with 1 μM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercapto-ethanol, 1 mM non-essential amino acid, and 2 mM L-glutamine), and then added to a 96-well plate at $1\times10^5$ cells per well.

Thereafter, treatment with 1 g/ml of anti-CD3a antibody (Biolegend Cat. No. L1668-5MG), and GI101, GI101C1, GI101C2, or Proleukin (Novartis) was performed and incubation was performed in a 5% $CO_2$ incubator at 37° C. for 6 days. Here, the cells were treated with GI101, GI101C, GI101C2, and IL-2 at a concentration of 100 nM. The incubated cells were examined for their degree of proliferation by measuring, with FACS analysis using APC-TCRαβ and PE-CD8α antibodies, a proportion of CD8+ T cells that had not been labeled with CFSE.

As a result, it was found that GI101 activated proliferation of CD8+ T cells in vitro to a similar extent to the wild-type IL-2 Proleukin (FIGS. 35 and 36).

Experimental Example 11. Identification of Effect of GI101 and GI102 on Proliferation of CD8+ T Cells Human PBMCs were purchased from Allcells (Lot #3014928, USA). 1M CellTrace CFSE dye was used, which was reacted with the human PBMCs under a light-blocking condition at room temperature for 20 minutes. The cells were labeled with CFSE by being reacted with 1 μM CellTrace CFSE dye at 37° C. for 20 minutes. CFSE not bound to the cells was removed by being reacted for 5 minutes with culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercapto-ethanol, 1 mM non-essential amino acid, and 2 mM L-glutamine), and then added to a 96-well plate at $1\times10^5$ cells per well.

Thereafter, the CFB-labeled PBMCs were subjected to treatment with 1 g/ml of anti-CD3β antibody (OKT3, eBioscience, USA), and GI101, GI101C, GI101C2, or Proleukin (Novartis), and incubation was performed in a 5% $CO_2$ incubator at 37° C. for 7 days. Here, the cells were subjected to treatment with GI101, GI101C, GI101C2, and IL-2 at a concentration of 10 μM.

The incubated cells were examined for their degree of proliferation by measuring, with FACS analysis using anti-human CD4-PE antibody (BioLegend, USA), anti-human CD8-PE/Cy7 antibody (BioLegend, USA), and anti-human FoxP3-APC antibody (BioLegend, USA), a proportion of CD8+ T cells that had not been labeled with CFSE.

As a result, the GI101, GI102_M61, GI101C2, and Proleukin treatment groups exhibited a significant increase in proportion of CD8+ T cells, as compared with the control group (no stimulus), the anti-CD3 antibody alone treatment group, and the GI101C1 treatment group. In addition, as compared with the negative control group (no stimulus) and the anti-CD3 alone treatment group, the GI101, GI101C2, and Proleukin treatment groups exhibited a significant increase in proliferation of CD4+/FoxP3+ Treg cells, whereas the GI102 and GI101C1 treatment groups did not exhibit a significant increase in proliferation of CD4+/FoxP3+ Treg cells (FIG. 37).

Experimental Example 12. Identification of Effect of GI101 or GI101w on Proliferation of CD8+ T Cells and NK Cells 7-week-old C57BL/6 mice purchased from Orient Bio (Busan, Korea) were divided into 3 groups, each group containing 3 mice, and PBS, GI101, or GI101w was injected intraperitoneally thereinto. Here, GI101 and GI101w were respectively prepared to be at 40.5 g in 200 µl of PBS, and injected intraperitoneally thereinto. Five days after the injection, the spleens were removed from the mice of each group. The cells were isolated therefrom, and the total number of cells was measured using a hematocytometer. Splenocytes were examined for proportions of CD8+ T cells and NK cells therein, with FACS analysis using staining with APC-CD3ε antibody (Biolegend; 145-2C11), PE-NK1.1 antibody (Biolegend; PK136), and Pacific blue-CD8α antibody (BD; 53-6.7). As such, the numbers of CD8+ T cells and NK cells present in the spleen were calculated.

As a result, it was identified that GI101 activated proliferation of CD8+ T cells and NK cells in vivo as compared with GI101w (FIGS. 38 and 39).

Experimental Example 13. Identification of Effect of GI101 on Function of T Cells An experiment was performed using a CTLA-4 blockade bioassay kit (Promega Cat. No. JA4005). The experiment is briefly described as follows. CTLA-4 effector cells kept in liquid nitrogen were thawed in a 37° C. constant temperature water bath for 3 minutes, and 0.8 ml of CTLA-4 effector cells were mixed well with 3.2 ml of pre-warmed assay buffer (90% RPMI+10% FBS). Then, the mixture was added to a 96-well white cell culture plate (SPL, Cat. No. 30196) at 25 per well. Then, 25 µl of GI101 at various concentrations was added thereto. For a negative control, 25 µl of assay buffer was added thereto. Then, the white plat cell culture plate was covered and placed at room temperature until aAPC/Raji cells were prepared.

aAPC/Raji cells kept in liquid nitrogen were thawed in a 37° C. constant temperature water bath for 3 minutes, and 0.8 ml of aAPC/Raji cells were mixed well with 3.2 ml of pre-warmed assay buffer. Then, 25 µl of the mixture was added to the plate at per well, and reaction was allowed to proceed in a 5% $CO_2$ incubator at 37° C. for 16 hours. After the reaction was completed, the resultant was allowed to stand at room temperature for 15 minutes, and then the Bio-Glo reagent was added thereto while taking care to avoid bubbles. The Bio-Glo reagent was also added to three of the outermost wells and the wells were used as blanks to correct the background signal. Reaction was allowed to proceed at room temperature for 10 minutes, and then luminescence was measured with Cytation 3 (BioTek Instruments, Inc., Winooski, Vt., USA). Final data analysis was performed by calculating RLU (GI101-background)/RLU (notreatment-background).

As a result, it was found that GI101 attached to CTLA-4 expressed on effector T cells, and activated the function of T cells rather than inhibiting the same (FIGS. 40 and 41).

Experimental Example 14. Identification of Effect of mGI101 and mGI102 on Immune Cells 7-week-old C57BL/6 mice purchased from Orient Bio (Korea) were divided into 3 groups, each group containing 3 mice, and PBS, 3 mg/kg, 6 mg/kg, or 12 mg/kg of GI101, or 3 mg/kg, 6 mg/kg, or 12 mg/kg of mGI102 (mGI102-M61) was administered intravenously thereinto. On days 1, 3, 5, 7, and 14 after the injection, the spleens were removed from the mice of each group. Thereafter, for the spleen tissue, the numbers of effector CD8+ T cells, NK cells, and Treg cells were calculated with FACS analysis using respective antibodies, and proportions of effector CD8+ T cells and NK cells with respect to Treg cells were respectively calculated. The information on the antibodies used in each cell assay is as follows:

Effector CD8+ T cells: PB anti-mouse CD3a antibody (Biolegend, #155612; KT3.1.1), FITC anti-mouse CD8α antibody (BD, #553031, 53-6.7), PE/Cy7 anti-mouse CD44 antibody (Biolegend, #103030; IM7), APC anti-mouse CD122 antibody (Biolegend, #123214; TM-β1)

NK cells: PB anti-mouse CD3a antibody (Biolegend, #155612; KT3.1.1), PE anti-mouse NK-1.1 (Biolegend, #108708; PK136)

Treg cells: FITC anti-mouse CD3 antibody (Biolegend, #100204; 17A2), PB anti-mouse CD4 antibody (Biolegend, #100531; RM4-5), PE anti-mouse CD25 antibody (Biolegend, #102008; PC61), APC anti-mouse Foxp3 antibody (Invitrogen, #FJK-16s, 17-5773-82).

As a result, the group having received mGI101 or mGI102 (mGI102-M61) exhibited a significant increase in numbers of CD8+ T cells and NK cells at the time points from 3 days to 14 days after administration, as compared with the PBS administration group. In addition, it was found that the group having received mGI102 exhibited a significant increase in proportions of activated CD8+ T cells/Treg cells and NK cells/Treg cells at the time points from 3 days to 14 days after administration, as compared with the PBS administration group (FIG. 42).

IV. Identification of Anticancer Effect of Fusion Protein

Experimental Example 15. Identification of Effect of GI101 on Cancer Cells Overexpressing PD-L1

NCl-H292 cancer cell line overexpressing PD-L1 was cultured for 3 hours in a culture medium containing 10 µg/ml Mitomycin C (Sigma), and then Mitomycin C was removed by washing with the culture medium. Thereafter, $5 \times 10^4$ cells of the Mitomycin C-treated NCl-H292 cancer cell line were incubated with $1 \times 10^5$ cells of human PBMCs in a 96-well plate. Here, treatment with 5 g/ml of PHA (Sigma) was performed for T cell activity. In addition, GI101C1 and GI101 at a concentration of 50 nM were reacted with IgG1-Fc (Biolegend) or abatacept (=Orencia; Bristol-Myers Squibb) at a concentration of 50 nM for 30 minutes at 4° C., and then the resultant was used to treat the NCl-H292 cancer cells. After 3 days, the supernatant of the cell incubate was collected and the amount of IFN-γ was quantified using an ELISA kit (Biolegend).

As a positive control group, human PBMCs stimulated with PHA in the absence of the Mitomycin C-treated NCl-H292 cancer cell line were used; and as a negative control group, human PBMCs stimulated with PHA in the presence of the Mitomycin C-treated NCl-H292 cancer cell line was used. An experimental method using the IFN-γ ELISA kit was carried out in the same manner as in Experimental Example 9.3.

As a result, GI101 effectively activated the immune response that had been inhibited by the cancer cell line overexpressing PD-L1. In addition, it was discovered that GI101 inhibited signaling of CTLA-4 expressed on effector T cells (FIGS. 43 and 44).

Experimental Example 16. Identification of Anticancer Effect of GI101 in Mouse-Derived Colorectal Cancer Cell-Transplanted Mice $5 \times 10^6$ cells/0.05 ml of mouse-derived CT-26 cancer cell line was mixed with 0.05 ml Matrigel matrix phenol red-free (BD), and transplantation of 0.1 ml of the mixture was performed by subcutaneous administration in the right dorsal region of 6-week-old female BALB/c mice (Orient Bio). A certain period of time after the cancer cell transplantation, the tumor volume was measured and subjects that reached about 80 mm³ to 120 mm³ were separated. Then, the subjects were intravenously administered with 0.1 ml of GI101. A total of three administrations were given once every three days after the first administration, and PBS was given to a negative control group. The tumor size was measured daily to identify an anticancer effect.

As a result, it was observed that the CT-26 cancer cell line-transplanted mice treated with GI101 exhibited a remarkable decrease in tumor size as compared with the negative control group (FIGS. 45 and 46).

Experimental Example 17. Identification of Anticancer Effect of mGI101 in Mouse-Derived Melanoma-Transplanted Mice C57BL/6 mice (female, 7-week-old) acquired from Orient Bio were subjected to an acclimation period of 7 days. Then, 5×10⁶ cells of B16F10 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 50 mm³ to 120 mm³ were selected, and then the selected mice were grouped evenly based on tumor size and body weight, each group containing 10 mice.

Thereafter, using a disposable syringe (31G, 1 mL), hIgG4 was administered at a dose of 4 mg/kg to a negative control group, and an anti-PD-1 antibody was administered at a dose of 5 mg/kg to a positive control group. For experimental groups, mGI101 at a dose of 1 mg/kg or 4 mg/kg was administered intravenously thereto. Additionally, groups having received mGI101 at a dose of 4 mg/kg and an anti-PD-1 antibody at a dose of 5 mg/kg were also set as experimental groups. A total of three administrations were given once every three days after the first administration. The tumor size was measured daily.

As a result, the initial tumor volume of all groups was 90 mm³, and standard error (S.E.) of each group was 5 mm³ to 6 mm³. In the negative control group, a change in tumor volume was observed during the experimental period, in which the tumor volume increased from 90 mm³ to 1,434 mm³ up to 15 days after the administration.

In the group having received mGI101 at a dose of 1 mg/kg, the tumor volume was observed to increase from 90 mm³ to 885 mm³ during the experimental period which is the same period as the negative control group, and a statistically significant inhibition of tumor growth was observed at some measurement time points (p-value: 0.5 on day 11, p-value <0.01 on day 7, p-value <0.001 on day 3). In the group having received mGI101 at a dose of 4 mg/kg, the tumor volume was observed to increase from 90 mm³ to 748 mm³ during the experimental period which is the same period as the negative control group, and a statistically significant inhibition of tumor growth was observed at some measurement time points (p-value: 0.5 on day 9, p-value <0.01 on days 7 and 11).

In addition, tumor growth inhibition rate was analyzed by using, as a reference, the group having received mIgG at a dose of 4 mg/kg and comparing this group with each of the other groups. In the group having received mGI101 at a dose of 1 mg/kg, growth inhibition rate of 36.5% was observed as compared with the negative control group, and no statistically significant difference (p-value: 0.5) was observed. In the group having received mGI101 at a dose of 4 mg/kg, a statistically significant (p-value: 0.5) tumor growth inhibition rate was observed as compared with the negative control group. A total of two administrations were given once every three days after the first administration. The tumor size was measured daily.

Through this, it was found that in tumor growth inhibitory efficacy test for B16F10, a melanoma allotransplanted into C57BL/6 mice, mGI101 had an effect of inhibiting tumor growth in a dose-dependent manner (FIGS. 47 and 48).

Experimental Example 18. Identification of Anticancer Effect of mGI101 in Mouse-Derived Colorectal Cancer Cell-Transplanted Mice BALB/c mice (female, 7-week-old) acquired from Orient Bio were subjected to an acclimation period of 7 days. Then, 5×10⁶ cells of CT-26 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 mm³ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI101 at a dose of 3 mg/kg, 6 mg/kg, or 12 mg/kg was administered intravenously thereto. A total of three administrations were given once every three days after the first administration. The tumor size was measured daily.

As a result, it was found that the experimental group having received mGI101 at a dose of 6 mg/kg or 12 mg/kg mGI101 exhibited significant inhibition of tumor growth at some measurement time points and at the end of the test, as compared with the negative control group (FIG. 49). In addition, as a result of measuring a survival rate, it was found that the experimental group having received mGI101 at a dose of 6 mg/kg exhibited significant improvement at some measurement time points and at the end of the test, as compared with the negative control group (FIG. 50).

Experimental Example 19. Identification of Anticancer Effect of GI101 in Mice Transplanted with Mouse-Derived Colorectal Cancer Cells Experimental Example 19.1. Identification of Tumor Inhibitory Effect BALB/c mice (female, 7-week-old) acquired from Orient Bio were subjected to an acclimation period of 7 days. Then, 5×10⁶ cells of CT-26 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm³ to 200 mm³ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, in the CT-26 cancer cell line-transplanted mice, all groups having received anti-PD-1 antibody, anti-PD-1 antibody and anti-CTLA-4 antibody, or GI101 at a dose of 0.1 mg/kg or 1 mg/kg exhibited significant inhibition of tumor growth, as compared with the negative control. In particular, the experimental group having received GI101 at a dose of 0.1 mg/kg exhibited a significant tumor inhibitory effect, as compared with the anti-PD-1 antibody treatment group (*p<0.05) (FIG. 51).

Experimental Example 19.2. Immune Cell Analysis in Cancer Tissue

The mice of each group in Experimental Example 19.1 were sacrificed when the tumor volume reached an average of 200 mm$^3$, and cancer tissues were collected. Thereafter, the cancer tissues were separated to a single-cell level to analyze immune cells therein, and then FACS analysis was performed on immune cells in the cancer tissues using the following antibodies: Anti-mouse-CD3 (Biolegend, Cat. No. 100320), Anti-mouse-CD4 (Biolegend, Cat. No. 100526), Anti-mouse-CD8 (Biolegend, Cat. No. 100750), Anti-mouse-FoxP3 (eBioscience, Cat. No. 12-5773-82), Anti-mouse-CD25 (Biolegend, Cat. No. 102049), Anti-mouse-CD44 (eBioscience, Cat. No. 61-0441-82), Anti-mouse-PD-1 (Biolegend, Cat. No. 135218), Anti-mouse-IFN-gamma (Biolegend, Cat. No. 505832), Anti-mouse-CD49b (Biolegend, Cat. No. 108906), Anti-mouse-H2 (Invitrogen, Cat. No. A15443), Anti-mouse-CD11c (Biolegend, Cat. No. 117343), Anti-mouse-CD80 (eBioscience, Cat. No. 47-4801-82), Anti-mouse-CD86 (Biolegend, Cat. No. 104729), Anti-mouse-F4/80 (eBioscience, Cat. No. 47-4801-82), and Anti-mouse-CD206 (eBioscience, Cat. No. 17-2061-80).

As a result, the experimental group having received GI101 at a dose of 0.1 mg/kg exhibited a significant increase in CD8+ T cells, as compared with the positive control group having received anti-PD-1 antibody alone at a dose of 5 mg/kg (*p<0.05, FIGS. 52 and 53). Furthermore, all experimental groups having received GI101 exhibited a significantly increased level of expression of IFN-γ in T cells, as compared with the negative control group (*p<0.05, FIGS. 52 and 53). In addition, the experimental group having received GI101 at a dose of 0.1 mg/kg exhibited an increase in M1 macrophages as compared with the negative control group and the positive control group having received anti-PD-1 antibody alone (FIGS. 54 and 55). In addition, all experimental groups having received GI101 exhibited an increased level of CD86 expression in macrophages and dendritic cells (*p<0.05, FIGS. 54 to 57).

Experimental Example 20. Identification of Anticancer Effect of GI101 in Mice Transplanted with Mouse-Derived Lung Cancer Cells
Experimental Example 20.1. Identification of Tumor Inhibitory Effect C57BL/6 mice (female, 7-week-old) acquired from Orient Bio were subjected to an acclimation period of 7 days. Then, 5×10$^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, all experimental groups exhibited a significant tumor inhibitory effect, as compared with the negative control group (*p<0.05) (FIG. 58).

Experimental Example 20.2. Immune Cell Analysis in Cancer Tissue

The mice of each group in Experimental Example 20.1 were sacrificed when the tumor volume reached an average of 200 mm, and cancer tissues were collected. Thereafter, FACS analysis was performed in the same manner as Experimental Example 19.2 to analyze immune cells in the cancer tissues.

As a result, the experimental group having received GI101 at a dose of 0.1 mg/kg exhibited a significant increase in CD8+ T cells, as compared with the positive control group having received anti-PD-1 antibody alone (*p<0.05, FIG. 59). Furthermore, all experimental groups having received GI101 exhibited a significantly increased level of expression of IFN-γ, as compared with the negative control group (*p<0.05, FIG. 59). In addition, all experimental groups having received GI101 exhibited an increased level of CD86 expression in macrophages and dendritic cells (*p<0.05, FIGS. 59 to 61).

Experimental Example 21. Identification of Anticancer Effect of mGI102-M61 in Mice Transplanted with Mouse-Derived Colorectal Cancer Cells BALB/c mice (female, 7-week-old) acquired from Orient Bio were subjected to an acclimation period of 7 days. Then, 5×10$^6$ cells of CT-26 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 mm$^3$ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI102-M61 at a dose of 3 mg/kg, 6 mg/kg, or 12 mg/kg was administered intravenously thereto. A total of three administrations were given once every three days after the first administration. The tumor size was measured daily.

As a result, it was identified that the experimental group having received mGI102-M61 at a dose of 12 mg/kg exhibited significant inhibition of tumor growth at some measurement time points and at the end of the test, as compared with the negative control group (FIG. 62). In addition, as a result of measuring a survival rate, it was identified that the experimental group having received mGI102-M61 at a dose of 12 mg/kg exhibited significant improvement at some measurement time points and at the end of the test, as compared with the negative control group (FIG. 63).

Experimental Example 22. Identification of Anticancer Effect of mGI101 in Mice Transplanted with Mouse-Derived Colorectal Cancer Cells BALB/c mice (female, 7-week-old) acquired from Orient Bio were subjected to an acclimation period of 7 days. Then, $5 \times 10^6$ cells of CT-26 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 200 $mm^3$ to 250 $mm^3$ were selected, and then the selected mice were grouped evenly based on tumor size and body weight, each group containing 10 mice.

Thereafter, using a disposable syringe (31G, 1 mL), hIgG4 was administered at a dose of 4 mg/kg to a negative control group. For experimental groups, mGI101 at a dose of 1 mg/kg, 4 mg/kg, or 6 mg/kg was administered intravenously thereto. Additionally, groups having received mCD80 at 4.9 mg/kg or Fc-IL-2v (GI101C2) at 2.8 mg/kg were set as control groups. In addition, a group having simultaneously received mCD80 at 4.9 mg/kg and Fc-IL-2v (GI101C2) at 2.8 mg/kg was set as a control group.

In tumor volume measurement, it was identified that the group having received mGI101 at a dose of 6 mg/kg exhibited significant inhibition at some measurement time points and at the end of the test, as compared with the negative control. An excellent tumor growth inhibition rate was observed as compared with the group having received a combination of mCD80 and Fc-IL-2v (GI101C2) (FIGS. 64 and 65).

In conclusion, in the tumor growth-inhibitory efficacy test on BALB/c mice allotransplanted with CT-26, a BALB/c mouse-derived colorectal cancer cell line, it was demonstrated that the test substance mGI101 had tumor inhibitory efficacy under this test condition as compared with mCD80 and IL-2v single preparations; and it was identified that mGI101 exhibited excellent anticancer efficacy as compared with the group having received a combination of mCD80 and IL-2v (FIGS. 64 and 65). In particular, the group having received mGI101 at a dose of 6 mg/kg exhibited significant inhibition of tumor size, as compared with the negative control group and the group having received a combination of mCD80 and Fc-IL2v (GI101C2).

V. Toxicity Evaluation of Fusion Protein

Experimental Example 23. Toxicity Evaluation of GI101 Using Monkeys

Experimental Example 23.1. Monkey Breeding and Drug Administration

In the present experiment, nine male Philippine monkeys (Cynomolgus monkeys) aged 2 to 3 years were used. The experiment was carried out in accordance with the "Act on Welfare and Management of Animals" in Japan and the "Guidance for Animal Care and Use" of Ina Research Inc. The experimental protocol was reviewed by the Institutional Animal Care and Use Committee (IACUC) of Ina Research Inc, and then approved by AAALAC International (Accredited Unit No. 001107).

The experiment was conducted from one day before drug administration up to 15 days after drug administration. Each monkey was observed around the cage, and the stool status was additionally checked. Body weights were measured using a digital scale (LDS-150H, Shimadzu Corporation) one day before drug administration, and on days 1, 8, and 15 after drug administration. In addition, the remaining amount of food was measured from one day before drug administration up to sacrifice of the monkeys.

Here, a disposable syringe (24G) was filled with the drug GI101, and a total of two administrations were given via an intravenous route, each administration being made at a rate of 0.17 ml/sec. GI101 was given twice, at a week's interval, at a dose of 5 mg/kg/day or 10 mg/kg/day. A control group was administered PBS (pH 7.4) in the same manner.

Experimental Example 23.2. Clinical Observation, Identification of Changes in Body Weight and Food Intake Clinical observation, and measurement of changes in body weight and food intake were performed from one day before drug administration up to days 1, 8, and 15 after drug administration. As a result, no toxicity was caused by GI101 (FIGS. 66 to 69).

Experimental Example 23.3. Blood Analysis

Blood was collected from the monkeys in Experimental Example 23.1 one day before drug administration, and on days 1, 8, and 15 after drug administration. Here, the blood was collected via the femoral vein with a disposable syringe (22G). The collected blood was subjected to blood analysis using the Automated Hematology System XN-2000 (Sysmex Corporation) and the Automated Blood Coagulation Analyzer CA-510 (Sysmex Corporation) for the items listed in Table 2 below

TABLE 2

| Parameter | Abbr. | Unit | Method | Equipment |
|---|---|---|---|---|
| Complete blood count | | | | |
| Red blood cell count | RBC | $10^6/\mu L$ | DC sheath-flow detection | XN-2000 |
| Hemoglobin concentration | HGB | g/dL | SLS-hemoglobin | XN-2000 |
| Hematocrit | HCT | % | RBC pulse height detection | XN-2000 |
| Mean corpuscular volume | MCV | fL | HCT/RBC ($\times 10^4$/ $\mu L$) $\times$ 1000 | XN-2000 |
| Mean corpuscular hemoglobin | MCH | pg | HGB/RBC ($\times 10^4$/ $\mu L$) $\times$ 1000 | XN-2000 |
| Mean corpuscular hemoglobin concentration | MCHC | g/dL | HGB/HCT $\times$ 100 | XN-2000 |
| Reticulocytes Ratio Count | RET % RET # | % $10^9/L$ | Flow cytometry | XN-2000 |
| Platelet count | PLT | $10^3/\mu L$ | Flow cytometry | XN-2000 |
| White blood cell count | WBC | $10^3/\mu L$ | Flow cytometry | XN-2000 |
| Differential white blood cells [a]Ratio Count | Diff WBC % Diff WBC # | % $10^3/\mu L$ | Flow cytometry | XN-2000 |
| Coagulation tests | | | | |
| Prothrombin time | PT | s | Light scattering detection | CA-510 |
| Activated partial thromboplastin time | APTT | s | Light scattering detection | CA-510 |

[a]Neutrophils (NEUT), lymphocytes (LYMPH), monocytes (MONO), eosinophils (EO) and basophils (BASO)

As a result, the group having received GI at a dose of 5 mg/kg/day or 10 mg/kg/day exhibited an increase in numbers of reticulocytes, leukocytes, and lymphocytes on day 15 (FIGS. 70 to 72).

Experimental Example 23.4. Clinical and Chemical Analysis

Blood was collected from the monkeys in Experimental Example 23.1 one day before drug administration, and on days 1, 8, and 15 after drug administration. Here, the blood was collected in the same manner as in Experimental Example 23.3. The collected blood was subjected to clinical and chemical analysis using the Clinical Analyzer Model 7180 (Hitachi High-Technologies Corporation) for the items listed in Table 3 below.

TABLE 3

| Parameter | Abbr. | Unit | Method |
|---|---|---|---|
| Aspartate aminotransferase | AST | U/L | JSCC traceable method |
| Alanine aminotransferase | ALT | U/L | JSCC traceable method |
| Alkaline phosphatase | ALP | U/L | JSCC traceable method |
| Lactate dehydrogenase | LD | U/L | JSCC traceable method |
| Creatine kinase | CK | U/L | JSCC traceable method |
| Glucose | GLU | mg/dL | Enzymatic (Gluc-DH) |
| Total bilirubin | BIL | mg/dL | Enzymatic (BOD) |
| Urea nitrogen | UN | mg/dL | Enzymatic (urease-LEDH) |
| Creatinine | CRE | mg/dL | Enzymatic |
| Total cholesterol | CHO | mg/dL | Enzymatic (cholesterol oxidase) |
| Triglycerides | TG | mg/dL | Enzymatic (GK-GPO with free glycerol elimination) |
| Phospholipids | PL | mg/dL | Enzymatic (choline oxidase) |
| Inorganic phosphorus | IP | mg/dL | Enzymatic (maltose phosphorylase) |
| Calcium | CA | mg/dL | OCPC |
| Sodium | NA | mEq/L | Ion-selective electrode |
| Potassium | K | mEq/L | Ion-selective electrode |
| Chloride | CL | mEq/L | Ion-selective electrode |
| Total protein | TP | g/dL | Biuret |
| Albumin | ALB | g/dL | BCG |
| Albumin-globulin ratio | A/G | — | Calculated |

JSCC: Japan Society of Clinical Chemistry

As a result, no toxicity caused by GI101 was detected in the clinical and chemical analysis (FIGS. 73 to 79).

Experimental Example 21.5. Cytokine Analysis

Blood was collected from the monkeys in Experimental Example 23.1 one day before drug administration, and on days 1, 8, and 15 after drug administration. Here, the blood was collected in the same manner as in Experimental Example 23.3. Using the Bio-Plex 200 (Bio-Rad Laboratories, Inc.) instrument and the Non-Human Primate Cytokine Magnetic Bead Panel (EMD Millipore) Assay Kit, the collected blood was analyzed for TNF-α, IFN-γ IL-1, IL-2, IL-4, IL-6, IL-8, IL-10, and IL-12. As a result, no toxicity caused by GI101 was detected with respect to the cytokine analysis (FIGS. 80 and 81).

Experimental Example 23.6. Immune Cell Analysis

Blood was collected from the monkeys in Experimental Example 23.1 one day before drug administration, and on days 1, 8, and 15 after drug administration. Here, the blood was collected in the same manner as in Experimental Example 23.3. Using a flow cytometer (LSRFortessa X-20, Becton, Dickinson and Company), the collected blood was analyzed for the following items:
1) Ki67+CD4: CD45+/CD3+/CD4+/Ki67+
2) Ki67+CD8: CD45+/CD3+/CD8+/Ki67+
3) Ki67+Treg: CD45+/CD3+/FoxP3+/Ki67+
4) Ki67+ICOS+Treg: CD45+/CD3+/FoxP3+/Ki67+/CD278+
5) ICOS+ Treg: CD45+/CD3+/FoxP3+/CD278+
6) Ki67+NK cell: CD45+/CD16+ and CD56+/Ki67+.

As a result, in the immune cell analysis, all groups having received GI101 exhibited, on day 15, an increase in numbers of T cells, CD4+ T cells, CD8+ T cells, regulatory T cells, NK cells and Ki67+ T cells, Ki67+CD4+ T cells, Ki67+CD8+ T cells, Ki67+ regulatory T cells, Ki67+ ICOS+ regulatory T cells, Ki67+NK cells, ICOS+ regulatory T cells.

Specifically, in lymphocytes, proportions of T cells, CD4+ T cells, regulatory T cells increased and a proportion of NK cells decreased, while a proportion of CD8+ T cells did not change. A proportion of regulatory T cells increased on day 3 and decreased on days 8 and 15. However, the proportion was still higher than the control group.

In addition, regarding proportions of immune cells, which are Ki67+, in the respective immune cells, proportions of Ki67+ T cells, Ki67+CD4+ T cells, Ki67+CD8+ T cells, Ki67+ regulatory T cells, Ki67+ ICOS+ regulatory T cells, Ki67+NK cells, and ICOS+ regulatory T cells increased.

Furthermore, proportions of Ki67+ T cells, Ki67+CD8+ T cells, and Ki67+NK cells increased on days 3, 8, and 15; proportions of Ki67+CD4+ T cells and Ki67+ regulatory T cells increased on days 3 and 8; and proportions of Ki67+ ICOS+ regulatory T cells and ICOS+ regulatory T cells increased only on day 8 (FIGS. 82 to 87).

Experimental Example 23.7. Pathological Analysis

On day 16, the monkeys in Experimental Example 23.1 were sacrificed and all organs and tissues were fixed using 10% formalin. However, the testes were fixed using a formalin-sucrose-acetic acid (FSA) solution, and the eyes and optic nerve were fixed using 1% formaldehyde-2.5% glutaraldehyde in phosphate buffer. Hematoxylin-eosin staining was performed on the organs and tissues in the items listed in Table 4 below, and observations were made under an optical microscope.

TABLE 4

| | | | Specimen preparation | |
|---|---|---|---|---|
| Organ/tissue | Fixation | Organ weight | HE-stained | Note |
| Heart | O | O | — | Left ventricular papillary muscle, right ventricular wall and areas including the coronary artery and aortic valve |
| Aorta (thoracic) | O | — | | |
| Sternum | O | — | | Decalcified |
| Sternal bone marrow | | — | | |
| Femurs | O (R&L) | — | | Distal articular cartilage and shaft; decalcified |
| Femoral bone marrow | O (R) | — | | Decalcified |
| Thymus | O | O | O | |
| Spleen | O | O | O | |
| Submandibular lymph nodes | O | — | O | |
| Mesenteric lymph nodes | O | — | O | |
| Trachea | O | — | | Decalcified |

TABLE 4-continued

| Organ/tissue | Fixation | Organ weight | HE-stained | Note |
|---|---|---|---|---|
| Bronchi | O (R&L) | O (R&L separated) | — | Left anterior and right posterior lobes |
| Lungs | | | | |
| Tongue | O | — | | |
| Submandibular glands | O (R&L) | O (R&L combined) | | |
| Parotid glands | O (R&L) | — | | |
| Esophagus | O | — | | |
| Stomach | O | — | | Cardia, body and pylorus |
| Duodenum | O | — | | |
| Jejunum | O | — | | |
| Ileum | O | — | | |
| Peyer's patches | | | | |
| Cecum | O | — | | |
| Colon | O | — | | |
| Rectum | O | — | | |
| Liver | O | O | O | Left lateral lobe and right medial lobe including the gallbladder |
| Gallbladder | | (with bile-drained gallbladder) | O | |
| Pancreas | O | O | — | |
| Kidneys | O (R&L) | O (R&L separated) | O (R&L) | |
| Urinary bladder | O | — | | |
| Pituitary | O | O | | |
| Thyroids | O (R&L) | O (R&L separated) | | |
| Parathyroids | | | | |
| Adrenals | O (R&L) | O (R&L separated) | | |
| Testes | O (R&L) | O (R&L separated) | | |
| Epididymides | O (R&L) | O (R&L separated) | | |
| Prostate | O | O | | |
| Seminal vesicles | O | O | — | |
| Brain | O | O | — | Cerebrum (frontal, parietal (including basal ganglia and hippocampus) and occipital lobes); cerebellum; pons; and medulla oblongata |
| Spinal cord (thoracic) | O | — | | |
| Sciatic nerve | O (L) | — | | |
| Eyes | O (R&L) | — | | |
| Optic nerves | O (R&L) | — | | |
| Lacrimal glands | O (R&L) | — | | |
| Skeletal muscle (biceps femoris) | O (L) | — | | |
| Skin (thoracic) | O | — | | |
| Injection site (tail vein) | O | — | | Decalcified |
| Skin of the thoracic or medial femoral region with ID No. | O | — | — | |

O: conducted
—: Not conducted
R&L: Both the right and left organs/tissues were conducted.
L: Either the right or left organ/tissue (usually the left) was conducted.
R: Either the right or left organ/tissue (usually the right) was conducted As a result, the group treated with GI101 at a dose of 5 mg/kg/day or 10 mg/kg/day exhibited an increase in spleen weight (FIG. 88). No significant changes were observed in the other tissues. In conclusion, in the groups having received GI101, some changes were observed but no toxicity was observed.

VI. Experimental Example 24 for Identifying Anticancer Effect of GI02. Identification of Anticancer Effect of GI02-M45

Experimental Example 24.1. Identification of Anticancer Effect of GI02-M45 in Mice Transplanted with Mouse-Derived Colorectal Cancer Cells $5 \times 10^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 mm$^3$ to 120 mm3 were separated. Then, the subjects were intravenously administered 0.1 ml of GI102-M45. A total of three administrations were given once every three days after the first administration, and PBS was given for a negative control. The tumor size was measured daily to identify an anticancer effect. Activity of GI102-M45 was identified in the same manner as in Experimental Example 16.

Experimental Example 24.2. Identification of Anticancer Effect of GI102-M45 in Mice Transplanted with Mouse-Derived Lung Cells C57BL/6 mice (female, 7-week-old) acquired from Orient Bio were subjected to an acclimation period of 7 days. Then, $5 \times 10^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M45 at a dose of 0.1 mg/kg or 1 mg/kg was administered intravenously thereto. A total of three administrations were given once every three days after the first administration. The tumor size was measured daily. Activity of GI102-M45 was identified in the same manner as in Experimental Example 20.1.

Experimental Example 25. Identification of Anticancer Effect of GI102-M61

Experimental Example 25.1. Identification of Anticancer Effect of GI102-M61 in Mice Transplanted with Mouse-Derived Colorectal Cancer Cells $5 \times 10^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 mm$^3$ to 120 mm$^3$ were separated. Then, the subjects were intravenously administered 0.1 ml of GI102-M61. A total of three administrations were given once every three days after the first administration, and PBS was given to a negative control. The tumor size was measured daily to identify an anticancer effect. Activity of GI102-M61 was identified in the same manner as in Experimental Example 16.

Experimental Example 25.2. Identification of Antitumor Effect of GI102-M61 in Mice Transplanted with Mouse-Derived Lung Cancer Cells C57BL/6 mice (female, 7-week-old) acquired from Orient Bio were subjected to an acclimation period of 7 days. Then, 5×10$^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M61 at a dose of 0.1 mg/kg or 1 mg/kg was administered intravenously thereto. A total of three administrations were given once every three days after the first administration. The tumor size was measured daily. Activity of GI102-M61 was identified in the same manner as in Experimental Example 20.1.

Experimental Example 26. Identification of Anticancer Effect of GI102-M72

Experimental Example 26.1. Identification of Antitumor Effect of GI102-M72 in Mice Transplanted with Mouse-Derived Colorectal Cancer Cells 5×10$^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 mm$^3$ to 120 mm$^3$ were separated. Then, the subjects were intravenously administered 0.1 ml of GI102-M72. A total of three administrations were given once every three days after the first administration, and PBS was given to a negative control. The tumor size was measured daily to identify an anticancer effect. Activity of GI102-M72 was identified in the same manner as in Experimental Example 16.

Experimental Example 26.2. Identification of Anticancer Effect of GI102-M72 in Mice Transplanted with Mouse-Lung Cancer Cells C57BL/6 mice (female, 7-week-old) acquired from Orient Bio were subjected to an acclimation period of 7 days. Then, 5×10$^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M72 at a dose of 0.1 mg/kg or 1 mg/kg was administered intravenously thereto. A total of three administrations were given once every three days after the first administration. The tumor size was measured daily. Activity of GI102-M72 was identified in the same manner as in Experimental Example 20.1.

---

The invention claimed is:

1. A fusion protein of the following structural formula (I) or (II):

N'-X-[linker (1)]$_n$-Fc domain-[linker (2)]$_m$-Y-C' (I)

N'-Y-[linker (1)]$_n$-Fc domain-[linker (2)]$_m$-X-C' (II)

in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

2. The fusion protein of claim 1, wherein n and m are each independently 1.

3. The fusion protein of claim 1, wherein the IL-2 protein comprises the amino acid sequence of SEQ ID NO: 10.

4. The fusion protein of claim 1, wherein the IL-2 protein is an IL-2 variant.

5. The fusion protein of claim 4, wherein the IL-2 variant is obtained by substitution of at least one selected from the $38^{th}$ $42^{nd}$ $45^{th}$, $61^{st}$, and $72^{nd}$ amino acids in the amino acid sequence of SEQ ID NO: 10.

6. The fusion protein of claim 4, wherein the IL-2 variant comprises at least one substitution selected from the group consisting of R38A, F42A, Y45A, E61R, and L72G in the amino acid sequence of SEQ ID NO: 10.

7. The fusion protein of claim 4, wherein the IL-2 variant comprises any one selected from the following substitution combinations (a) to (d) in the amino acid sequence of SEQ ID NO: 10:
(a) R38A/F42A
(b) R38A/F42A/Y45A
(c) R38A/F42A/E61R
(d) R38A/F42A/L72G.

8. The fusion protein of claim 4, wherein the IL-2 variant comprises the amino acid sequence of SEQ ID NO: 6, 22, 23, or 24.

9. The fusion protein of claim 1, wherein the CD80 protein comprises the amino acid sequence of SEQ ID NO: 11.

10. The fusion protein of claim 1, wherein the CD80 protein is a CD80 fragment.

11. The fusion protein of claim 10, wherein the CD80 fragment consists of the $35^{th}$ amino acid to $242^{nd}$ amino acid in the amino acid sequence of SEQ ID NO: 11.

12. The fusion protein of claim 1, wherein the Fc domain is a wild type or variant.

13. The fusion protein of claim 1, wherein the Fc domain comprises the amino acid sequence of SEQ ID NO: 4.

14. The fusion protein of claim 12, wherein the variant of the Fc domain comprises the amino acid sequence of SEQ ID NO: 12.

15. The fusion protein of claim 1, wherein the linker (1) is a peptide linker consisting of the amino acid sequence of SEQ ID NO: 3.

16. The fusion protein of claim 1, wherein the linker (2) is a peptide linker consisting of the amino acid sequence of SEQ ID NO: 5.

17. The fusion protein of claim 1, wherein the fusion protein comprises a sequence identity of 90% or higher to the amino acid sequence of SEQ ID NO: 9, 26, 28, or 30.

18. A fusion protein dimer wherein two fusion proteins of claim 1 are attached to each other.

19. The fusion protein dimer of claim 18, wherein the fusion protein dimer is a homodimer.

20. A pharmaceutical composition comprising as an active ingredient:
the fusion protein of claim 1 or a dimer comprising two of the fusion protein attached to each other.

21. The pharmaceutical composition of claim 20, further comprising a pharmaceutically acceptable carrier.

\* \* \* \* \*